US008741605B2

(12) United States Patent
Cobleigh et al.

(10) Patent No.: US 8,741,605 B2

(45) Date of Patent: Jun. 3, 2014

(54) GENE EXPRESSION MARKERS FOR BREAST CANCER PROGNOSIS

(75) Inventors: Melody A. Cobleigh, Riverside, IL (US); Steve Shak, Hillsborough, CA (US); Joffre B. Baker, Montara, CA (US); Maureen T. Cronin, Los Altos, CA (US)

(73) Assignee: Genomic Health, Inc., Redwood City, CA (US)

( * ) Notice: Subject to any disclaimer, the term of this patent is extended or adjusted under 35 U.S.C. 154(b) by 0 days.

(21) Appl. No.: 13/473,526

(22) Filed: May 16, 2012

(65) Prior Publication Data

US 2012/0225433 A1 Sep. 6, 2012

Related U.S. Application Data

(60) Division of application No. 13/221,549, filed on Aug. 30, 2011, now Pat. No. 8,206,919, which is a division of application No. 12/478,632, filed on Jun. 4, 2009, now Pat. No. 8,034,565, which is a continuation of application No. 10/758,307, filed on Jan. 14, 2004, now Pat. No. 7,569,345.

(60) Provisional application No. 60/440,861, filed on Jan. 15, 2003.

(51) Int. Cl.
*C12P 19/34* (2006.01)

(52) U.S. Cl.
USPC ........................ 435/91.2; 435/6.12; 536/24.33

(58) Field of Classification Search
None
See application file for complete search history.

(56) References Cited

U.S. PATENT DOCUMENTS

| | | | |
|---|---|---|---|
| 4,699,877 | A | 10/1987 | Cline et al. |
| 4,968,603 | A | 11/1990 | Slamon et al. |
| 5,015,568 | A | 5/1991 | Tsujimoto et al. |
| 5,202,429 | A | 4/1993 | Tsujimoto et al. |
| 5,459,251 | A | 10/1995 | Tsujimoto et al. |
| RE35,491 | E | 4/1997 | Cline et al. |
| 5,670,325 | A | 9/1997 | Lapidus et al. |
| 5,741,650 | A | 4/1998 | Lapidus et al. |
| 5,830,665 | A | 11/1998 | Shuber et al. |
| 5,830,753 | A | 11/1998 | Coulie et al. |
| 5,858,678 | A | 1/1999 | Chinnadurai |
| 5,861,278 | A | 1/1999 | Wong et al. |
| 5,928,870 | A | 7/1999 | Lapidus et al. |
| 5,952,178 | A | 9/1999 | Lapidus et al. |
| 5,952,179 | A | 9/1999 | Chinnadurai |
| 5,962,312 | A | 10/1999 | Plowman et al. |
| 5,985,553 | A | 11/1999 | King et al. |
| 6,001,583 | A | 12/1999 | Margolis |
| 6,020,137 | A | 2/2000 | Lapidus et al. |
| 6,100,029 | A | 8/2000 | Lapidus et al. |
| 6,143,529 | A | 11/2000 | Lapidus et al. |
| 6,146,828 | A | 11/2000 | Lapidus et al. |
| 6,171,798 | B1 | 1/2001 | Levine et al. |
| 6,203,993 | B1 | 3/2001 | Shuber et al. |
| 6,207,401 | B1 | 3/2001 | Plowman et al. |
| 6,207,452 | B1 | 3/2001 | Govindaswamy |
| 6,214,558 | B1 | 4/2001 | Shuber et al. |
| 6,245,523 | B1 | 6/2001 | Altieri |
| 6,248,535 | B1 | 6/2001 | Danenberg et al. |
| 6,251,601 | B1 | 6/2001 | Bao et al. |
| 6,271,002 | B1 | 8/2001 | Linsley et al. |
| 6,322,986 | B1 | 11/2001 | Ross |
| 6,331,396 | B1 | 12/2001 | Silverman et al. |
| 6,414,134 | B1 | 7/2002 | Reed |
| 6,582,919 | B2 | 6/2003 | Danenberg |
| 6,602,670 | B2 | 8/2003 | Danenberg |
| 6,618,679 | B2 | 9/2003 | Loehrlein et al. |
| 6,620,606 | B2 | 9/2003 | Bandman et al. |
| 6,696,558 | B2 | 2/2004 | Reed et al. |
| 6,716,575 | B2 | 4/2004 | Plowman et al. |
| 6,750,013 | B2 | 6/2004 | Gish et al. |
| 6,800,737 | B2 | 10/2004 | Altieri |
| 6,943,150 | B1 | 9/2005 | Altieri |
| 7,056,674 | B2 | 6/2006 | Baker et al. |
| 7,526,387 | B2 | 4/2009 | Baker et al. |
| 7,569,345 | B2 | 8/2009 | Cobleigh et al. |
| 7,622,251 | B2 | 11/2009 | Baker et al. |
| 7,871,769 | B2 | 1/2011 | Baker et al. |
| 7,888,019 | B2 | 2/2011 | Kiefer et al. |
| 7,930,104 | B2 | 4/2011 | Baker et al. |
| 7,939,261 | B2 | 5/2011 | Baker et al. |
| 2001/0051344 | A1 | 12/2001 | Shalon et al. |
| 2002/0004491 | A1 | 1/2002 | Xu et al. |
| 2002/0009736 | A1 | 1/2002 | Wang |
| 2002/0039764 | A1 | 4/2002 | Rosen et al. |
| 2002/0160395 | A1 | 10/2002 | Altieri et al. |
| 2003/0073112 | A1 | 4/2003 | Zhang et al. |
| 2003/0104499 | A1 | 6/2003 | Pressman et al. |

(Continued)

FOREIGN PATENT DOCUMENTS

| | | | |
|---|---|---|---|
| EP | 108564 | B1 | 5/1988 |
| EP | 1365034 | A2 | 11/2003 |

(Continued)

OTHER PUBLICATIONS

Peirce et al. (J Endocrinol. Oct. 2001;171(1):R1-4).*
Specht et al. (Am J Pathol. Feb. 2001;158(2):419-29).*
Cobleigh M. A. et al., "Tumor gene expression and prognosis in breast cancer patients with 10 or more positive lymph nodes," Clin Cancer Res., 2005, vol. 11 (24 Pt 1), pp. 8623-8631.
Cronin, et al., "Analytical validation of the Oncotype DX genomic diagnostic test for recurrence prognosis and therapeutic response prediction in node-negative, estrogen receptor-positive breast cancer," Clinical Chemistry, 2007, vol. 53, pp. 1084-1091.

(Continued)

*Primary Examiner* — Suchira Pande
(74) *Attorney, Agent, or Firm* — Bozicevic, Field & Francis

(57) ABSTRACT

The present invention provides gene sets the expression of which is important in the diagnosis and/or prognosis of breast cancer.

19 Claims, No Drawings

(56) References Cited

U.S. PATENT DOCUMENTS

| | | | |
|---|---|---|---|
| 2003/0143539 A1 | 7/2003 | Bertucci et al. |
| 2003/0165952 A1 | 9/2003 | Linnarsson et al. |
| 2003/0180791 A1 | 9/2003 | Chinnadurai |
| 2003/0198970 A1 | 10/2003 | Roberts |
| 2003/0198972 A1 | 10/2003 | Erlander et al. |
| 2003/0219771 A1 | 11/2003 | Bevilacqua et al. |
| 2003/0224374 A1 | 12/2003 | Dai et al. |
| 2003/0225528 A1 | 12/2003 | Baker et al. |
| 2003/0229455 A1 | 12/2003 | Bevilacqua et al. |
| 2004/0009489 A1 | 1/2004 | Golub et al. |
| 2004/0126775 A1 | 7/2004 | Altieri et al. |
| 2004/0133352 A1 | 7/2004 | Bevilacqua et al. |
| 2005/0064455 A1 | 3/2005 | Baker et al. |
| 2005/0260572 A1 | 11/2005 | Kato et al. |
| 2008/0085519 A1 | 4/2008 | Gabrin et al. |
| 2009/0125247 A1 | 5/2009 | Baker et al. |
| 2009/0311702 A1 | 12/2009 | Shak et al. |
| 2011/0123990 A1 | 5/2011 | Baker et al. |
| 2011/0129833 A1 | 6/2011 | Baker et al. |
| 2011/0171641 A1 | 7/2011 | Baker et al. |
| 2011/0178374 A1 | 7/2011 | Baker et al. |

FOREIGN PATENT DOCUMENTS

| | | | |
|---|---|---|---|
| WO | WO9902714 | A1 | 1/1999 |
| WO | WO9944062 | A1 | 9/1999 |
| WO | WO9964626 | A2 | 12/1999 |
| WO | WO9964627 | A2 | 12/1999 |
| WO | WO0050595 | A2 | 8/2000 |
| WO | WO0055173 | A1 | 9/2000 |
| WO | WO0055180 | A2 | 9/2000 |
| WO | WO0125250 | A1 | 4/2001 |
| WO | WO0140466 | A2 | 6/2001 |
| WO | WO01/51664 | A2 | 7/2001 |
| WO | WO0155320 | A2 | 8/2001 |
| WO | WO0170979 | A2 | 9/2001 |
| WO | WO0175160 | A1 | 10/2001 |
| WO | WO0200677 | A1 | 1/2002 |
| WO | WO0206526 | A1 | 1/2002 |
| WO | WO0208260 | A2 | 1/2002 |
| WO | WO0208261 | A2 | 1/2002 |
| WO | WO0208282 | A2 | 1/2002 |
| WO | WO0208765 | A2 | 1/2002 |
| WO | WO0210436 | A2 | 2/2002 |
| WO | WO0217852 | A2 | 3/2002 |
| WO | WO0246467 | A2 | 6/2002 |
| WO | WO02055988 | A2 | 7/2002 |
| WO | WO02059271 | A2 | 8/2002 |
| WO | WO02059377 | A2 | 8/2002 |
| WO | WO02068579 | A2 | 9/2002 |
| WO | WO02072828 | A1 | 9/2002 |
| WO | WO02103320 | A2 | 12/2002 |
| WO | WO03011897 | A1 | 2/2003 |
| WO | WO03078662 | A1 | 9/2003 |
| WO | WO03083096 | A2 | 10/2003 |
| WO | WO2004074518 | A1 | 9/2004 |
| WO | WO2004111603 | A2 | 12/2004 |
| WO | WO2007045996 | A1 | 4/2007 |
| WO | WO2009026128 | A2 | 2/2009 |
| WO | WO2009140304 | A1 | 11/2009 |

OTHER PUBLICATIONS

Hellemans, P. et al., "Prognostic value of bcl-2 expression in invasive breast cancer," Brit. J. Cancer, 1995, vol. 72, pp. 354-360.

Holten-Anderson N., et al., "Localization of tissue inhibitor of metalloproteinases 1 (TIMP-1) in human colorectal adenoma and adenocarcinoma," Int. J. Cancer, 2005, vol. 113, pp. 198-206.

Paik S. et al., "Gene expression and benefit of chemotherapy in women with node-negative, estrogen receptor positive breast cancer," Journal of Clinical Oncology, 2006, vol. 24, pp. 3726-3734.

Valkovic et al., "Correlation between vascular endothelial growth factor, angiogenesis, and tumor-associated macrophages in invasive ductal breast carcinoma," 2002, Virchows Archiv, vol. 440, pp. 583-588.

ARUP Laboratories, "PAM50 breast cancer intrinsic classifier (TM) breast cancer subtyping", URL:http://www.aruplab.com/Lab-Tests/General-Oncology/PAM50/index.jsp, 2011.

Paik et al., "A multigene assay to predict recurrence of tamoxifen-treated, node-negative breast cancer", The New England Journal of Medicine, vol. 351, No. 27, 2004, pp. 2817-2826.

Parker et al., Supervised risk predictor of breast cancer based on intrinsic subtypes, Journal of Clinical Oncology, vol. 27, No. 8, 2009, pp. 1160-1167.

Examination Report for European Patent Application No. 10162868.3 dated Jul. 31, 2013.

Summons to attend oral proceedings for European Patent Application No. 10162867.5 dated Aug. 2, 2013.

Examination Report from CA Patent App. No. 2,513,117 dated Feb. 29, 2012, 2 pages.

Noben-Trauth, K. et al., "*Myb12* (*Bmyb*) Maps to Mouse Chromosome 2 and Human Chromosome 20q13.1," *Genomics* 35:610-612 (1996).

Tanner, M.M. et al., "Amplification of Chromosomal Region 20q13 in Invasive Breast Cancer: Prognostic Implications," 1:1455-1461 (1995).

Affymetrix Genome U133A Array Apr. 2001, http://www.affymetrix.com/estore/browse/products.jsp navMode=34000 &productld= 131536&navAction= jump&ald=productsNav#1_1.

Affymetrix Genome U133A Array Apr. 2001, http://www.affymetrix.com/estore/browse/products.jsp navMode=34000 &productld=131536&navAction=jump&ald=productsNav#1_1, Affymetrix Product Family Data Sheet.

Ahmad A. et al., "Stromelysin 3: An independent prognostic factor for relapse-free survival in node-positive breast cancer and demonstration of novel breast carcinoma cell expression," Am. J. Pathol., 1998, vol. 152, No. 3, pp. 721-728.

Allison D.B., et al., "Microarray data analysis: from disarray to consolidation and consensus," Nature Reviews, Genetics, 2006, vol. 7, pp. 55-65.

AU Examiners Report in AU Application No. 2009238287, 3 pages, Issued Nov. 1, 2011.

Bertucci et al., "Gene expression profiling of primary breast carcinomas using arrays of candidate genes", Human Molecular Genetics, 2000, vol. 9, pp. 2981-2991.

Bhattacharjee et al., "Classification of human lung carcinomas by mRNA expression profiling reveals distinct adenocarcinoma subclasses", Proceedings of the National Academy of Sciences of USA, 2001, vol. 98, No. 24, pp. 13790-13795.

Bishop Philippe C. et al., "Differential sensitivity of cancer cells to inhibitors of the epidermal growth factor receptor family", Oncogene, 2002, vol. 21, No. 1, pp. 119-127.

Borresen Dale A. L., "Genetic profiling of breast cancer: From molecular portraits to clinical utility," Int. J. Biol. Markers, 2002, vol. 18, No. 1, pp. 54-56.

Brabender Jan et al., "Epidermal growth factor receptor and HER2-neu mRNA expression in non-small cell lung cancer is correlated with survival," Clinical Cancer Research, 2001, vol. 7, pp. 1850-1855.

Cambridge Healthtech Institute Conference Agenda; "Enabling molecular profiling with cellular resolution: Microgenomics using homogeneous cell samples"; Dec. 2002; 5 pgs.

Chenard M. P. et al., "High levels of stromelysin-3 correlate with poor prognosis in patients with breast carcinoma," Intl. J. Cancer, 1996, vol. 69, No. 6, pp. 448-451.

Ding Chumming et al., "A high-throughput gene expression analysis technique using competitive PCR and matrix-assisted laser desorption ionization time-of-flight MS," PNAS, 2003, vol. 100, No. 6, pp. 3059-3064.

Eley Greg D. et al., "A chromosomal region 7p11.2 transcript map: its development and application to the study of EGFR amplicons in glioblastoma", Neuro-oncology, 2002, vol. 4, No. 2, pp. 86-94

Engel G. et al., "Correlation between stromelysin-3 mRNA level and outcome of human breast cancer," Int. J. Cancer, 1994, vol. 58, No. 6, pp. 830-835.

(56) References Cited

OTHER PUBLICATIONS

European Search Report for Application No. EP10162867, mailed on Sep. 1, 2011, 6 pages.
European Search Report for Application No. EP10162867, mailed on Aug. 19, 2010, 8 pages.
European Search Report for Application No. EP10162868, mailed on Dec. 10, 2010, 11 pages.
Forozan Farahnaz et al., "Comparative genomic hybridization analysis of 38 breast cancer cell lines: A basis for interpreting complementary DNA microarray data", Cancer Research, 2000, vol. 60, No. 16, pp. 4519-4525.
Golub et al., "Molecular classification of cancer: class discovery and class prediction by gene expression monitoring", Science, 1999, vol. 286, pp. 531-537.
Guerin M. et al., "Structure and expression of c-erbb2 and EGF receptor genes in inflammatory and non-inflammatory breast cancer: prognostic significance," Intl. J. Cancer, 1989, vol. 43, pp. 201-208.
JP Patent Application No. 2006-500964, Office Action, dated Jul. 30, 2010.
Kononen J. et al., "Tissue microarrays for high-throughput molecular profiling of tumor specimens", Nature Medicine, 1998, vol. 4, No. 7, pp. 844-847.
Korfee et al., "The role of DNA-microarray in translational cancer research ", Current Pharmacogenomics, 2005, vol. 3, pp. 201-216.
Kroese et al., "Genetic tests and their evaluation: can we answer the key questions", Genetics in Medicine, 2004, vol. 6, pp. 475-480.
Leek R. D. et al., "Association of macrophage infiltration with angiogenesis and prognosis in invasive breast carcinoma," Cancer Research, 1996, vol. 56, pp. 4625-4629.
Lucentini, "Gene association studies typically wrong", The Scientist, 2004, vol. 18, No. 24, pp. 20.
Ludwig J.A., et al., "Biomarkers in cancer staging, prognosis and treatment selection," Nature Reviews, Cancer, 2005, vol. 5, pp. 845-856.
Martin et al., "Linking gene expression patterns to therapeutic groups in breast cancer", Cancer Research, 2000, vol. 60, pp. 2232-2238.
Meric, et al., "Translation initiation in cancer: a novel target for therapy," Mol.Cancer Ther., 2002, vol. 1, pp. 971-979.
Michiels S., et al., "Prediction of cancer outcome with microarrays: a multiple random validation strategy," Lancet, 2005, vol. 365, pp. 488-492.
Murphy et al., "Gene expression profiling in breast cancer: towards individualising patient management", Pathology, 2005, vol. 37, No. 4, pp. 271-277.
Murray P. A. et al., "The prognostic significance of transforming growth factors in human breast cancer", British J. Cancer, 1993, vol. 67, No. 6, pp. 1408-1412.
NCBI sequence of NM_002466, "Homo sapiens v-myb myeloblastosis viral oncogene homolog (avian)-like 2 (MYBL2), mRNA.".
Nuciforo P.G., et al., "Molecular and immunohistochemical analysis of HER2/neu oncogene in synovial sarcoma," Human Pathology, 2003, vol. 34, pp. 639-645.
Perou et al., "Molecular portraits of human breast tumors", Nature, 2000, vol. 406, pp. 747-752.
Proceedings of the Conference of the Japanese Cancer Association, 61st Conference (2002), p. 154 (3134).
Ramaswamy et al., "Multiclass cancer diagnosis using tumor gene expression signatures", Proceedings of the National Academy of Sciences of USA, 2001, vol. 98, No. 26, pp. 15149-15154.
Raschella Giuseppe et al., "Expression of B-myb in neuroblastoma tumors is a poor prognostic factor independent from MYCN amplification", Cancer Research, 1999, vol. 59, No. 14, pp. 3365-3368.
Rejthar A., "The intermediate filaments and prognostically oriented morphological classification in ductal breast carcinoma," Neoplasma, 1997, vol. 44, pp. 370-373.
Samuels Lev Yardena et al., "ASPP proteins specifically stimulate the apoptotic function of p53", Molecular Cell, 2001, vol. 8, No. 4, pp. 781-794.
Schorr K. et al., "Bcl-2 gene family and related proteins in mammary gland involution and breast cancer," J. Mammary Gland Biol. and Neoplasia, 1999, vol. 4, No. 2, pp. 153-164.
Sens Mary Ann et al., "Metallothionein isoform 3 overexpression is associated with breast cancers having a poor prognosis", Am. J. Pathol., 2001, vol. 159, pp. 21-26.
Sgroi D. C. et al., "In vivo gene expression profile analysis of human breast cancer progression," Cancer Research, 1999, vol. 59, No. 22, pp. 5656-5661.
Sorlie T. et al., "Gene expression patterns of breast carcinomas distinguish tumor subclasses with clinical implications", Proceedings of the National Academy of Sciences USA, 2001, vol. 98, No. 19, pp. 10869-10874.
Sun Z., et al., "Gene expression profiling on lung cancer outcome prediction: present clinical value and future premise," Cancer Epidemiology, Biomarkers & Prevention, 2006, vol. 15, pp. 2063-2068.
Ueno T. et al., "Significance of macrophage chemoattractant protein-1 in macrophage recruitment angiogenesis and survival in human breast cancer", Clin. Cancer Res., 2000, vol. 6, No. 8, pp. 3282-3289.
Van De Vijver et al., "A gene-expression signature as a predictor of survival in breast cancer", The New England Journal of Medicine, 2002, vol. 347, No. 25, pp. 1999-2009.
Veer Van T. L. J. et al., "Gene expression profiling predicts clinical outcome of breast cancer", Nature, 2002, vol. 415, No. 6871, pp. 530-536.
West et al., "Predicting the clinical status of human breast cancer by using gene expression profiles", Proceedings of the National Academy of Sciences of USA, 2001, vol. 98, No. 20, pp. 11462-11467.
Witton Caroline J. et al., "The sub-classification of breast cancers using molecular cytogenetic gene chips", Proc. Am. Assoc. Cancer Res. Annual Meeting; 2002, vol. 43, pp. 289.
Yan et al., "Dissecting complex epigenetic alterations in breast cancer using CpG island microarrays", Cancer Research, 2001, vol. 61, pp. 8375-7380.
Yang L. I. et al., "Badge beads array for the detection of gene expression: a high-throughput diagnostic bioassay", Genome Research, 2001, vol. 11, pp. 1888-1898.
Yeang et al., "Molecular classification of multiple tumor types", Bioinformatics, 2001, vol. 17 Suppl. 1, pp. S316-S322.
EP Patent Application No. 10162868.3, Third Party Observation filed Dec. 20, 2012 (7 pages.).
EP Patent Application No. 10162868.3, Third Party Observation filed Dec. 20, 2012 (8 pgs.).
EP Patent Application No. 10162867.5, Third Party Observation filed Jan. 21, 2013 (10 pgs.).
Bibikova, et al., "Quantitative Gene Expression Profiling in Formalin-Fixed, Paraffin-Embedded Tissues Using Universal Bead Arrays," Am. Journal Path. 165(5): 1799-1807 (2004).
Esteban, et al., "Prognostic Relevance of Carcinoembryonic Antigen and Estrogen Receptor Status in Breast Cancer Patients," Cancer 74(5): 1575-1583 (1994).
Hayes, et al., "Markers of increased risk for failure of adjuvant therapies," The Breast 12: 543-549 (2003).
Keyomarsi, et al., "Redundant cyclin overexpression and gene amplification in breast cancer cells," PNAS USA 90: 1112-1116 (1993).
Winters, et al., "Subcellular localization of cyclin B, Cdc2 and p21 WAF1/CIP1 in breast cancer: association with prognosis," European J. of Cancer 37: 2405-2412 (2001).

* cited by examiner

SEQUENCE LISTING

<160> NUMBER OF SEQ ID NOS: 440

<210> SEQ ID NO 1
<211> LENGTH: 81
<212> TYPE: DNA
<213> ORGANISM: Artificial Sequence
<220> FEATURE:
<223> OTHER INFORMATION: Amplicon

<400> SEQUENCE: 1
gcggcgagtt tccgatttaa agctgagctg cgaggaaaat ggcggcggga ggatcaaaat 60
acttgctgga tggtggactc a 81

<210> SEQ ID NO 2
<211> LENGTH: 71
<212> TYPE: DNA
<213> ORGANISM: Artificial Sequence
<220> FEATURE:
<223> OTHER INFORMATION: Amplicon

<400> SEQUENCE: 2
cgcttctatg gcgctgagat tgtgtcagcc ctggactacc tgcactcgga gaagaacgtg 60
gtgtaccggg a 71

<210> SEQ ID NO 3
<211> LENGTH: 71
<212> TYPE: DNA
<213> ORGANISM: Artificial Sequence
<220> FEATURE:
<223> OTHER INFORMATION: Amplicon

<400> SEQUENCE: 3
tcctgccacc cttcaaacct caggtcacgt ccgaggtcga cacaaggtac ttcgatgatg 60

-continued aatttaccgc c 71

<210> SEQ ID NO 4
<211> LENGTH: 69
<212> TYPE: DNA
<213> ORGANISM: Artificial Sequence
<220> FEATURE:
<223> OTHER INFORMATION: Amplicon

<400> SEQUENCE: 4
ggacagcagg aatgtgtttc tccatacagg tcacggggag ccaatggttc agaaacaaat 60
cgagtgggt 69

<210> SEQ ID NO 5
<211> LENGTH: 82
<212> TYPE: DNA
<213> ORGANISM: Artificial Sequence
<220> FEATURE:
<223> OTHER INFORMATION: Amplicon

<400> SEQUENCE: 5
tgtgagtgaa atgccttcta gtagtgaacc gtcctcggga gccgactatg actactcaga 60
agagtatgat aacgaaccac aa 82

<210> SEQ ID NO 6
<211> LENGTH: 66
<212> TYPE: DNA
<213> ORGANISM: Artificial Sequence
<220> FEATURE:
<223> OTHER INFORMATION: amplicon

<400> SEQUENCE: 6
cagcagatgt ggatcagcaa gcaggagtat gacgagtccg gcccctccat cgtccaccgc 60
aaatgc 66

<210> SEQ ID NO 7
<211> LENGTH: 80
<212> TYPE: DNA
<213> ORGANISM: Artificial Sequence
<220> FEATURE:
<223> OTHER INFORMATION: Amplicon

<400> SEQUENCE: 7
ggctcttgtg cgtactgtcc ttcgggctgg tgacagggaa gacatcactg agcctgccat 60
ctgtgctctt cgtcatctga 80

<210> SEQ ID NO 8
<211> LENGTH: 73
<212> TYPE: DNA
<213> ORGANISM: Artificial Sequence
<220> FEATURE:
<223> OTHER INFORMATION: Amplicon

<400> SEQUENCE: 8
gggtcaggtg cctcgagatc gggcttgggc ccagagcatg ttccagatcc cagagtttga 60
gccgagtgag cag 73

<210> SEQ ID NO 9
<211> LENGTH: 81
<212> TYPE: DNA
<213> ORGANISM: Artificial Sequence
<220> FEATURE:
<223> OTHER INFORMATION: Amplicon -continued

<400> SEQUENCE: 9
cgttgtcagc acttggaata caagatggtt gccgggtcat gttaattggg aaaaagaaca 60
gtccacagga agaggttgaa c 81

<210> SEQ ID NO 10
<211> LENGTH: 83
<212> TYPE: DNA
<213> ORGANISM: Artificial Sequence
<220> FEATURE:
<223> OTHER INFORMATION: Amplicon

<400> SEQUENCE: 10
cctggagggt cctgtacaat ctcatcatgg gactcctgcc cttacccagg ggccacagag 60
cccccgagat ggagcccaat tag 83

<210> SEQ ID NO 11
<211> LENGTH: 73
<212> TYPE: DNA
<213> ORGANISM: Artificial Sequence
<220> FEATURE:
<223> OTHER INFORMATION: Amplicon

<400> SEQUENCE: 11
cagatggacc tagtacccac tgagatttcc acgccgaagg acagcgatgg gaaaaatgcc 60
cttaaatcat agg 73

<210> SEQ ID NO 12
<211> LENGTH: 72
<212> TYPE: DNA
<213> ORGANISM: Artificial Sequence
<220> FEATURE:
<223> OTHER INFORMATION: Amplicon

<400> SEQUENCE: 12
atcctagccc tggtttttgg cctccttttt gctgtcacca gcgtcgcgtt ccttgtgcag 60
atgagaaggc ag 72

<210> SEQ ID NO 13
<211> LENGTH: 84
<212> TYPE: DNA
<213> ORGANISM: Artificial Sequence
<220> FEATURE:
<223> OTHER INFORMATION: Amplicon

<400> SEQUENCE: 13
ttcaggttgt tgcaggagac catgtacatg actgtctcca ttattgatcg gttcatgcag 60
aataattgtg tgcccaagaa gatg 84

<210> SEQ ID NO 14
<211> LENGTH: 69
<212> TYPE: DNA
<213> ORGANISM: Artificial Sequence
<220> FEATURE:
<223> OTHER INFORMATION: Amplicon

<400> SEQUENCE: 14
gcatgttcgt ggcctctaag atgaaggaga ccatccccct gacggccgag aagctgtgca 60
tctacaccg 69

<210> SEQ ID NO 15
<211> LENGTH: 71
<212> TYPE: DNA

<213> ORGANISM: Artificial Sequence
<220> FEATURE:
<223> OTHER INFORMATION: Amplicon

<400> SEQUENCE: 15
aaagaagatg atgaccgggt ttacccaaac tcaacgtgca agcctcggat tattgcacca 60
tccagaggct c 71

<210> SEQ ID NO 16
<211> LENGTH: 82
<212> TYPE: DNA
<213> ORGANISM: Artificial Sequence
<220> FEATURE:
<223> OTHER INFORMATION: Amplicon

<400> SEQUENCE: 16
atgctgtggc tccttcctaa ctggggcttt cttgacatgt aggttgcttg gtaataacct 60
ttttgtatat cacaatttgg gt 82

<210> SEQ ID NO 17
<211> LENGTH: 65
<212> TYPE: DNA
<213> ORGANISM: Artificial Sequence
<220> FEATURE:
<223> OTHER INFORMATION: Amplicon

<400> SEQUENCE: 17
agatgaagtg gaaggcgctt ttcaccgcgg ccatcctgca ggcacagttg ccgattacag 60
aggca 65

<210> SEQ ID NO 18
<211> LENGTH: 74
<212> TYPE: DNA
<213> ORGANISM: Artificial Sequence
<220> FEATURE:
<223> OTHER INFORMATION: Amplicon

<400> SEQUENCE: 18
tggttcccag ccctgtgtcc acctccaagc ccagattcag attcgagtca tgtacacaac 60
ccagggtgga ggag 74

<210> SEQ ID NO 19
<211> LENGTH: 64
<212> TYPE: DNA
<213> ORGANISM: Artificial Sequence
<220> FEATURE:
<223> OTHER INFORMATION: Amplicon

<400> SEQUENCE: 19
gggcgtggaa cagtttatct cagacatctg ccccaagaag gacgtactcg aaaccttcac 60
cgtg 64

<210> SEQ ID NO 20
<211> LENGTH: 81
<212> TYPE: DNA
<213> ORGANISM: Artificial Sequence
<220> FEATURE:
<223> OTHER INFORMATION: Amplicon

<400> SEQUENCE: 20
tgagtgtccc ccggtatctt ccccgccctg ccaatcccga tgaaattgga aattttattg 60
atgaaaatct gaaagcggct g 81

<210> SEQ ID NO 21
<211> LENGTH: 77
<212> TYPE: DNA
<213> ORGANISM: Artificial Sequence
<220> FEATURE:
<223> OTHER INFORMATION: Amplicon

<400> SEQUENCE: 21
tgacaatcag cacacctgca ttcaccgctc ggaagagggc ctgagctgca tgaataagga 60
tcacggctgt agtcaca 77

<210> SEQ ID NO 22
<211> LENGTH: 82
<212> TYPE: DNA
<213> ORGANISM: Artificial Sequence
<220> FEATURE:
<223> OTHER INFORMATION: Amplicon

<400> SEQUENCE: 22
gataaattgg tacaagggat cagcttttcc cagcccacat gtcctgatca tatgcttttg 60
aatagtcagt tacttggcac cc 82

<210> SEQ ID NO 23
<211> LENGTH: 72
<212> TYPE: DNA
<213> ORGANISM: Artificial Sequence
<220> FEATURE:
<223> OTHER INFORMATION: Amplicon

<400> SEQUENCE: 23
tgcctgtggt gggaagctca gtaactggga accaaaggat gatgctatgt cagaacaccg 60
gaggcatttt cc 72

<210> SEQ ID NO 24
<211> LENGTH: 86
<212> TYPE: DNA
<213> ORGANISM: Artificial Sequence
<220> FEATURE:
<223> OTHER INFORMATION: Amplicon

<400> SEQUENCE: 24
ggatatttcc gtggctctta ttcaaactct ccatcaaatc ctgtaaactc cagagcaaat 60
caagattttt ctgccttgat gagaag 86

<210> SEQ ID NO 25
<211> LENGTH: 86
<212> TYPE: DNA
<213> ORGANISM: Artificial Sequence
<220> FEATURE:
<223> OTHER INFORMATION: Amplicon

<400> SEQUENCE: 25
gacatttcca gtcctgcagt caatgcctct ctgccccacc ctttgttcag tgtggctggt 60
gccacgacaa atgtgtgcga tcggag 86

<210> SEQ ID NO 26
<211> LENGTH: 75
<212> TYPE: DNA
<213> ORGANISM: Artificial Sequence
<220> FEATURE:
<223> OTHER INFORMATION: Amplicon

<400> SEQUENCE: 26

-continued

```
ggcatcctgg cccaaagttt cccaaatcca ggcggctaga ggcccactgc ttcccaacta     60

ccagctgagg gggtc                                                      75


<210> SEQ ID NO 27
<211> LENGTH: 79
<212> TYPE: DNA
<213> ORGANISM: Artificial Sequence
<220> FEATURE:
<223> OTHER INFORMATION: Amplicon

<400> SEQUENCE: 27

tctgcagagt tggaagcact ctatggtgac atcgatgctg tggagctgta tcctgccctt     60

ctggtagaaa agcctcggc                                                  79


<210> SEQ ID NO 28
<211> LENGTH: 74
<212> TYPE: DNA
<213> ORGANISM: Artificial Sequence
<220> FEATURE:
<223> OTHER INFORMATION: Amplicon

<400> SEQUENCE: 28

gggaggctta tctcactgag tgagcagaat ctggtagact gctctgggcc tcaaggcaat     60

gaaggctgca atgg                                                       74


<210> SEQ ID NO 29
<211> LENGTH: 67
<212> TYPE: DNA
<213> ORGANISM: Artificial Sequence
<220> FEATURE:
<223> OTHER INFORMATION: Amplicon

<400> SEQUENCE: 29

tgtctcactg agcgagcaga atctggtgga ctgttcgcgt cctcaaggca atcagggctg     60

caatggt                                                               67


<210> SEQ ID NO 30
<211> LENGTH: 77
<212> TYPE: DNA
<213> ORGANISM: Artificial Sequence
<220> FEATURE:
<223> OTHER INFORMATION: Amplicon

<400> SEQUENCE: 30

cgctgacatc atgaatgttc ctcgaccggc tggaggcgag tttggatatg acaaagacac     60

atcgttgctg aaagaga                                                    77


<210> SEQ ID NO 31
<211> LENGTH: 73
<212> TYPE: DNA
<213> ORGANISM: Artificial Sequence
<220> FEATURE:
<223> OTHER INFORMATION: Amplicon

<400> SEQUENCE: 31

cacaatggcg gctctgaaga gttggctgtc gcgcagcgta acttcattct tcaggtacag     60

acagtgtttg tgt                                                        73


<210> SEQ ID NO 32
<211> LENGTH: 84
<212> TYPE: DNA
<213> ORGANISM: Artificial Sequence
<220> FEATURE:
```

<223> OTHER INFORMATION: Amplicon

<400> SEQUENCE: 32
ctctgagaca gtgcttcgat gactttgcag acttggtgcc ctttgactcc tgggagccgc 60
tcatgaggaa gttgggcctc atgg 84

<210> SEQ ID NO 33
<211> LENGTH: 62
<212> TYPE: DNA
<213> ORGANISM: Artificial Sequence
<220> FEATURE:
<223> OTHER INFORMATION: Amplicon

<400> SEQUENCE: 33
tgtcgatgga cttccagaac cacctgggca gctgccaaaa gtgtgatcca agctgtccca 60
at 62

<210> SEQ ID NO 34
<211> LENGTH: 82
<212> TYPE: DNA
<213> ORGANISM: Artificial Sequence
<220> FEATURE:
<223> OTHER INFORMATION: Amplicon

<400> SEQUENCE: 34
gatctaagat ggcgactgtc gaaccggaaa ccacccctac tcctaatccc ccgactacag 60
aagaggagaa aacggaatct aa 82

<210> SEQ ID NO 35
<211> LENGTH: 68
<212> TYPE: DNA
<213> ORGANISM: Artificial Sequence
<220> FEATURE:
<223> OTHER INFORMATION: Amplicon

<400> SEQUENCE: 35
ggcagtgtca ctgagtcctt gaaatcctcc cctgccccgc gggtctctgg attgggacgc 60
acagtgca 68

<210> SEQ ID NO 36
<211> LENGTH: 75
<212> TYPE: DNA
<213> ORGANISM: Artificial Sequence
<220> FEATURE:
<223> OTHER INFORMATION: Amplicon

<400> SEQUENCE: 36
gggccctcca gaacaatgat gggctttatg atcctgactg cgatgagagc gggctcttta 60
aggccaagca gtgca 75

<210> SEQ ID NO 37
<211> LENGTH: 76
<212> TYPE: DNA
<213> ORGANISM: Artificial Sequence
<220> FEATURE:
<223> OTHER INFORMATION: Amplicon

<400> SEQUENCE: 37
accgtaggct ctgctctgaa tgactctcct gtgggtctgg ctgcctatat tctagagaag 60
ttttccacct ggacca 76

<210> SEQ ID NO 38

-continued

<211> LENGTH: 81
<212> TYPE: DNA
<213> ORGANISM: Artificial Sequence
<220> FEATURE:
<223> OTHER INFORMATION: Amplicon

<400> SEQUENCE: 38
cggttatgtc atgccagata cacacctcaa aggtactccc tcctcccggg aaggcaccct 60
ttcttcagtg ggtctcagtt c 81

<210> SEQ ID NO 39
<211> LENGTH: 68
<212> TYPE: DNA
<213> ORGANISM: Artificial Sequence
<220> FEATURE:
<223> OTHER INFORMATION: Amplicon

<400> SEQUENCE: 39
cgtggtgccc ctctatgacc tgctgctgga gatgctggac gcccaccgcc tacatgcgcc 60
cactagcc 68

<210> SEQ ID NO 40
<211> LENGTH: 90
<212> TYPE: DNA
<213> ORGANISM: Artificial Sequence
<220> FEATURE:
<223> OTHER INFORMATION: Amplicon

<400> SEQUENCE: 40
ggctattcct cattttctct acaaagtggc ctcagtgaac atgaagaagg tagcctcctg 60
gaggagaatt tcggtgacag tctacaatcc 90

<210> SEQ ID NO 41
<211> LENGTH: 68
<212> TYPE: DNA
<213> ORGANISM: Artificial Sequence
<220> FEATURE:
<223> OTHER INFORMATION: Amplicon

<400> SEQUENCE: 41
cggtagtcaa gtccggatca agggcaagga gacggaattc tacctgtgca tgaaccgcaa 60
aggcaagc 68

<210> SEQ ID NO 42
<211> LENGTH: 74
<212> TYPE: DNA
<213> ORGANISM: Artificial Sequence
<220> FEATURE:
<223> OTHER INFORMATION: Amplicon

<400> SEQUENCE: 42
cacgggacat tcaccacatc gactactata aaaagacaac caacggccga ctgcctgtga 60
agtggatggc accc 74

<210> SEQ ID NO 43
<211> LENGTH: 67
<212> TYPE: DNA
<213> ORGANISM: Artificial Sequence
<220> FEATURE:
<223> OTHER INFORMATION: Amplicon

<400> SEQUENCE: 43
ccagtggagc gcttccatga cctgcgtcct gatgaagtgg ccgatttgtt tcagacgacc 60

-continued cagagag 67

<210> SEQ ID NO 44
<211> LENGTH: 75
<212> TYPE: DNA
<213> ORGANISM: Artificial Sequence
<220> FEATURE:
<223> OTHER INFORMATION: Amplicon

<400> SEQUENCE: 44
ttggtacctg tgggttagca tcaagttctc cccagggtag aattcaatca gagctccagt 60
ttgcatttgg atgtg 75

<210> SEQ ID NO 45
<211> LENGTH: 68
<212> TYPE: DNA
<213> ORGANISM: Artificial Sequence
<220> FEATURE:
<223> OTHER INFORMATION: Amplicon

<400> SEQUENCE: 45
tcagcagcaa gggcatcatg gaggaggatg aggcctgcgg gcgccagtac acgctcaaga 60
aaaccacc 68

<210> SEQ ID NO 46
<211> LENGTH: 74
<212> TYPE: DNA
<213> ORGANISM: Artificial Sequence
<220> FEATURE:
<223> OTHER INFORMATION: Amplicon

<400> SEQUENCE: 46
attccaccca tggcaaattc catggcaccg tcaaggctga gaacgggaag cttgtcatca 60
atggaaatcc catc 74

<210> SEQ ID NO 47
<211> LENGTH: 75
<212> TYPE: DNA
<213> ORGANISM: Artificial Sequence
<220> FEATURE:
<223> OTHER INFORMATION: Amplicon

<400> SEQUENCE: 47
caaaggagct cactgtggtg tctgtgttcc aaccactgaa tctggacccc atctgtgaat 60
aagccattct gactc 75

<210> SEQ ID NO 48
<211> LENGTH: 67
<212> TYPE: DNA
<213> ORGANISM: Artificial Sequence
<220> FEATURE:
<223> OTHER INFORMATION: Amplicon

<400> SEQUENCE: 48
ccatctgcat ccatcttgtt tgggctcccc acccttgaga agtgcctcag ataataccct 60
ggtggcc 67

<210> SEQ ID NO 49
<211> LENGTH: 73
<212> TYPE: DNA
<213> ORGANISM: Aritificial sequence
<220> FEATURE:
<223> OTHER INFORMATION: Amplicon -continued

<400> SEQUENCE: 49
cgaaaagatg ctgaacagtg acaaatccaa ctgaccagaa gggaggagga agctcactgg 60
tggctgttcc tga 73

<210> SEQ ID NO 50
<211> LENGTH: 86
<212> TYPE: DNA
<213> ORGANISM: Artificial Sequence
<220> FEATURE:
<223> OTHER INFORMATION: Amplicon

<400> SEQUENCE: 50
aagctatgag gaaaagaagt acacgatggg ggacgctcct gattatgaca gaagccagtg 60
gctgaatgaa aaattcaagc tgggcc 86

<210> SEQ ID NO 51
<211> LENGTH: 73
<212> TYPE: DNA
<213> ORGANISM: Artificial Sequence
<220> FEATURE:
<223> OTHER INFORMATION: Amplicon

<400> SEQUENCE: 51
cccactcagt agccaagtca caatgtttgg aaaacagccc gtttacttga gcaagactga 60
taccacctgc gtg 73

<210> SEQ ID NO 52
<211> LENGTH: 70
<212> TYPE: DNA
<213> ORGANISM: Artificial Sequence
<220> FEATURE:
<223> OTHER INFORMATION: Amplicon

<400> SEQUENCE: 52
cggtgtgaga agtgcagcaa gccctgtgcc cgagtgtgct atggtctggg catggagcac 60
ttgcgagagg 70

<210> SEQ ID NO 53
<211> LENGTH: 82
<212> TYPE: DNA
<213> ORGANISM: Artificial Sequence
<220> FEATURE:
<223> OTHER INFORMATION: Amplicon

<400> SEQUENCE: 53
tgaacataaa gtctgcaaca tggaaggtat tgcactgcac aggccacatt cacgtatatg 60
ataccaacag taaccaacct ca 82

<210> SEQ ID NO 54
<211> LENGTH: 73
<212> TYPE: DNA
<213> ORGANISM: Artificial Sequence
<220> FEATURE:
<223> OTHER INFORMATION: Amplicon

<400> SEQUENCE: 54
tccaggatgt taggaactgt gaagatggaa gggcatgaaa ccagcgactg gaacagctac 60
tacgcagaca cgc 73

<210> SEQ ID NO 55
<211> LENGTH: 70
<212> TYPE: DNA

<213> ORGANISM: Artificial Sequence
<220> FEATURE:
<223> OTHER INFORMATION: Amplicon

<400> SEQUENCE: 55
agaaccgcaa ggtgagcaag gtggagattc tccagcacgt catcgactac atcagggacc 60
ttcagttgga 70

<210> SEQ ID NO 56
<211> LENGTH: 76
<212> TYPE: DNA
<213> ORGANISM: Artificial Sequence
<220> FEATURE:
<223> OTHER INFORMATION: Amplicon

<400> SEQUENCE: 56
tccggagctg tgatctaagg aggctggaga tgtattgcgc acccctcaag cctgccaagt 60
cagctcgctc tgtccg 76

<210> SEQ ID NO 57
<211> LENGTH: 83
<212> TYPE: DNA
<213> ORGANISM: Artificial Sequence
<220> FEATURE:
<223> OTHER INFORMATION: Amplicon

<400> SEQUENCE: 57
gcatggtagc cgaagatttc acagtcaaaa tcggagattt tggtatgacg cgagatatct 60
atgagacaga ctattaccgg aaa 83

<210> SEQ ID NO 58
<211> LENGTH: 73
<212> TYPE: DNA
<213> ORGANISM: Artificial Sequence
<220> FEATURE:
<223> OTHER INFORMATION: Amplicon

<400> SEQUENCE: 58
gtggacagca ccatgaacat gttgggcggg ggaggcagtg ctggccggaa gcccctcaag 60
tcgggtatga agg 73

<210> SEQ ID NO 59
<211> LENGTH: 72
<212> TYPE: DNA
<213> ORGANISM: Artificial Sequence
<220> FEATURE:
<223> OTHER INFORMATION: Amplicon

<400> SEQUENCE: 59
cctgaacctt ccaaagatgg ctgaaaaaga tggatgcttc caatctggat tcaatgagga 60
gacttgcctg gt 72

<210> SEQ ID NO 60
<211> LENGTH: 74
<212> TYPE: DNA
<213> ORGANISM: Artificial Sequence
<220> FEATURE:
<223> OTHER INFORMATION: Amplicon

<400> SEQUENCE: 60
ccacagctca ccttctgtca ggtgtccatc ccagctccag ccagctccca gagaggaaga 60
gactggcact gagg 74

-continued

<210> SEQ ID NO 61
<211> LENGTH: 80
<212> TYPE: DNA
<213> ORGANISM: Artificial Sequence
<220> FEATURE:
<223> OTHER INFORMATION: Amplicon

<400> SEQUENCE: 61
cggactttgg gtgcgacttg acgagcggtg gttcgacaag tggccttgcg ggccggatcg 60
tcccagtgga agagttgtaa 80

<210> SEQ ID NO 62
<211> LENGTH: 78
<212> TYPE: DNA
<213> ORGANISM: Artificial Sequence
<220> FEATURE:
<223> OTHER INFORMATION: Amplicon

<400> SEQUENCE: 62
gcccagaggc tccatcgtcc atcctcttcc tccccagtcg gctgaactct ccccttgtct 60
gcactgttca aacctctg 78

<210> SEQ ID NO 63
<211> LENGTH: 83
<212> TYPE: DNA
<213> ORGANISM: Artificial Sequence
<220> FEATURE:
<223> OTHER INFORMATION: Amplicon

<400> SEQUENCE: 63
ggcctgctga gatcaaagac tacagtccct acttcaagac cattgaggac ctgaggaaca 60
agattctcac agccacagtg gac 83

<210> SEQ ID NO 64
<211> LENGTH: 73
<212> TYPE: DNA
<213> ORGANISM: Artificial Sequence
<220> FEATURE:
<223> OTHER INFORMATION: Amplicon

<400> SEQUENCE: 64
cgaggattgg ttcttcagca agacagagga actgaaccgc gaggtggcca ccaacagtga 60
gctggtgcag agt 73

<210> SEQ ID NO 65
<211> LENGTH: 68
<212> TYPE: DNA
<213> ORGANISM: Artificial Sequence
<220> FEATURE:
<223> OTHER INFORMATION: Amplicon

<400> SEQUENCE: 65
agagatcgag gctctcaagg aggagctgct cttcatgaag aagaaccacg aagaggaagt 60
aaaaggcc 68

<210> SEQ ID NO 66
<211> LENGTH: 77
<212> TYPE: DNA
<213> ORGANISM: Artificial Sequence
<220> FEATURE:
<223> OTHER INFORMATION: Amplicon

<400> SEQUENCE: 66
tgagcggcag aatcaggagt accagcggct catggacatc aagtcgcggc tggagcagga 60
gattgccacc taccgca 77

<210> SEQ ID NO 67
<211> LENGTH: 69
<212> TYPE: DNA
<213> ORGANISM: Artificial Sequence
<220> FEATURE:
<223> OTHER INFORMATION: Amplicon

<400> SEQUENCE: 67
tcagtggaga aggagttgga ccagtcaaca tctctgttgt cacaagcagt gtttcctctg 60
gatatggca 69

<210> SEQ ID NO 68
<211> LENGTH: 86
<212> TYPE: DNA
<213> ORGANISM: Artificial Sequence
<220> FEATURE:
<223> OTHER INFORMATION: Amplicon

<400> SEQUENCE: 68
ggatgaagct tacatgaaca aggtagagct ggagtctcgc ctggaagggc tgaccgacga 60
gatcaacttc ctcaggcagc tatatg 86

<210> SEQ ID NO 69
<211> LENGTH: 83
<212> TYPE: DNA
<213> ORGANISM: Artificial Sequence
<220> FEATURE:
<223> OTHER INFORMATION: Amplicon

<400> SEQUENCE: 69
ggaaagacca cctgaaaaac cacctccaga cccacgaccc caacaaaatg gcctttgggt 60
gtgaggagtg tgggaagaag tac 83

<210> SEQ ID NO 70
<211> LENGTH: 77
<212> TYPE: DNA
<213> ORGANISM: Artificial Sequence
<220> FEATURE:
<223> OTHER INFORMATION: Amplicon

<400> SEQUENCE: 70
cagatggcca ctttgagaac attttagctg acaacagtgt gaacgaccag accaaaatcc 60
ttgtggttaa tgctgcc 77

<210> SEQ ID NO 71
<211> LENGTH: 75
<212> TYPE: DNA
<213> ORGANISM: Artificial Sequence
<220> FEATURE:
<223> OTHER INFORMATION: Amplicon

<400> SEQUENCE: 71
gacttttgcc cgctaccttt cattccggcg tgacaacaat gagctgttgc tcttcatact 60
gaagcagtta gtggc 75

<210> SEQ ID NO 72
<211> LENGTH: 75
<212> TYPE: DNA
<213> ORGANISM: Artificial Sequence
<220> FEATURE:

<223> OTHER INFORMATION: Amplicon

<400> SEQUENCE: 72
ggagaacaat ccccttgaga cagaatatgg cctttctgtc tacaaggatc accagaccat 60
caccatccag gagat 75

<210> SEQ ID NO 73
<211> LENGTH: 82
<212> TYPE: DNA
<213> ORGANISM: Artificial Sequence
<220> FEATURE:
<223> OTHER INFORMATION: Amplicon

<400> SEQUENCE: 73
tgatggtcct atgtgtcaca ttcatcacag gtttcatacc aacacaggct tcagcacttc 60
ctttggtgtg tttcctgtcc ca 82

<210> SEQ ID NO 74
<211> LENGTH: 68
<212> TYPE: DNA
<213> ORGANISM: Artificial Sequence
<220> FEATURE:
<223> OTHER INFORMATION: Amplicon

<400> SEQUENCE: 74
ctacagggac gccatcgaat ccggatcttg atgctggtgt aagtgaacat tcaggtgatt 60
ggttggat 68

<210> SEQ ID NO 75
<211> LENGTH: 67
<212> TYPE: DNA
<213> ORGANISM: Artificial Sequence
<220> FEATURE:
<223> OTHER INFORMATION: Amplicon

<400> SEQUENCE: 75
gagaaccaat ctcaccgaca ggcagctggc agaggaatac ctgtaccgct atggttacac 60
tcgggtg 67

<210> SEQ ID NO 76
<211> LENGTH: 77
<212> TYPE: DNA
<213> ORGANISM: Artificial Sequence
<220> FEATURE:
<223> OTHER INFORMATION: Amplicon

<400> SEQUENCE: 76
ccgccctcac ctgaagagaa acgcgctcct tggcggacac tgggggagga gaggaagaag 60
cgcggctaac ttattcc 77

<210> SEQ ID NO 77
<211> LENGTH: 74
<212> TYPE: DNA
<213> ORGANISM: Artificial Sequence
<220> FEATURE:
<223> OTHER INFORMATION: Amplicon

<400> SEQUENCE: 77
gccgagatcg ccaagatgtt gccagggagg acagacaatg ctgtgaagaa tcactggaac 60
tctaccatca aaag 74

<210> SEQ ID NO 78

-continued

<211> LENGTH: 72
<212> TYPE: DNA
<213> ORGANISM: Artificial Sequence
<220> FEATURE:
<223> OTHER INFORMATION: Amplicon

<400> SEQUENCE: 78
ccctcgtgct gatgctactg aggagccagc gtctagggca gcagccgctt cctagaagac 60
caggtcatga tg 72

<210> SEQ ID NO 79
<211> LENGTH: 66
<212> TYPE: DNA
<213> ORGANISM: Artificial Sequence
<220> FEATURE:
<223> OTHER INFORMATION: Amplicon

<400> SEQUENCE: 79
cggtggacca cgaagagtta acccgggact tggagaagca ctgcagagac atggaagagg 60
cgagcc 66

<210> SEQ ID NO 80
<211> LENGTH: 68
<212> TYPE: DNA
<213> ORGANISM: Artificial Sequence
<220> FEATURE:
<223> OTHER INFORMATION: Amplicon

<400> SEQUENCE: 80
ctttgaaccc ttgcttgcaa taggtgtgcg tcagaagcac ccaggacttc catttgcttt 60
gtcccggg 68

<210> SEQ ID NO 81
<211> LENGTH: 81
<212> TYPE: DNA
<213> ORGANISM: Artificial Sequence
<220> FEATURE:
<223> OTHER INFORMATION: Amplicon

<400> SEQUENCE: 81
ccgcaacgtg gttttctcac cctatggggt ggcctcggtg ttggccatgc tccagctgac 60
aacaggagga gaaacccagc a 81

<210> SEQ ID NO 82
<211> LENGTH: 66
<212> TYPE: DNA
<213> ORGANISM: Artificial Sequence
<220> FEATURE:
<223> OTHER INFORMATION: Amplicon

<400> SEQUENCE: 82
ccagctctcc ttccagctac agatcaatgt ccctgtccga gtgctggagc taagtgagag 60
ccaccc 66

<210> SEQ ID NO 83
<211> LENGTH: 83
<212> TYPE: DNA
<213> ORGANISM: Artificial Sequence
<220> FEATURE:
<223> OTHER INFORMATION: Amplicon

<400> SEQUENCE: 83
ataccaatca ccgcacaaac ccaggctatt tgttaagtcc agtcacagcg caaagaaaca 60

-continued tatgcggaga aaatgctagt gtg 83

<210> SEQ ID NO 84
<211> LENGTH: 62
<212> TYPE: DNA
<213> ORGANISM: Artificial Sequence
<220> FEATURE:
<223> OTHER INFORMATION: Amplicon

<400> SEQUENCE: 84
gccatccgca aaggctttct cgcttgtcac cttgccatgt ggaagaaact ggcggaatgg 60
cc 62

<210> SEQ ID NO 85
<211> LENGTH: 85
<212> TYPE: DNA
<213> ORGANISM: Artificial Sequence
<220> FEATURE:
<223> OTHER INFORMATION: Amplicon

<400> SEQUENCE: 85
gcatcaggct gtcattatgg tgtccttacc tgtgggagct gtaaggtctt ctttaagagg 60
gcaatggaag ggcagcacaa ctact 85

<210> SEQ ID NO 86
<211> LENGTH: 66
<212> TYPE: DNA
<213> ORGANISM: Artificial Sequence
<220> FEATURE:
<223> OTHER INFORMATION: Amplicon

<400> SEQUENCE: 86
tctccatatc tgccttgcag agtctcctgc agcacctcat cgggctgagc aatctgaccc 60
acgtgc 66

<210> SEQ ID NO 87
<211> LENGTH: 86
<212> TYPE: DNA
<213> ORGANISM: Artificial Sequence
<220> FEATURE:
<223> OTHER INFORMATION: Amplicon

<400> SEQUENCE: 87
gccctcccag tgtgcaaata agggctgctg tttcgacgac accgttcgtg gggtcccctg 60
gtgcttctat cctaatacca tcgacg 86

<210> SEQ ID NO 88
<211> LENGTH: 78
<212> TYPE: DNA
<213> ORGANISM: Artificial Sequence
<220> FEATURE:
<223> OTHER INFORMATION: Amplicon

<400> SEQUENCE: 88
gaacttcttg agcaggagca tacccagggc ttcataatca ccttctgttc agcactagat 60
gatattcttg ggggtgga 78

<210> SEQ ID NO 89
<211> LENGTH: 77
<212> TYPE: DNA
<213> ORGANISM: Artificial Sequence
<220> FEATURE:
<223> OTHER INFORMATION: Amplicon

<400> SEQUENCE: 89
cgaagccctt acaagtttcc tagttcaccc ttacggattc ctggagggaa catctatatt 60
tcacccctga agagtcc 77

<210> SEQ ID NO 90
<211> LENGTH: 74
<212> TYPE: DNA
<213> ORGANISM: Artificial Sequence
<220> FEATURE:
<223> OTHER INFORMATION: Amplicon

<400> SEQUENCE: 90
ccagacgagc gattagaagc ggcagcttgt gaggtgaatg atttggggga agaggaggag 60
gaggaagagg agga 74

<210> SEQ ID NO 91
<211> LENGTH: 69
<212> TYPE: DNA
<213> ORGANISM: Artificial Sequence
<220> FEATURE:
<223> OTHER INFORMATION: Amplicon

<400> SEQUENCE: 91
catcttccag gaggaccact ctctgtggca ccctggacta cctgcccccct gaaatgattg 60 aaggtcgga 69

<210> SEQ ID NO 92
<211> LENGTH: 90
<212> TYPE: DNA
<213> ORGANISM: Artificial Sequence
<220> FEATURE:
<223> OTHER INFORMATION: Amplicon

<400> SEQUENCE: 92
cctggaggct gcaacatacc tcaatcctgt cccaggccgg atcctcctga agcccttttc 60
gcagcactgc tatcctccaa agccattgta 90

<210> SEQ ID NO 93
<211> LENGTH: 80
<212> TYPE: DNA
<213> ORGANISM: Artificial Sequence
<220> FEATURE:
<223> OTHER INFORMATION: Amplicon

<400> SEQUENCE: 93
tgttttgatt cccgggctta ccaggtgaga agtgagggag gaagaaggca gtgtcccttt 60
tgctagagct gacagctttg 80

<210> SEQ ID NO 94
<211> LENGTH: 65
<212> TYPE: DNA
<213> ORGANISM: Artificial Sequence
<220> FEATURE:
<223> OTHER INFORMATION: Amplicon

<400> SEQUENCE: 94
gcccgaaacg ccgaatataa tcccaagcgg tttgctgcgg taatcatgag gataagagag 60
ccacg 65

<210> SEQ ID NO 95
<211> LENGTH: 83
<212> TYPE: DNA

-continued

<213> ORGANISM: Artificial Sequence
<220> FEATURE:
<223> OTHER INFORMATION: Amplicon

<400> SEQUENCE: 95
ggtgtgccac agaccttcct acttggcctg taatcacctg tgcagccttt tgtgggcctt 60
caaaactctg tcaagaactc cgt 83

<210> SEQ ID NO 96
<211> LENGTH: 75
<212> TYPE: DNA
<213> ORGANISM: Artificial Sequence
<220> FEATURE:
<223> OTHER INFORMATION: Amplicon

<400> SEQUENCE: 96
tccctgcggt cccagatagc ctgaatcctg cccggagtgg aactgaagcc tgcacagtgt 60
ccaccctgtt cccac 75

<210> SEQ ID NO 97
<211> LENGTH: 72
<212> TYPE: DNA
<213> ORGANISM: Artificial Sequence
<220> FEATURE:
<223> OTHER INFORMATION: Amplicon

<400> SEQUENCE: 97
aatccaaggg ggagagtgat gacttccata tggactttga ctcagctgtg gctcctcggg 60
caaaatctgt ac 72

<210> SEQ ID NO 98
<211> LENGTH: 66
<212> TYPE: DNA
<213> ORGANISM: Artificial Sequence
<220> FEATURE:
<223> OTHER INFORMATION: Amplicon

<400> SEQUENCE: 98
tgtggacatc ttcccctcag acttccctac tgagccacct tctctgccac gaaccggtcg 60
ggctag 66

<210> SEQ ID NO 99
<211> LENGTH: 82
<212> TYPE: DNA
<213> ORGANISM: Artificial Sequence
<220> FEATURE:
<223> OTHER INFORMATION: Amplicon

<400> SEQUENCE: 99
ctatatgcag ccagagatgt gacagccacc gtggacagcc tgccactcat cacagcctcc 60
attctcagta agaaactcgt gg 82

<210> SEQ ID NO 100
<211> LENGTH: 81
<212> TYPE: DNA
<213> ORGANISM: Artificial Sequence
<220> FEATURE:
<223> OTHER INFORMATION: Amplicon

<400> SEQUENCE: 100
gggccaaata ttcagaagct tttatatcag aggaccacca tagcggccat ggagaccatc 60
tctgtcccat catacccatc c 81

-continued

<210> SEQ ID NO 101
<211> LENGTH: 73
<212> TYPE: DNA
<213> ORGANISM: Artificial Sequence
<220> FEATURE:
<223> OTHER INFORMATION: Amplicon

<400> SEQUENCE: 101
cttcacagtg ctcctgcagt ctctctgtgt ggctgtaact tacgtgtact ttaccaacga 60
gctgaagcag atg 73

<210> SEQ ID NO 102
<211> LENGTH: 65
<212> TYPE: DNA
<213> ORGANISM: Artificial Sequence
<220> FEATURE:
<223> OTHER INFORMATION: Amplicon

<400> SEQUENCE: 102
gcctcggtgt gcctttcaac atcgccagct acgccctgct cacgtacatg attgcgcaca 60
tcacg 65

<210> SEQ ID NO 103
<211> LENGTH: 70
<212> TYPE: DNA
<213> ORGANISM: Artificial Sequence
<220> FEATURE:
<223> OTHER INFORMATION: Amplicon

<400> SEQUENCE: 103
gtggatgtgc cctgaaggac aagccaggcg tctacacgag agtctcacac ttcttaccct 60
ggatccgcag 70

<210> SEQ ID NO 104
<211> LENGTH: 67
<212> TYPE: DNA
<213> ORGANISM: Artificial Sequence
<220> FEATURE:
<223> OTHER INFORMATION: Amplicon

<400> SEQUENCE: 104
gccctggatt tcagaaagag ccaagtctgg atctgggacc ctttccttcc ttccctggct 60
tgtaact 67

<210> SEQ ID NO 105
<211> LENGTH: 71
<212> TYPE: DNA
<213> ORGANISM: Artificial Sequence
<220> FEATURE:
<223> OTHER INFORMATION: Amplicon

<400> SEQUENCE: 105
ctgctgtctt gggtgcattg gagccttgcc ttgctgctct acctccacca tgccaagtgg 60
tcccaggctg c 71

<210> SEQ ID NO 106
<211> LENGTH: 71
<212> TYPE: DNA
<213> ORGANISM: Artificial Sequence
<220> FEATURE:
<223> OTHER INFORMATION: Amplicon

<400> SEQUENCE: 106
tgacgatggc ctggagtgtg tgcccactgg gcagcaccaa gtccggatgc agatcctcat 60
gatccggtac c 71

<210> SEQ ID NO 107
<211> LENGTH: 75
<212> TYPE: DNA
<213> ORGANISM: Artificial Sequence
<220> FEATURE:
<223> OTHER INFORMATION: Amplicon

<400> SEQUENCE: 107
agaggcatcc atgaacttca cacttgcggg ctgcatcagc acacgctcct atcaacccaa 60
gtactgtgga gtttg 75

<210> SEQ ID NO 108
<211> LENGTH: 77
<212> TYPE: DNA
<213> ORGANISM: Artificial Sequence
<220> FEATURE:
<223> OTHER INFORMATION: Amplicon

<400> SEQUENCE: 108
gcagttggaa gacacaggaa agtatcccca aattgcagat ttatcaacgg cttttatctt 60
gaaaatagtg ccacgca 77

<210> SEQ ID NO 109
<211> LENGTH: 76
<212> TYPE: DNA
<213> ORGANISM: Artificial Sequence
<220> FEATURE:
<223> OTHER INFORMATION: Amplicon

<400> SEQUENCE: 109
agactgtgga gtttgatgtt gttgaaggag aaaagggtgc ggaggcagca aatgttacag 60
gtcctggtgg tgttcc 76

<210> SEQ ID NO 110
<211> LENGTH: 70
<212> TYPE: DNA
<213> ORGANISM: Artificial Sequence
<220> FEATURE:
<223> OTHER INFORMATION: Amplicon

<400> SEQUENCE: 110
acccagtagc aaggagaagc ccactcactg ctccgagtgc ggcaaagctt tcagaaccta 60
ccaccagctg 70

<210> SEQ ID NO 111
<211> LENGTH: 19
<212> TYPE: DNA
<213> ORGANISM: Artificial Sequence
<220> FEATURE:
<223> OTHER INFORMATION: forward primer

<400> SEQUENCE: 111
gcggcgagtt tccgattta 19

<210> SEQ ID NO 112
<211> LENGTH: 21
<212> TYPE: DNA
<213> ORGANISM: Artificial Sequence
<220> FEATURE:
<223> OTHER INFORMATION: reverse primer -continued

<400> SEQUENCE: 112
tgagtccacc atccagcaag t 21

<210> SEQ ID NO 113
<211> LENGTH: 21
<212> TYPE: DNA
<213> ORGANISM: Artificial Sequence
<220> FEATURE:
<223> OTHER INFORMATION: probe

<400> SEQUENCE: 113
atggcggcgg gaggatcaaa a 21

<210> SEQ ID NO 114
<211> LENGTH: 20
<212> TYPE: DNA
<213> ORGANISM: Artificial Sequence
<220> FEATURE:
<223> OTHER INFORMATION: forward primer

<400> SEQUENCE: 114
cgcttctatg gcgctgagat 20

<210> SEQ ID NO 115
<211> LENGTH: 20
<212> TYPE: DNA
<213> ORGANISM: Artificial Sequence
<220> FEATURE:
<223> OTHER INFORMATION: reverse primer

<400> SEQUENCE: 115
tcccggtaca ccacgttctt 20

<210> SEQ ID NO 116
<211> LENGTH: 24
<212> TYPE: DNA
<213> ORGANISM: Artificial Sequence
<220> FEATURE:
<223> OTHER INFORMATION: probe

<400> SEQUENCE: 116
cagccctgga ctacctgcac tcgg 24

<210> SEQ ID NO 117
<211> LENGTH: 19
<212> TYPE: DNA
<213> ORGANISM: Artificial Sequence
<220> FEATURE:
<223> OTHER INFORMATION: forward primer

<400> SEQUENCE: 117
tcctgccacc cttcaaacc 19

<210> SEQ ID NO 118
<211> LENGTH: 21
<212> TYPE: DNA
<213> ORGANISM: Artificial Sequence
<220> FEATURE:
<223> OTHER INFORMATION: reverse primer

<400> SEQUENCE: 118
ggcggtaaat tcatcatcga a 21

<210> SEQ ID NO 119
<211> LENGTH: 24
<212> TYPE: DNA

-continued

<213> ORGANISM: Artificial Sequence
<220> FEATURE:
<223> OTHER INFORMATION: probe

<400> SEQUENCE: 119
caggtcacgt ccgaggtcga caca 24

<210> SEQ ID NO 120
<211> LENGTH: 20
<212> TYPE: DNA
<213> ORGANISM: Artificial Sequence
<220> FEATURE:
<223> OTHER INFORMATION: forward primer

<400> SEQUENCE: 120
ggacagcagg aatgtgtttc 20

<210> SEQ ID NO 121
<211> LENGTH: 20
<212> TYPE: DNA
<213> ORGANISM: Artificial Sequence
<220> FEATURE:
<223> OTHER INFORMATION: reverse primer

<400> SEQUENCE: 121
acccactcga tttgtttctg 20

<210> SEQ ID NO 122
<211> LENGTH: 22
<212> TYPE: DNA
<213> ORGANISM: Artificial Sequence
<220> FEATURE:
<223> OTHER INFORMATION: probe

<400> SEQUENCE: 122
cattggctcc ccgtgacctg ta 22

<210> SEQ ID NO 123
<211> LENGTH: 27
<212> TYPE: DNA
<213> ORGANISM: Artificial Sequence
<220> FEATURE:
<223> OTHER INFORMATION: forward primer

<400> SEQUENCE: 123
tgtgagtgaa atgccttcta gtagtga 27

<210> SEQ ID NO 124
<211> LENGTH: 23
<212> TYPE: DNA
<213> ORGANISM: Artificial Sequence
<220> FEATURE:
<223> OTHER INFORMATION: probe

<400> SEQUENCE: 124
ccgtcctcgg gagccgacta tga 23

<210> SEQ ID NO 125
<211> LENGTH: 27
<212> TYPE: DNA
<213> ORGANISM: Artificial Sequence
<220> FEATURE:
<223> OTHER INFORMATION: reverse primer

<400> SEQUENCE: 125
ttgtggttcg ttatcatact cttctga 27

-continued

<210> SEQ ID NO 126
<211> LENGTH: 21
<212> TYPE: DNA
<213> ORGANISM: Artificial Sequence
<220> FEATURE:
<223> OTHER INFORMATION: forward primer

<400> SEQUENCE: 126
cagcagatgt ggatcagcaa g 21

<210> SEQ ID NO 127
<211> LENGTH: 18
<212> TYPE: DNA
<213> ORGANISM: Artificial Sequence
<220> FEATURE:
<223> OTHER INFORMATION: reverse primer

<400> SEQUENCE: 127
gcatttgcgg tggacgat 18

<210> SEQ ID NO 128
<211> LENGTH: 23
<212> TYPE: DNA
<213> ORGANISM: Artificial Sequence
<220> FEATURE:
<223> OTHER INFORMATION: probe

<400> SEQUENCE: 128
aggagtatga cgagtccggc ccc 23

<210> SEQ ID NO 129
<211> LENGTH: 22
<212> TYPE: DNA
<213> ORGANISM: Artificial Sequence
<220> FEATURE:
<223> OTHER INFORMATION: forward primer

<400> SEQUENCE: 129
ggctcttgtg cgtactgtcc tt 22

<210> SEQ ID NO 130
<211> LENGTH: 23
<212> TYPE: DNA
<213> ORGANISM: Artificial Sequence
<220> FEATURE:
<223> OTHER INFORMATION: reverse primer

<400> SEQUENCE: 130
tcagatgacg aagagcacag atg 23

<210> SEQ ID NO 131
<211> LENGTH: 29
<212> TYPE: DNA
<213> ORGANISM: Artificial Sequence
<220> FEATURE:
<223> OTHER INFORMATION: probe

<400> SEQUENCE: 131
aggctcagtg atgtcttccc tgtcaccag 29

<210> SEQ ID NO 132
<211> LENGTH: 19
<212> TYPE: DNA
<213> ORGANISM: Artificial Sequence
<220> FEATURE:
<223> OTHER INFORMATION: forward primer

<400> SEQUENCE: 132
gggtcaggtg cctcgagat 19

<210> SEQ ID NO 133
<211> LENGTH: 21
<212> TYPE: DNA
<213> ORGANISM: Artificial Sequence
<220> FEATURE:
<223> OTHER INFORMATION: reverse primer

<400> SEQUENCE: 133
ctgctcactc ggctcaaact c 21

<210> SEQ ID NO 134
<211> LENGTH: 24
<212> TYPE: DNA
<213> ORGANISM: Artificial Sequence
<220> FEATURE:
<223> OTHER INFORMATION: probe

<400> SEQUENCE: 134
tgggcccaga gcatgttcca gatc 24

<210> SEQ ID NO 135
<211> LENGTH: 23
<212> TYPE: DNA
<213> ORGANISM: Artificial Sequence
<220> FEATURE:
<223> OTHER INFORMATION: forward primer

<400> SEQUENCE: 135
cgttgtcagc acttggaata caa 23

<210> SEQ ID NO 136
<211> LENGTH: 24
<212> TYPE: DNA
<213> ORGANISM: Artificial Sequence
<220> FEATURE:
<223> OTHER INFORMATION: reverse primer

<400> SEQUENCE: 136
gttcaacctc ttcctgtgga ctgt 24

<210> SEQ ID NO 137
<211> LENGTH: 26
<212> TYPE: DNA
<213> ORGANISM: Artificial Sequence
<220> FEATURE:
<223> OTHER INFORMATION: probe

<400> SEQUENCE: 137
cccaattaac atgacccggc aaccat 26

<210> SEQ ID NO 138
<211> LENGTH: 20
<212> TYPE: DNA
<213> ORGANISM: Artificial Sequence
<220> FEATURE:
<223> OTHER INFORMATION: forward primer

<400> SEQUENCE: 138
cctggagggt cctgtacaat 20

<210> SEQ ID NO 139
<211> LENGTH: 19
<212> TYPE: DNA

<213> ORGANISM: Artificial Sequence
<220> FEATURE:
<223> OTHER INFORMATION: reverse primer

<400> SEQUENCE: 139
ctaattgggc tccatctcg 19

<210> SEQ ID NO 140
<211> LENGTH: 24
<212> TYPE: DNA
<213> ORGANISM: Artificial Sequence
<220> FEATURE:
<223> OTHER INFORMATION: probe

<400> SEQUENCE: 140
catcatggga ctcctgccct tacc 24

<210> SEQ ID NO 141
<211> LENGTH: 25
<212> TYPE: DNA
<213> ORGANISM: Artificial Sequence
<220> FEATURE:
<223> OTHER INFORMATION: forward primer

<400> SEQUENCE: 141
cagatggacc tagtacccac tgaga 25

<210> SEQ ID NO 142
<211> LENGTH: 22
<212> TYPE: DNA
<213> ORGANISM: Artificial Sequence
<220> FEATURE:
<223> OTHER INFORMATION: probe

<400> SEQUENCE: 142
ttccacgccg aaggacagcg at 22

<210> SEQ ID NO 143
<211> LENGTH: 24
<212> TYPE: DNA
<213> ORGANISM: Artificial Sequence
<220> FEATURE:
<223> OTHER INFORMATION: reverse primer

<400> SEQUENCE: 143
cctatgattt aagggcattt ttcc 24

<210> SEQ ID NO 144
<211> LENGTH: 20
<212> TYPE: DNA
<213> ORGANISM: Artificial Sequence
<220> FEATURE:
<223> OTHER INFORMATION: forward primer

<400> SEQUENCE: 144
atcctagccc tggtttttgg 20

<210> SEQ ID NO 145
<211> LENGTH: 20
<212> TYPE: DNA
<213> ORGANISM: Artificial sequence
<220> FEATURE:
<223> OTHER INFORMATION: reverse primer

<400> SEQUENCE: 145
ctgccttctc atctgcacaa 20

-continued

<210> SEQ ID NO 146
<211> LENGTH: 20
<212> TYPE: DNA
<213> ORGANISM: Artificial Sequence
<220> FEATURE:
<223> OTHER INFORMATION: probe

<400> SEQUENCE: 146
tttgctgtca ccagcgtcgc 20

<210> SEQ ID NO 147
<211> LENGTH: 20
<212> TYPE: DNA
<213> ORGANISM: Artificial Sequence
<220> FEATURE:
<223> OTHER INFORMATION: forward primer

<400> SEQUENCE: 147
ttcaggttgt tgcaggagac 20

<210> SEQ ID NO 148
<211> LENGTH: 20
<212> TYPE: DNA
<213> ORGANISM: Artificial Sequence
<220> FEATURE:
<223> OTHER INFORMATION: reverse primer

<400> SEQUENCE: 148
catcttcttg ggcacacaat 20

<210> SEQ ID NO 149
<211> LENGTH: 27
<212> TYPE: DNA
<213> ORGANISM: Artificial Sequence
<220> FEATURE:
<223> OTHER INFORMATION: probe

<400> SEQUENCE: 149
tgtctccatt attgatcggt tcatgca 27

<210> SEQ ID NO 150
<211> LENGTH: 21
<212> TYPE: DNA
<213> ORGANISM: Artificial Sequence
<220> FEATURE:
<223> OTHER INFORMATION: forward primer

<400> SEQUENCE: 150
gcatgttcgt ggcctctaag a 21

<210> SEQ ID NO 151
<211> LENGTH: 22
<212> TYPE: DNA
<213> ORGANISM: Artificial Sequence
<220> FEATURE:
<223> OTHER INFORMATION: reverse primer

<400> SEQUENCE: 151
cggtgtagat gcacagcttc tc 22

<210> SEQ ID NO 152
<211> LENGTH: 23
<212> TYPE: DNA
<213> ORGANISM: Artificial Sequence
<220> FEATURE:
<223> OTHER INFORMATION: probe

<400> SEQUENCE: 152
aaggagacca tccccctgac ggc 23

<210> SEQ ID NO 153
<211> LENGTH: 24
<212> TYPE: DNA
<213> ORGANISM: Artificial Sequence
<220> FEATURE:
<223> OTHER INFORMATION: forward primer

<400> SEQUENCE: 153
aaagaagatg atgaccgggt ttac 24

<210> SEQ ID NO 154
<211> LENGTH: 20
<212> TYPE: DNA
<213> ORGANISM: Artificial Sequence
<220> FEATURE:
<223> OTHER INFORMATION: reverse primer

<400> SEQUENCE: 154
gagcctctgg atggtgcaat 20

<210> SEQ ID NO 155
<211> LENGTH: 24
<212> TYPE: DNA
<213> ORGANISM: Artificial Sequence
<220> FEATURE:
<223> OTHER INFORMATION: probe

<400> SEQUENCE: 155
caaactcaac gtgcaagcct cgga 24

<210> SEQ ID NO 156
<211> LENGTH: 22
<212> TYPE: DNA
<213> ORGANISM: Artificial Sequence
<220> FEATURE:
<223> OTHER INFORMATION: forward primer

<400> SEQUENCE: 156
atgctgtggc tccttcctaa ct 22

<210> SEQ ID NO 157
<211> LENGTH: 27
<212> TYPE: DNA
<213> ORGANISM: Artificial Sequence
<220> FEATURE:
<223> OTHER INFORMATION: reverse primer

<400> SEQUENCE: 157
acccaaattg tgatatacaa aaaggtt 27

<210> SEQ ID NO 158
<211> LENGTH: 30
<212> TYPE: DNA
<213> ORGANISM: Artificial Sequence
<220> FEATURE:
<223> OTHER INFORMATION: probe

<400> SEQUENCE: 158
taccaagcaa cctacatgtc aagaaagccc 30

<210> SEQ ID NO 159
<211> LENGTH: 20
<212> TYPE: DNA

<213> ORGANISM: Artificial Sequence
<220> FEATURE:
<223> OTHER INFORMATION: forward primer

<400> SEQUENCE: 159
agatgaagtg gaaggcgctt 20

<210> SEQ ID NO 160
<211> LENGTH: 18
<212> TYPE: DNA
<213> ORGANISM: Artificial Sequence
<220> FEATURE:
<223> OTHER INFORMATION: probe

<400> SEQUENCE: 160
caccgcggcc atcctgca 18

<210> SEQ ID NO 161
<211> LENGTH: 21
<212> TYPE: DNA
<213> ORGANISM: Artificial Sequence
<220> FEATURE:
<223> OTHER INFORMATION: reverse primer

<400> SEQUENCE: 161
tgcctctgta atcggcaact g 21

<210> SEQ ID NO 162
<211> LENGTH: 18
<212> TYPE: DNA
<213> ORGANISM: Artificial Sequence
<220> FEATURE:
<223> OTHER INFORMATION: forward primer

<400> SEQUENCE: 162
tggttcccag ccctgtgt 18

<210> SEQ ID NO 163
<211> LENGTH: 28
<212> TYPE: DNA
<213> ORGANISM: Artificial Sequence
<220> FEATURE:
<223> OTHER INFORMATION: probe

<400> SEQUENCE: 163
ctccaagccc agattcagat tcgagtca 28

<210> SEQ ID NO 164
<211> LENGTH: 19
<212> TYPE: DNA
<213> ORGANISM: Artificial Sequence
<220> FEATURE:
<223> OTHER INFORMATION: reverse primer

<400> SEQUENCE: 164
ctcctccacc ctgggttgt 19

<210> SEQ ID NO 165
<211> LENGTH: 20
<212> TYPE: DNA
<213> ORGANISM: Artificial Sequence
<220> FEATURE:
<223> OTHER INFORMATION: forward primer

<400> SEQUENCE: 165
gggcgtggaa cagtttatct 20

<210> SEQ ID NO 166
<211> LENGTH: 19
<212> TYPE: DNA
<213> ORGANISM: Artificial Sequence
<220> FEATURE:
<223> OTHER INFORMATION: reverse primer

<400> SEQUENCE: 166
cacggtgaag gtttcgagt 19

<210> SEQ ID NO 167
<211> LENGTH: 24
<212> TYPE: DNA
<213> ORGANISM: Artificial Sequence
<220> FEATURE:
<223> OTHER INFORMATION: probe

<400> SEQUENCE: 167
agacatctgc cccaagaagg acgt 24

<210> SEQ ID NO 168
<211> LENGTH: 21
<212> TYPE: DNA
<213> ORGANISM: Artificial Sequence
<220> FEATURE:
<223> OTHER INFORMATION: forward primer

<400> SEQUENCE: 168
tgagtgtccc ccggtatctt c 21

<210> SEQ ID NO 169
<211> LENGTH: 21
<212> TYPE: DNA
<213> ORGANISM: Artificial Sequence
<220> FEATURE:
<223> OTHER INFORMATION: reverse primer

<400> SEQUENCE: 169
cagccgcttt cagattttca t 21

<210> SEQ ID NO 170
<211> LENGTH: 27
<212> TYPE: DNA
<213> ORGANISM: Artificial Sequence
<220> FEATURE:
<223> OTHER INFORMATION: probe

<400> SEQUENCE: 170
tgccaatccc gatgaaattg gaaattt 27

<210> SEQ ID NO 171
<211> LENGTH: 21
<212> TYPE: DNA
<213> ORGANISM: Artificial Sequence
<220> FEATURE:
<223> OTHER INFORMATION: forward primer

<400> SEQUENCE: 171
tgacaatcag cacacctgca t 21

<210> SEQ ID NO 172
<211> LENGTH: 23
<212> TYPE: DNA
<213> ORGANISM: Artificial Sequence
<220> FEATURE:
<223> OTHER INFORMATION: reverse primer

<400> SEQUENCE: 172
tgtgactaca gccgtgatcc tta 23

<210> SEQ ID NO 173
<211> LENGTH: 20
<212> TYPE: DNA
<213> ORGANISM: Artificial Sequence
<220> FEATURE:
<223> OTHER INFORMATION: probe

<400> SEQUENCE: 173
caggccctct tccgagcggt 20

<210> SEQ ID NO 174
<211> LENGTH: 26
<212> TYPE: DNA
<213> ORGANISM: Artificial Sequence
<220> FEATURE:
<223> OTHER INFORMATION: forward primer

<400> SEQUENCE: 174
gataaattgg tacaagggat cagctt 26

<210> SEQ ID NO 175
<211> LENGTH: 24
<212> TYPE: DNA
<213> ORGANISM: Artificial Sequence
<220> FEATURE:
<223> OTHER INFORMATION: reverse primer

<400> SEQUENCE: 175
gggtgccaag taactgacta ttca 24

<210> SEQ ID NO 176
<211> LENGTH: 26
<212> TYPE: DNA
<213> ORGANISM: Artificial Sequence
<220> FEATURE:
<223> OTHER INFORMATION: probe

<400> SEQUENCE: 176
ccagcccaca tgtcctgatc atatgc 26

<210> SEQ ID NO 177
<211> LENGTH: 18
<212> TYPE: DNA
<213> ORGANISM: Artificial Sequence
<220> FEATURE:
<223> OTHER INFORMATION: forward primer

<400> SEQUENCE: 177
tgcctgtggt gggaagct 18

<210> SEQ ID NO 178
<211> LENGTH: 19
<212> TYPE: DNA
<213> ORGANISM: Artificial Sequence
<220> FEATURE:
<223> OTHER INFORMATION: reverse primer

<400> SEQUENCE: 178
ggaaaatgcc tccggtgtt 19

<210> SEQ ID NO 179
<211> LENGTH: 30
<212> TYPE: DNA

<213> ORGANISM: Artificial Sequence
<220> FEATURE:
<223> OTHER INFORMATION: probe

<400> SEQUENCE: 179
tgacatagca tcatcctttg gttcccagtt 30

<210> SEQ ID NO 180
<211> LENGTH: 24
<212> TYPE: DNA
<213> ORGANISM: Artificial Sequence
<220> FEATURE:
<223> OTHER INFORMATION: forward primer

<400> SEQUENCE: 180
ggatatttcc gtggctctta ttca 24

<210> SEQ ID NO 181
<211> LENGTH: 30
<212> TYPE: DNA
<213> ORGANISM: Artificial Sequence
<220> FEATURE:
<223> OTHER INFORMATION: probe

<400> SEQUENCE: 181
tctccatcaa atcctgtaaa ctccagagca 30

<210> SEQ ID NO 182
<211> LENGTH: 25
<212> TYPE: DNA
<213> ORGANISM: Artificial Sequence
<220> FEATURE:
<223> OTHER INFORMATION: reverse primer

<400> SEQUENCE: 182
cttctcatca aggcagaaaa atctt 25

<210> SEQ ID NO 183
<211> LENGTH: 22
<212> TYPE: DNA
<213> ORGANISM: Artificial Sequence
<220> FEATURE:
<223> OTHER INFORMATION: forward primer

<400> SEQUENCE: 183
gacatttcca gtcctgcagt ca 22

<210> SEQ ID NO 184
<211> LENGTH: 23
<212> TYPE: DNA
<213> ORGANISM: Artificial Sequence
<220> FEATURE:
<223> OTHER INFORMATION: probe

<400> SEQUENCE: 184
tgcctctctg ccccaccctt tgt 23

<210> SEQ ID NO 185
<211> LENGTH: 20
<212> TYPE: DNA
<213> ORGANISM: Artificial Sequence
<220> FEATURE:
<223> OTHER INFORMATION: reverse primer

<400> SEQUENCE: 185
ctccgatcgc acacatttgt 20

<210> SEQ ID NO 186
<211> LENGTH: 18
<212> TYPE: DNA
<213> ORGANISM: Artificial Sequence
<220> FEATURE:
<223> OTHER INFORMATION: forward primer

<400> SEQUENCE: 186
ggcatcctgg cccaaagt 18

<210> SEQ ID NO 187
<211> LENGTH: 21
<212> TYPE: DNA
<213> ORGANISM: Artificial Sequence
<220> FEATURE:
<223> OTHER INFORMATION: reverse primer

<400> SEQUENCE: 187
gaccccctca gctggtagtt g 21

<210> SEQ ID NO 188
<211> LENGTH: 23
<212> TYPE: DNA
<213> ORGANISM: Artificial Sequence
<220> FEATURE:
<223> OTHER INFORMATION: probe

<400> SEQUENCE: 188
cccaaatcca ggcggctaga ggc 23

<210> SEQ ID NO 189
<211> LENGTH: 23
<212> TYPE: DNA
<213> ORGANISM: Artificial Sequence
<220> FEATURE:
<223> OTHER INFORMATION: forward primer

<400> SEQUENCE: 189
tctgcagagt tggaagcact cta 23

<210> SEQ ID NO 190
<211> LENGTH: 28
<212> TYPE: DNA
<213> ORGANISM: Artificial Sequence
<220> FEATURE:
<223> OTHER INFORMATION: probe

<400> SEQUENCE: 190
caggatacag ctccacagca tcgatgtc 28

<210> SEQ ID NO 191
<211> LENGTH: 21
<212> TYPE: DNA
<213> ORGANISM: Artificial Sequence
<220> FEATURE:
<223> OTHER INFORMATION: reverse primer

<400> SEQUENCE: 191
gccgaggctt ttctaccaga a 21

<210> SEQ ID NO 192
<211> LENGTH: 23
<212> TYPE: DNA
<213> ORGANISM: Artificial Sequence
<220> FEATURE:
<223> OTHER INFORMATION: forward primer

<400> SEQUENCE: 192
gggaggctta tctcactgag tga 23

<210> SEQ ID NO 193
<211> LENGTH: 19
<212> TYPE: DNA
<213> ORGANISM: Artificial Sequence
<220> FEATURE:
<223> OTHER INFORMATION: reverse primer

<400> SEQUENCE: 193
ccattgcagc cttcattgc 19

<210> SEQ ID NO 194
<211> LENGTH: 29
<212> TYPE: DNA
<213> ORGANISM: Artificial Sequence
<220> FEATURE:
<223> OTHER INFORMATION: probe

<400> SEQUENCE: 194
ttgaggccca gagcagtcta ccagattct 29

<210> SEQ ID NO 195
<211> LENGTH: 21
<212> TYPE: DNA
<213> ORGANISM: Artificial Sequence
<220> FEATURE:
<223> OTHER INFORMATION: forward primer

<400> SEQUENCE: 195
tgtctcactg agcgagcaga a 21

<210> SEQ ID NO 196
<211> LENGTH: 19
<212> TYPE: DNA
<213> ORGANISM: Artificial Sequence
<220> FEATURE:
<223> OTHER INFORMATION: reverse primer

<400> SEQUENCE: 196
accattgcag ccctgattg 19

<210> SEQ ID NO 197
<211> LENGTH: 24
<212> TYPE: DNA
<213> ORGANISM: Artificial Sequence
<220> FEATURE:
<223> OTHER INFORMATION: probe

<400> SEQUENCE: 197
cttgaggacg cgaacagtcc acca 24

<210> SEQ ID NO 198
<211> LENGTH: 22
<212> TYPE: DNA
<213> ORGANISM: Artificial Sequence
<220> FEATURE:
<223> OTHER INFORMATION: forward primer

<400> SEQUENCE: 198
cgctgacatc atgaatgttc ct 22

<210> SEQ ID NO 199
<211> LENGTH: 24
<212> TYPE: DNA

-continued

<213> ORGANISM: Artificial Sequence
<220> FEATURE:
<223> OTHER INFORMATION: reverse primer

<400> SEQUENCE: 199
tctctttcag caacgatgtg tctt 24

<210> SEQ ID NO 200
<211> LENGTH: 25
<212> TYPE: DNA
<213> ORGANISM: Artificial Sequence
<220> FEATURE:
<223> OTHER INFORMATION: probe

<400> SEQUENCE: 200
tcatatccaa actcgcctcc agccg 25

<210> SEQ ID NO 201
<211> LENGTH: 19
<212> TYPE: DNA
<213> ORGANISM: Artificial Sequence
<220> FEATURE:
<223> OTHER INFORMATION: forward primer

<400> SEQUENCE: 201
cacaatggcg gctctgaag 19

<210> SEQ ID NO 202
<211> LENGTH: 26
<212> TYPE: DNA
<213> ORGANISM: Artificial Sequence
<220> FEATURE:
<223> OTHER INFORMATION: reverse primer

<400> SEQUENCE: 202
acacaaacac tgtctgtacc tgaaga 26

<210> SEQ ID NO 203
<211> LENGTH: 23
<212> TYPE: DNA
<213> ORGANISM: Artificial Sequence
<220> FEATURE:
<223> OTHER INFORMATION: probe

<400> SEQUENCE: 203
aagttacgct gcgcgacagc caa 23

<210> SEQ ID NO 204
<211> LENGTH: 24
<212> TYPE: DNA
<213> ORGANISM: Artificial Sequence
<220> FEATURE:
<223> OTHER INFORMATION: forward primer

<400> SEQUENCE: 204
ctctgagaca gtgcttcgat gact 24

<210> SEQ ID NO 205
<211> LENGTH: 19
<212> TYPE: DNA
<213> ORGANISM: Artificial Sequence
<220> FEATURE:
<223> OTHER INFORMATION: reverse primer

<400> SEQUENCE: 205
ccatgaggcc caacttcct 19

<210> SEQ ID NO 206
<211> LENGTH: 23
<212> TYPE: DNA
<213> ORGANISM: Artificial Sequence
<220> FEATURE:
<223> OTHER INFORMATION: probe

<400> SEQUENCE: 206
cagacttggt gccctttgac tcc 23

<210> SEQ ID NO 207
<211> LENGTH: 20
<212> TYPE: DNA
<213> ORGANISM: Artificial Sequence
<220> FEATURE:
<223> OTHER INFORMATION: forward primer

<400> SEQUENCE: 207
tgtcgatgga cttccagaac 20

<210> SEQ ID NO 208
<211> LENGTH: 18
<212> TYPE: DNA
<213> ORGANISM: Artificial Sequence
<220> FEATURE:
<223> OTHER INFORMATION: probe

<400> SEQUENCE: 208
cacctgggca gctgccaa 18

<210> SEQ ID NO 209
<211> LENGTH: 19
<212> TYPE: DNA
<213> ORGANISM: Artificial Sequence
<220> FEATURE:
<223> OTHER INFORMATION: reverse primer

<400> SEQUENCE: 209
attgggacag cttggatca 19

<210> SEQ ID NO 210
<211> LENGTH: 23
<212> TYPE: DNA
<213> ORGANISM: Artificial Sequence
<220> FEATURE:
<223> OTHER INFORMATION: forward primer

<400> SEQUENCE: 210
gatctaagat ggcgactgtc gaa 23

<210> SEQ ID NO 211
<211> LENGTH: 25
<212> TYPE: DNA
<213> ORGANISM: Artificial Sequence
<220> FEATURE:
<223> OTHER INFORMATION: reverse primer

<400> SEQUENCE: 211
ttagattccg ttttctcctc ttctg 25

<210> SEQ ID NO 212
<211> LENGTH: 27
<212> TYPE: DNA
<213> ORGANISM: Artificial Sequence
<220> FEATURE:
<223> OTHER INFORMATION: probe

<400> SEQUENCE: 212
accaccccta ctcctaatcc cccgact 27

<210> SEQ ID NO 213
<211> LENGTH: 22
<212> TYPE: DNA
<213> ORGANISM: Artificial Sequence
<220> FEATURE:
<223> OTHER INFORMATION: forward primer

<400> SEQUENCE: 213
ggcagtgtca ctgagtcctt ga 22

<210> SEQ ID NO 214
<211> LENGTH: 18
<212> TYPE: DNA
<213> ORGANISM: Artificial Sequence
<220> FEATURE:
<223> OTHER INFORMATION: reverse primer

<400> SEQUENCE: 214
tgcactgtgc gtcccaat 18

<210> SEQ ID NO 215
<211> LENGTH: 18
<212> TYPE: DNA
<213> ORGANISM: Artificial Sequence
<220> FEATURE:
<223> OTHER INFORMATION: probe

<400> SEQUENCE: 215
atcctcccct gccccgcg 18

<210> SEQ ID NO 216
<211> LENGTH: 20
<212> TYPE: DNA
<213> ORGANISM: Artificial Sequence
<220> FEATURE:
<223> OTHER INFORMATION: forward primer

<400> SEQUENCE: 216
gggccctcca gaacaatgat 20

<210> SEQ ID NO 217
<211> LENGTH: 21
<212> TYPE: DNA
<213> ORGANISM: Artificial Sequence
<220> FEATURE:
<223> OTHER INFORMATION: reverse primer

<400> SEQUENCE: 217
tgcactgctt ggccttaaag a 21

<210> SEQ ID NO 218
<211> LENGTH: 25
<212> TYPE: DNA
<213> ORGANISM: Artificial Sequence
<220> FEATURE:
<223> OTHER INFORMATION: probe

<400> SEQUENCE: 218
ccgctctcat cgcagtcagg atcat 25

<210> SEQ ID NO 219
<211> LENGTH: 20
<212> TYPE: DNA

<213> ORGANISM: Artificial Sequence
<220> FEATURE:
<223> OTHER INFORMATION: forward primer

<400> SEQUENCE: 219
accgtaggct ctgctctgaa 20

<210> SEQ ID NO 220
<211> LENGTH: 20
<212> TYPE: DNA
<213> ORGANISM: Artificial Sequence
<220> FEATURE:
<223> OTHER INFORMATION: reverse primer

<400> SEQUENCE: 220
tggtccaggt ggaaaacttc 20

<210> SEQ ID NO 221
<211> LENGTH: 20
<212> TYPE: DNA
<213> ORGANISM: Artificial Sequence
<220> FEATURE:
<223> OTHER INFORMATION: probe

<400> SEQUENCE: 221
aggcagccag acccacagga 20

<210> SEQ ID NO 222
<211> LENGTH: 23
<212> TYPE: DNA
<213> ORGANISM: Artificial Sequence
<220> FEATURE:
<223> OTHER INFORMATION: forward primer

<400> SEQUENCE: 222
cggttatgtc atgccagata cac 23

<210> SEQ ID NO 223
<211> LENGTH: 25
<212> TYPE: DNA
<213> ORGANISM: Artificial Sequence
<220> FEATURE:
<223> OTHER INFORMATION: probe

<400> SEQUENCE: 223
cctcaaaggt actccctcct cccgg 25

<210> SEQ ID NO 224
<211> LENGTH: 24
<212> TYPE: DNA
<213> ORGANISM: Artificial Sequence
<220> FEATURE:
<223> OTHER INFORMATION: reverse primer

<400> SEQUENCE: 224
gaactgagac ccactgaaga aagg 24

<210> SEQ ID NO 225
<211> LENGTH: 19
<212> TYPE: DNA
<213> ORGANISM: Artificial Sequence
<220> FEATURE:
<223> OTHER INFORMATION: forward primer

<400> SEQUENCE: 225
cgtggtgccc ctctatgac 19

<210> SEQ ID NO 226
<211> LENGTH: 19
<212> TYPE: DNA
<213> ORGANISM: Artificial Sequence
<220> FEATURE:
<223> OTHER INFORMATION: probe

<400> SEQUENCE: 226
ctggagatgc tggacgccc 19

<210> SEQ ID NO 227
<211> LENGTH: 19
<212> TYPE: DNA
<213> ORGANISM: Artificial Sequence
<220> FEATURE:
<223> OTHER INFORMATION: reverse primer

<400> SEQUENCE: 227
ggctagtggg cgcatgtag 19

<210> SEQ ID NO 228
<211> LENGTH: 25
<212> TYPE: DNA
<213> ORGANISM: Artificial Sequence
<220> FEATURE:
<223> OTHER INFORMATION: reverse primer

<400> SEQUENCE: 228
ggattgtaga ctgtcaccga aattc 25

<210> SEQ ID NO 229
<211> LENGTH: 28
<212> TYPE: DNA
<213> ORGANISM: Artificial Sequence
<220> FEATURE:
<223> OTHER INFORMATION: forward primer

<400> SEQUENCE: 229
ggctattcct cattttctct acaaagtg 28

<210> SEQ ID NO 230
<211> LENGTH: 30
<212> TYPE: DNA
<213> ORGANISM: Artificial Sequence
<220> FEATURE:
<223> OTHER INFORMATION: probe

<400> SEQUENCE: 230
cctccaggag gctaccttct tcatgttcac 30

<210> SEQ ID NO 231
<211> LENGTH: 21
<212> TYPE: DNA
<213> ORGANISM: Artificial Sequence
<220> FEATURE:
<223> OTHER INFORMATION: forward primer

<400> SEQUENCE: 231
cggtagtcaa gtccggatca a 21

<210> SEQ ID NO 232
<211> LENGTH: 18
<212> TYPE: DNA
<213> ORGANISM: Artificial Sequence
<220> FEATURE:
<223> OTHER INFORMATION: reverse primer

<400> SEQUENCE: 232
gcttgccttt gcggttca 18

<210> SEQ ID NO 233
<211> LENGTH: 25
<212> TYPE: DNA
<213> ORGANISM: Artificial Sequence
<220> FEATURE:
<223> OTHER INFORMATION: probe

<400> SEQUENCE: 233
caaggagacg gaattctacc tgtgc 25

<210> SEQ ID NO 234
<211> LENGTH: 20
<212> TYPE: DNA
<213> ORGANISM: Artificial Sequence
<220> FEATURE:
<223> OTHER INFORMATION: forward primer

<400> SEQUENCE: 234
cacgggacat tcaccacatc 20

<210> SEQ ID NO 235
<211> LENGTH: 19
<212> TYPE: DNA
<213> ORGANISM: Artificial Sequence
<220> FEATURE:
<223> OTHER INFORMATION: reverse primer

<400> SEQUENCE: 235
gggtgccatc cacttcaca 19

<210> SEQ ID NO 236
<211> LENGTH: 27
<212> TYPE: DNA
<213> ORGANISM: Artificial Sequence
<220> FEATURE:
<223> OTHER INFORMATION: probe

<400> SEQUENCE: 236
ataaaaagac aaccaacggc cgactgc 27

<210> SEQ ID NO 237
<211> LENGTH: 18
<212> TYPE: DNA
<213> ORGANISM: Artificial Sequence
<220> FEATURE:
<223> OTHER INFORMATION: forward primer

<400> SEQUENCE: 237
ccagtggagc gcttccat 18

<210> SEQ ID NO 238
<211> LENGTH: 22
<212> TYPE: DNA
<213> ORGANISM: Artificial Sequence
<220> FEATURE:
<223> OTHER INFORMATION: reverse primer

<400> SEQUENCE: 238
ctctctgggt cgtctgaaac aa 22

<210> SEQ ID NO 239
<211> LENGTH: 23
<212> TYPE: DNA

<213> ORGANISM: Artificial Sequence
<220> FEATURE:
<223> OTHER INFORMATION: probe

<400> SEQUENCE: 239
tcggccactt catcaggacg cag 23

<210> SEQ ID NO 240
<211> LENGTH: 20
<212> TYPE: DNA
<213> ORGANISM: Artificial Sequence
<220> FEATURE:
<223> OTHER INFORMATION: forward primer

<400> SEQUENCE: 240
ttggtacctg tgggttagca 20

<210> SEQ ID NO 241
<211> LENGTH: 20
<212> TYPE: DNA
<213> ORGANISM: Artificial Sequence
<220> FEATURE:
<223> OTHER INFORMATION: reverse primer

<400> SEQUENCE: 241
cacatccaaa tgcaaactgg 20

<210> SEQ ID NO 242
<211> LENGTH: 26
<212> TYPE: DNA
<213> ORGANISM: Artificial Sequence
<220> FEATURE:
<223> OTHER INFORMATION: probe

<400> SEQUENCE: 242
tccccagggt agaattcaat cagagc 26

<210> SEQ ID NO 243
<211> LENGTH: 19
<212> TYPE: DNA
<213> ORGANISM: Artificial Sequence
<220> FEATURE:
<223> OTHER INFORMATION: forward primer

<400> SEQUENCE: 243
tcagcagcaa gggcatcat 19

<210> SEQ ID NO 244
<211> LENGTH: 23
<212> TYPE: DNA
<213> ORGANISM: Artificial Sequence
<220> FEATURE:
<223> OTHER INFORMATION: reverse primer

<400> SEQUENCE: 244
ggtggttttc ttgagcgtgt act 23

<210> SEQ ID NO 245
<211> LENGTH: 19
<212> TYPE: DNA
<213> ORGANISM: Artificial Sequence
<220> FEATURE:
<223> OTHER INFORMATION: probe

<400> SEQUENCE: 245
cgcccgcagg cctcatcct 19

-continued

<210> SEQ ID NO 246
<211> LENGTH: 20
<212> TYPE: DNA
<213> ORGANISM: Artificial Sequence
<220> FEATURE:
<223> OTHER INFORMATION: forward primer

<400> SEQUENCE: 246
attccaccca tggcaaattc 20

<210> SEQ ID NO 247
<211> LENGTH: 22
<212> TYPE: DNA
<213> ORGANISM: Artificial Sequence
<220> FEATURE:
<223> OTHER INFORMATION: reverse primer

<400> SEQUENCE: 247
gatgggattt ccattgatga ca 22

<210> SEQ ID NO 248
<211> LENGTH: 22
<212> TYPE: DNA
<213> ORGANISM: Artificial Sequence
<220> FEATURE:
<223> OTHER INFORMATION: probe

<400> SEQUENCE: 248
ccgttctcag ccttgacggt gc 22

<210> SEQ ID NO 249
<211> LENGTH: 23
<212> TYPE: DNA
<213> ORGANISM: Artificial Sequence
<220> FEATURE:
<223> OTHER INFORMATION: forward primer

<400> SEQUENCE: 249
caaaggagct cactgtggtg tct 23

<210> SEQ ID NO 250
<211> LENGTH: 24
<212> TYPE: DNA
<213> ORGANISM: Artificial Sequence
<220> FEATURE:
<223> OTHER INFORMATION: probe

<400> SEQUENCE: 250
tgttccaacc actgaatctg gacc 24

<210> SEQ ID NO 251
<211> LENGTH: 26
<212> TYPE: DNA
<213> ORGANISM: Artificial Sequence
<220> FEATURE:
<223> OTHER INFORMATION: reverse primer

<400> SEQUENCE: 251
gagtcagaat ggcttattca cagatg 26

<210> SEQ ID NO 252
<211> LENGTH: 20
<212> TYPE: DNA
<213> ORGANISM: Artificial Sequence
<220> FEATURE:
<223> OTHER INFORMATION: forward primer

<400> SEQUENCE: 252
ccatctgcat ccatcttgtt 20

<210> SEQ ID NO 253
<211> LENGTH: 23
<212> TYPE: DNA
<213> ORGANISM: Artificial Sequence
<220> FEATURE:
<223> OTHER INFORMATION: probe

<400> SEQUENCE: 253
ctccccaccc ttgagaagtg cct 23

<210> SEQ ID NO 254
<211> LENGTH: 20
<212> TYPE: DNA
<213> ORGANISM: Artificial Sequence
<220> FEATURE:
<223> OTHER INFORMATION: reverse primer

<400> SEQUENCE: 254
ggccaccagg gtattatctg 20

<210> SEQ ID NO 255
<211> LENGTH: 23
<212> TYPE: DNA
<213> ORGANISM: Artificial Sequence
<220> FEATURE:
<223> OTHER INFORMATION: forward primer

<400> SEQUENCE: 255
cgaaaagatg ctgaacagtg aca 23

<210> SEQ ID NO 256
<211> LENGTH: 20
<212> TYPE: DNA
<213> ORGANISM: Artificial Sequence
<220> FEATURE:
<223> OTHER INFORMATION: reverse primer

<400> SEQUENCE: 256
tcaggaacag ccaccagtga 20

<210> SEQ ID NO 257
<211> LENGTH: 28
<212> TYPE: DNA
<213> ORGANISM: Artificial Sequence
<220> FEATURE:
<223> OTHER INFORMATION: probe

<400> SEQUENCE: 257
cttcctcctc ccttctggtc agttggat 28

<210> SEQ ID NO 258
<211> LENGTH: 20
<212> TYPE: DNA
<213> ORGANISM: Artificial Sequence
<220> FEATURE:
<223> OTHER INFORMATION: reverse primer

<400> SEQUENCE: 258
ggcccagctt gaatttttca 20

<210> SEQ ID NO 259
<211> LENGTH: 27
<212> TYPE: DNA

<213> ORGANISM: Artificial Sequence
<220> FEATURE:
<223> OTHER INFORMATION: forward primer

<400> SEQUENCE: 259
aagctatgag gaaaagaagt acacgat 27

<210> SEQ ID NO 260
<211> LENGTH: 30
<212> TYPE: DNA
<213> ORGANISM: Artificial Sequence
<220> FEATURE:
<223> OTHER INFORMATION: probe

<400> SEQUENCE: 260
tcagccactg gcttctgtca taatcaggag 30

<210> SEQ ID NO 261
<211> LENGTH: 20
<212> TYPE: DNA
<213> ORGANISM: Artificial Sequence
<220> FEATURE:
<223> OTHER INFORMATION: forward primer

<400> SEQUENCE: 261
cccactcagt agccaagtca 20

<210> SEQ ID NO 262
<211> LENGTH: 27
<212> TYPE: DNA
<213> ORGANISM: Artificial Sequence
<220> FEATURE:
<223> OTHER INFORMATION: probe

<400> SEQUENCE: 262
tcaagtaaac gggctgtttt ccaaaca 27

<210> SEQ ID NO 263
<211> LENGTH: 20
<212> TYPE: DNA
<213> ORGANISM: Artificial Sequence
<220> FEATURE:
<223> OTHER INFORMATION: reverse primer

<400> SEQUENCE: 263
cacgcaggtg gtatcagtct 20

<210> SEQ ID NO 264
<211> LENGTH: 20
<212> TYPE: DNA
<213> ORGANISM: Artificial Sequence
<220> FEATURE:
<223> OTHER INFORMATION: forward primer

<400> SEQUENCE: 264
cggtgtgaga agtgcagcaa 20

<210> SEQ ID NO 265
<211> LENGTH: 24
<212> TYPE: DNA
<213> ORGANISM: Artificial Sequence
<220> FEATURE:
<223> OTHER INFORMATION: probe

<400> SEQUENCE: 265
ccagaccata gcacactcgg gcac 24

-continued

<210> SEQ ID NO 266
<211> LENGTH: 19
<212> TYPE: DNA
<213> ORGANISM: Artificial Sequence
<220> FEATURE:
<223> OTHER INFORMATION: reverse primer

<400> SEQUENCE: 266
cctctcgcaa gtgctccat 19

<210> SEQ ID NO 267
<211> LENGTH: 24
<212> TYPE: DNA
<213> ORGANISM: Artificial Sequence
<220> FEATURE:
<223> OTHER INFORMATION: forward primer

<400> SEQUENCE: 267
tgaacataaa gtctgcaaca tgga 24

<210> SEQ ID NO 268
<211> LENGTH: 28
<212> TYPE: DNA
<213> ORGANISM: Artificial Sequence
<220> FEATURE:
<223> OTHER INFORMATION: reverse primer

<400> SEQUENCE: 268
tgaggttggt tactgttggt atcatata 28

<210> SEQ ID NO 269
<211> LENGTH: 24
<212> TYPE: DNA
<213> ORGANISM: Artificial Sequence
<220> FEATURE:
<223> OTHER INFORMATION: probe

<400> SEQUENCE: 269
ttgcactgca caggccacat tcac 24

<210> SEQ ID NO 270
<211> LENGTH: 24
<212> TYPE: DNA
<213> ORGANISM: Artificial Sequence
<220> FEATURE:
<223> OTHER INFORMATION: forward primer

<400> SEQUENCE: 270
tccaggatgt taggaactgt gaag 24

<210> SEQ ID NO 271
<211> LENGTH: 22
<212> TYPE: DNA
<213> ORGANISM: Artificial Sequence
<220> FEATURE:
<223> OTHER INFORMATION: reverse primer

<400> SEQUENCE: 271
gcgtgtctgc gtagtagctg tt 22

<210> SEQ ID NO 272
<211> LENGTH: 24
<212> TYPE: DNA
<213> ORGANISM: Artificial Sequence
<220> FEATURE:
<223> OTHER INFORMATION: probe

<400> SEQUENCE: 272
agtcgctggt ttcatgccct tcca 24

<210> SEQ ID NO 273
<211> LENGTH: 19
<212> TYPE: DNA
<213> ORGANISM: Artificial Sequence
<220> FEATURE:
<223> OTHER INFORMATION: forward primer

<400> SEQUENCE: 273
agaaccgcaa ggtgagcaa 19

<210> SEQ ID NO 274
<211> LENGTH: 21
<212> TYPE: DNA
<213> ORGANISM: Artificial Sequence
<220> FEATURE:
<223> OTHER INFORMATION: reverse primer

<400> SEQUENCE: 274
tccaactgaa ggtccctgat g 21

<210> SEQ ID NO 275
<211> LENGTH: 26
<212> TYPE: DNA
<213> ORGANISM: Artificial Sequence
<220> FEATURE:
<223> OTHER INFORMATION: probe

<400> SEQUENCE: 275
tggagattct ccagcacgtc atcgac 26

<210> SEQ ID NO 276
<211> LENGTH: 21
<212> TYPE: DNA
<213> ORGANISM: Artificial Sequence
<220> FEATURE:
<223> OTHER INFORMATION: forward primer

<400> SEQUENCE: 276
tccggagctg tgatctaagg a 21

<210> SEQ ID NO 277
<211> LENGTH: 24
<212> TYPE: DNA
<213> ORGANISM: Artificial Sequence
<220> FEATURE:
<223> OTHER INFORMATION: probe

<400> SEQUENCE: 277
tgtattgcgc acccctcaag cctg 24

<210> SEQ ID NO 278
<211> LENGTH: 20
<212> TYPE: DNA
<213> ORGANISM: Artificial Sequence
<220> FEATURE:
<223> OTHER INFORMATION: reverse primer

<400> SEQUENCE: 278
cggacagagc gagctgactt 20

<210> SEQ ID NO 279
<211> LENGTH: 21
<212> TYPE: DNA

<213> ORGANISM: Artificial Sequence
<220> FEATURE:
<223> OTHER INFORMATION: forward primer

<400> SEQUENCE: 279
gcatggtagc cgaagatttc a 21

<210> SEQ ID NO 280
<211> LENGTH: 30
<212> TYPE: DNA
<213> ORGANISM: Artificial Sequence
<220> FEATURE:
<223> OTHER INFORMATION: reverse primer

<400> SEQUENCE: 280
tttccggtaa tagtctgtct catagatatc 30

<210> SEQ ID NO 281
<211> LENGTH: 28
<212> TYPE: DNA
<213> ORGANISM: Artificial Sequence
<220> FEATURE:
<223> OTHER INFORMATION: probe

<400> SEQUENCE: 281
cgcgtcatac caaaatctcc gattttga 28

<210> SEQ ID NO 282
<211> LENGTH: 19
<212> TYPE: DNA
<213> ORGANISM: Artificial Sequence
<220> FEATURE:
<223> OTHER INFORMATION: forward primer

<400> SEQUENCE: 282
gtggacagca ccatgaaca 19

<210> SEQ ID NO 283
<211> LENGTH: 20
<212> TYPE: DNA
<213> ORGANISM: Artificial Sequence
<220> FEATURE:
<223> OTHER INFORMATION: reverse primer

<400> SEQUENCE: 283
ccttcatacc cgacttgagg 20

<210> SEQ ID NO 284
<211> LENGTH: 20
<212> TYPE: DNA
<213> ORGANISM: Artificial Sequence
<220> FEATURE:
<223> OTHER INFORMATION: probe

<400> SEQUENCE: 284
cttccggcca gcactgcctc 20

<210> SEQ ID NO 285
<211> LENGTH: 20
<212> TYPE: DNA
<213> ORGANISM: Artificial Sequence
<220> FEATURE:
<223> OTHER INFORMATION: forward primer

<400> SEQUENCE: 285
cctgaacctt ccaaagatgg 20

<210> SEQ ID NO 286
<211> LENGTH: 20
<212> TYPE: DNA
<213> ORGANISM: Artificial Sequence
<220> FEATURE:
<223> OTHER INFORMATION: reverse primer

<400> SEQUENCE: 286
accaggcaag tctcctcatt 20

<210> SEQ ID NO 287
<211> LENGTH: 27
<212> TYPE: DNA
<213> ORGANISM: Artificial Sequence
<220> FEATURE:
<223> OTHER INFORMATION: probe

<400> SEQUENCE: 287
ccagattgga agcatccatc tttttca 27

<210> SEQ ID NO 288
<211> LENGTH: 20
<212> TYPE: DNA
<213> ORGANISM: Artificial Sequence
<220> FEATURE:
<223> OTHER INFORMATION: forward primer

<400> SEQUENCE: 288
ccacagctca ccttctgtca 20

<210> SEQ ID NO 289
<211> LENGTH: 20
<212> TYPE: DNA
<213> ORGANISM: Artificial Sequence
<220> FEATURE:
<223> OTHER INFORMATION: reverse primer

<400> SEQUENCE: 289
cctcagtgcc agtctcttcc 20

<210> SEQ ID NO 290
<211> LENGTH: 20
<212> TYPE: DNA
<213> ORGANISM: Artificial Sequence
<220> FEATURE:
<223> OTHER INFORMATION: probe

<400> SEQUENCE: 290
tccatcccag ctccagccag 20

<210> SEQ ID NO 291
<211> LENGTH: 23
<212> TYPE: DNA
<213> ORGANISM: Artificial Sequence
<220> FEATURE:
<223> OTHER INFORMATION: probe

<400> SEQUENCE: 291
ccacttgtcg aaccaccgct cgt 23

<210> SEQ ID NO 292
<211> LENGTH: 19
<212> TYPE: DNA
<213> ORGANISM: Artificial Sequence
<220> FEATURE:
<223> OTHER INFORMATION: forward primer

<400> SEQUENCE: 292
cggactttgg gtgcgactt 19

<210> SEQ ID NO 293
<211> LENGTH: 24
<212> TYPE: DNA
<213> ORGANISM: Artificial Sequence
<220> FEATURE:
<223> OTHER INFORMATION: reverse primer

<400> SEQUENCE: 293
ttacaactct tccactggga cgat 24

<210> SEQ ID NO 294
<211> LENGTH: 18
<212> TYPE: DNA
<213> ORGANISM: Artificial Sequence
<220> FEATURE:
<223> OTHER INFORMATION: forward primer

<400> SEQUENCE: 294
gcccagaggc tccatcgt 18

<210> SEQ ID NO 295
<211> LENGTH: 23
<212> TYPE: DNA
<213> ORGANISM: Artificial Sequence
<220> FEATURE:
<223> OTHER INFORMATION: reverse primer

<400> SEQUENCE: 295
cagaggtttg aacagtgcag aca 23

<210> SEQ ID NO 296
<211> LENGTH: 23
<212> TYPE: DNA
<213> ORGANISM: Artificial Sequence
<220> FEATURE:
<223> OTHER INFORMATION: probe

<400> SEQUENCE: 296
cctcttcctc cccagtcggc tga 23

<210> SEQ ID NO 297
<211> LENGTH: 20
<212> TYPE: DNA
<213> ORGANISM: Artificial Sequence
<220> FEATURE:
<223> OTHER INFORMATION: forward primer

<400> SEQUENCE: 297
ggcctgctga gatcaaagac 20

<210> SEQ ID NO 298
<211> LENGTH: 20
<212> TYPE: DNA
<213> ORGANISM: Artificial Sequence
<220> FEATURE:
<223> OTHER INFORMATION: reverse primer

<400> SEQUENCE: 298
gtccactgtg gctgtgagaa 20

<210> SEQ ID NO 299
<211> LENGTH: 26
<212> TYPE: DNA

<213> ORGANISM: Artificial Sequence
<220> FEATURE:
<223> OTHER INFORMATION: probe

<400> SEQUENCE: 299
tgttcctcag gtcctcaatg gtcttg 26

<210> SEQ ID NO 300
<211> LENGTH: 21
<212> TYPE: DNA
<213> ORGANISM: Artificial Sequence
<220> FEATURE:
<223> OTHER INFORMATION: forward primer

<400> SEQUENCE: 300
cgaggattgg ttcttcagca a 21

<210> SEQ ID NO 301
<211> LENGTH: 22
<212> TYPE: DNA
<213> ORGANISM: Artificial Sequence
<220> FEATURE:
<223> OTHER INFORMATION: reverse primer

<400> SEQUENCE: 301
actctgcacc agctcactgt tg 22

<210> SEQ ID NO 302
<211> LENGTH: 24
<212> TYPE: DNA
<213> ORGANISM: Artificial Sequence
<220> FEATURE:
<223> OTHER INFORMATION: probe

<400> SEQUENCE: 302
cacctcgcgg ttcagttcct ctgt 24

<210> SEQ ID NO 303
<211> LENGTH: 20
<212> TYPE: DNA
<213> ORGANISM: Artificial Sequence
<220> FEATURE:
<223> OTHER INFORMATION: forward primer

<400> SEQUENCE: 303
agagatcgag gctctcaagg 20

<210> SEQ ID NO 304
<211> LENGTH: 20
<212> TYPE: DNA
<213> ORGANISM: Artificial Sequence
<220> FEATURE:
<223> OTHER INFORMATION: reverse primer

<400> SEQUENCE: 304
ggccttttac ttcctcttcg 20

<210> SEQ ID NO 305
<211> LENGTH: 27
<212> TYPE: DNA
<213> ORGANISM: Artificial Sequence
<220> FEATURE:
<223> OTHER INFORMATION: probe

<400> SEQUENCE: 305
tggttcttct tcatgaagag cagctcc 27

<210> SEQ ID NO 306
<211> LENGTH: 21
<212> TYPE: DNA
<213> ORGANISM: Artificial Sequence
<220> FEATURE:
<223> OTHER INFORMATION: forward primer

<400> SEQUENCE: 306
tgagcggcag aatcaggagt a 21

<210> SEQ ID NO 307
<211> LENGTH: 19
<212> TYPE: DNA
<213> ORGANISM: Artificial Sequence
<220> FEATURE:
<223> OTHER INFORMATION: reverse primer

<400> SEQUENCE: 307
tgcggtaggt ggcaatctc 19

<210> SEQ ID NO 308
<211> LENGTH: 24
<212> TYPE: DNA
<213> ORGANISM: Artificial Sequence
<220> FEATURE:
<223> OTHER INFORMATION: probe

<400> SEQUENCE: 308
ctcatggaca tcaagtcgcg gctg 24

<210> SEQ ID NO 309
<211> LENGTH: 20
<212> TYPE: DNA
<213> ORGANISM: Artificial Sequence
<220> FEATURE:
<223> OTHER INFORMATION: forward primer

<400> SEQUENCE: 309
tcagtggaga aggagttgga 20

<210> SEQ ID NO 310
<211> LENGTH: 28
<212> TYPE: DNA
<213> ORGANISM: Artificial Sequence
<220> FEATURE:
<223> OTHER INFORMATION: probe

<400> SEQUENCE: 310
ccagtcaaca tctctgttgt cacaagca 28

<210> SEQ ID NO 311
<211> LENGTH: 20
<212> TYPE: DNA
<213> ORGANISM: Artificial Sequence
<220> FEATURE:
<223> OTHER INFORMATION: reverse primer

<400> SEQUENCE: 311
tgccatatcc agaggaaaca 20

<210> SEQ ID NO 312
<211> LENGTH: 27
<212> TYPE: DNA
<213> ORGANISM: Artificial Sequence
<220> FEATURE:
<223> OTHER INFORMATION: forward primer

<400> SEQUENCE: 312
ggatgaagct tacatgaaca aggtaga 27

<210> SEQ ID NO 313
<211> LENGTH: 25
<212> TYPE: DNA
<213> ORGANISM: Artificial Sequence
<220> FEATURE:
<223> OTHER INFORMATION: reverse primer

<400> SEQUENCE: 313
catatagctg cctgaggaag ttgat 25

<210> SEQ ID NO 314
<211> LENGTH: 21
<212> TYPE: DNA
<213> ORGANISM: Artificial Sequence
<220> FEATURE:
<223> OTHER INFORMATION: probe

<400> SEQUENCE: 314
cgtcggtcag cccttccagg c 21

<210> SEQ ID NO 315
<211> LENGTH: 22
<212> TYPE: DNA
<213> ORGANISM: Artificial Sequence
<220> FEATURE:
<223> OTHER INFORMATION: forward primer

<400> SEQUENCE: 315
ggaaagacca cctgaaaaac ca 22

<210> SEQ ID NO 316
<211> LENGTH: 24
<212> TYPE: DNA
<213> ORGANISM: Artificial Sequence
<220> FEATURE:
<223> OTHER INFORMATION: reverse primer

<400> SEQUENCE: 316
gtacttcttc ccacactcct caca 24

<210> SEQ ID NO 317
<211> LENGTH: 23
<212> TYPE: DNA
<213> ORGANISM: Artificial Sequence
<220> FEATURE:
<223> OTHER INFORMATION: probe

<400> SEQUENCE: 317
acccacgacc ccaacaaaat ggc 23

<210> SEQ ID NO 318
<211> LENGTH: 23
<212> TYPE: DNA
<213> ORGANISM: Artificial Sequence
<220> FEATURE:
<223> OTHER INFORMATION: forward primer

<400> SEQUENCE: 318
cagatggcca ctttgagaac att 23

<210> SEQ ID NO 319
<211> LENGTH: 22
<212> TYPE: DNA

<213> ORGANISM: Artificial Sequence
<220> FEATURE:
<223> OTHER INFORMATION: reverse primer

<400> SEQUENCE: 319
ggcagcatta accacaagga tt 22

<210> SEQ ID NO 320
<211> LENGTH: 28
<212> TYPE: DNA
<213> ORGANISM: Artificial Sequence
<220> FEATURE:
<223> OTHER INFORMATION: probe

<400> SEQUENCE: 320
agctgacaac agtgtgaacg accagacc 28

<210> SEQ ID NO 321
<211> LENGTH: 21
<212> TYPE: DNA
<213> ORGANISM: Artificial Sequence
<220> FEATURE:
<223> OTHER INFORMATION: forward primer

<400> SEQUENCE: 321
gacttttgcc cgctaccttt c 21

<210> SEQ ID NO 322
<211> LENGTH: 26
<212> TYPE: DNA
<213> ORGANISM: Artificial Sequence
<220> FEATURE:
<223> OTHER INFORMATION: reverse primer

<400> SEQUENCE: 322
gccactaact gcttcagtat gaagag 26

<210> SEQ ID NO 323
<211> LENGTH: 24
<212> TYPE: DNA
<213> ORGANISM: Artificial Sequence
<220> FEATURE:
<223> OTHER INFORMATION: probe

<400> SEQUENCE: 323
acagctcatt gttgtcacgc cgga 24

<210> SEQ ID NO 324
<211> LENGTH: 20
<212> TYPE: DNA
<213> ORGANISM: Artificial Sequence
<220> FEATURE:
<223> OTHER INFORMATION: forward primer

<400> SEQUENCE: 324
ggagaacaat ccccttgaga 20

<210> SEQ ID NO 325
<211> LENGTH: 20
<212> TYPE: DNA
<213> ORGANISM: Artificial Sequence
<220> FEATURE:
<223> OTHER INFORMATION: reverse primer

<400> SEQUENCE: 325
atctcctgga tggtgatggt 20

-continued

<210> SEQ ID NO 326
<211> LENGTH: 27
<212> TYPE: DNA
<213> ORGANISM: Artificial Sequence
<220> FEATURE:
<223> OTHER INFORMATION: probe

<400> SEQUENCE: 326
tggcctttct gtctacaagg atcacca 27

<210> SEQ ID NO 327
<211> LENGTH: 24
<212> TYPE: DNA
<213> ORGANISM: Artificial Sequence
<220> FEATURE:
<223> OTHER INFORMATION: forward primer

<400> SEQUENCE: 327
tgatggtcct atgtgtcaca ttca 24

<210> SEQ ID NO 328
<211> LENGTH: 20
<212> TYPE: DNA
<213> ORGANISM: Artificial Sequence
<220> FEATURE:
<223> OTHER INFORMATION: reverse primer

<400> SEQUENCE: 328
tgggacagga aacacaccaa 20

<210> SEQ ID NO 329
<211> LENGTH: 30
<212> TYPE: DNA
<213> ORGANISM: Artificial Sequence
<220> FEATURE:
<223> OTHER INFORMATION: probe

<400> SEQUENCE: 329
caggtttcat accaacacag gcttcagcac 30

<210> SEQ ID NO 330
<211> LENGTH: 19
<212> TYPE: DNA
<213> ORGANISM: Artificial Sequence
<220> FEATURE:
<223> OTHER INFORMATION: forward primer

<400> SEQUENCE: 330
ctacagggac gccatcgaa 19

<210> SEQ ID NO 331
<211> LENGTH: 23
<212> TYPE: DNA
<213> ORGANISM: Artificial Sequence
<220> FEATURE:
<223> OTHER INFORMATION: reverse primer

<400> SEQUENCE: 331
atccaaccaa tcacctgaat gtt 23

<210> SEQ ID NO 332
<211> LENGTH: 23
<212> TYPE: DNA
<213> ORGANISM: Artificial Sequence
<220> FEATURE:
<223> OTHER INFORMATION: probe

<400> SEQUENCE: 332
cttacaccag catcaagatc cgg 23

<210> SEQ ID NO 333
<211> LENGTH: 20
<212> TYPE: DNA
<213> ORGANISM: Artificial Sequence
<220> FEATURE:
<223> OTHER INFORMATION: forward primer

<400> SEQUENCE: 333
gagaaccaat ctcaccgaca 20

<210> SEQ ID NO 334
<211> LENGTH: 20
<212> TYPE: DNA
<213> ORGANISM: Artificial Sequence
<220> FEATURE:
<223> OTHER INFORMATION: reverse primer

<400> SEQUENCE: 334
cacccgagtg taaccatagc 20

<210> SEQ ID NO 335
<211> LENGTH: 24
<212> TYPE: DNA
<213> ORGANISM: Artificial Sequence
<220> FEATURE:
<223> OTHER INFORMATION: probe

<400> SEQUENCE: 335
acaggtattc ctctgccagc tgcc 24

<210> SEQ ID NO 336
<211> LENGTH: 19
<212> TYPE: DNA
<213> ORGANISM: Artificial Sequence
<220> FEATURE:
<223> OTHER INFORMATION: forward primer

<400> SEQUENCE: 336
ccgccctcac ctgaagaga 19

<210> SEQ ID NO 337
<211> LENGTH: 22
<212> TYPE: DNA
<213> ORGANISM: Artificial Sequence
<220> FEATURE:
<223> OTHER INFORMATION: reverse primer

<400> SEQUENCE: 337
ggaataagtt agccgcgctt ct 22

<210> SEQ ID NO 338
<211> LENGTH: 21
<212> TYPE: DNA
<213> ORGANISM: Artificial Sequence
<220> FEATURE:
<223> OTHER INFORMATION: probe

<400> SEQUENCE: 338
cccagtgtcc gccaaggagc g 21

<210> SEQ ID NO 339
<211> LENGTH: 18
<212> TYPE: DNA

<213> ORGANISM: Artificial Sequence
<220> FEATURE:
<223> OTHER INFORMATION: forward primer

<400> SEQUENCE: 339
gccgagatcg ccaagatg 18

<210> SEQ ID NO 340
<211> LENGTH: 27
<212> TYPE: DNA
<213> ORGANISM: Artificial Sequence
<220> FEATURE:
<223> OTHER INFORMATION: reverse primer

<400> SEQUENCE: 340
cttttgatgg tagagttcca gtgattc 27

<210> SEQ ID NO 341
<211> LENGTH: 24
<212> TYPE: DNA
<213> ORGANISM: Artificial Sequence
<220> FEATURE:
<223> OTHER INFORMATION: probe

<400> SEQUENCE: 341
cagcattgtc tgtcctccct ggca 24

<210> SEQ ID NO 342
<211> LENGTH: 19
<212> TYPE: DNA
<213> ORGANISM: Artificial Sequence
<220> FEATURE:
<223> OTHER INFORMATION: forward primer

<400> SEQUENCE: 342
ccctcgtgct gatgctact 19

<210> SEQ ID NO 343
<211> LENGTH: 22
<212> TYPE: DNA
<213> ORGANISM: Artificial Sequence
<220> FEATURE:
<223> OTHER INFORMATION: reverse primer

<400> SEQUENCE: 343
catcatgacc tggtcttcta gg 22

<210> SEQ ID NO 344
<211> LENGTH: 22
<212> TYPE: DNA
<213> ORGANISM: Artificial Sequence
<220> FEATURE:
<223> OTHER INFORMATION: probe

<400> SEQUENCE: 344
ctgccctaga cgctggctcc tc 22

<210> SEQ ID NO 345
<211> LENGTH: 21
<212> TYPE: DNA
<213> ORGANISM: Artificial Sequence
<220> FEATURE:
<223> OTHER INFORMATION: forward primer

<400> SEQUENCE: 345
cggtggacca cgaagagtta a 21

<210> SEQ ID NO 346
<211> LENGTH: 23
<212> TYPE: DNA
<213> ORGANISM: Artificial Sequence
<220> FEATURE:
<223> OTHER INFORMATION: probe

<400> SEQUENCE: 346
ccgggacttg gagaagcact gca 23

<210> SEQ ID NO 347
<211> LENGTH: 19
<212> TYPE: DNA
<213> ORGANISM: Artificial Sequence
<220> FEATURE:
<223> OTHER INFORMATION: reverse primer

<400> SEQUENCE: 347
ggctcgcctc ttccatgtc 19

<210> SEQ ID NO 348
<211> LENGTH: 20
<212> TYPE: DNA
<213> ORGANISM: Artificial Sequence
<220> FEATURE:
<223> OTHER INFORMATION: forward primer

<400> SEQUENCE: 348
ctttgaaccc ttgcttgcaa 20

<210> SEQ ID NO 349
<211> LENGTH: 25
<212> TYPE: DNA
<213> ORGANISM: Artificial Sequence
<220> FEATURE:
<223> OTHER INFORMATION: probe

<400> SEQUENCE: 349
aagtcctggg tgcttctgac gcaca 25

<210> SEQ ID NO 350
<211> LENGTH: 18
<212> TYPE: DNA
<213> ORGANISM: Artificial Sequence
<220> FEATURE:
<223> OTHER INFORMATION: reverse primer

<400> SEQUENCE: 350
cccgggacaa agcaaatg 18

<210> SEQ ID NO 351
<211> LENGTH: 19
<212> TYPE: DNA
<213> ORGANISM: Artificial Sequence
<220> FEATURE:
<223> OTHER INFORMATION: forward primer

<400> SEQUENCE: 351
ccgcaacgtg gttttctca 19

<210> SEQ ID NO 352
<211> LENGTH: 22
<212> TYPE: DNA
<213> ORGANISM: Artificial Sequence
<220> FEATURE:
<223> OTHER INFORMATION: probe

<400> SEQUENCE: 352
ctcggtgttg gccatgctcc ag 22

<210> SEQ ID NO 353
<211> LENGTH: 21
<212> TYPE: DNA
<213> ORGANISM: Artificial Sequence
<220> FEATURE:
<223> OTHER INFORMATION: reverse primer

<400> SEQUENCE: 353
tgctgggttt ctcctcctgt t 21

<210> SEQ ID NO 354
<211> LENGTH: 20
<212> TYPE: DNA
<213> ORGANISM: Artificial Sequence
<220> FEATURE:
<223> OTHER INFORMATION: forward primer

<400> SEQUENCE: 354
ccagctctcc ttccagctac 20

<210> SEQ ID NO 355
<211> LENGTH: 20
<212> TYPE: DNA
<213> ORGANISM: Artificial Sequence
<220> FEATURE:
<223> OTHER INFORMATION: reverse primer

<400> SEQUENCE: 355
gggtggctct cacttagctc 20

<210> SEQ ID NO 356
<211> LENGTH: 24
<212> TYPE: DNA
<213> ORGANISM: Artificial Sequence
<220> FEATURE:
<223> OTHER INFORMATION: probe

<400> SEQUENCE: 356
atcaatgtcc ctgtccgagt gctg 24

<210> SEQ ID NO 357
<211> LENGTH: 23
<212> TYPE: DNA
<213> ORGANISM: Artificial Sequence
<220> FEATURE:
<223> OTHER INFORMATION: reverse primer

<400> SEQUENCE: 357
cacactagca ttttctccgc ata 23

<210> SEQ ID NO 358
<211> LENGTH: 21
<212> TYPE: DNA
<213> ORGANISM: Artificial Sequence
<220> FEATURE:
<223> OTHER INFORMATION: forward primer

<400> SEQUENCE: 358
ataccaatca ccgcacaaac c 21

<210> SEQ ID NO 359
<211> LENGTH: 30
<212> TYPE: DNA

<213> ORGANISM: Artificial Sequence
<220> FEATURE:
<223> OTHER INFORMATION: probe

<400> SEQUENCE: 359
tgcgctgtga ctggacttaa caaatagcct 30

<210> SEQ ID NO 360
<211> LENGTH: 18
<212> TYPE: DNA
<213> ORGANISM: Artificial Sequence
<220> FEATURE:
<223> OTHER INFORMATION: forward primer

<400> SEQUENCE: 360
gccatccgca aaggcttt 18

<210> SEQ ID NO 361
<211> LENGTH: 18
<212> TYPE: DNA
<213> ORGANISM: Artificial Sequence
<220> FEATURE:
<223> OTHER INFORMATION: reverse primer

<400> SEQUENCE: 361
ggccattccg ccagtttc 18

<210> SEQ ID NO 362
<211> LENGTH: 23
<212> TYPE: DNA
<213> ORGANISM: Artificial Sequence
<220> FEATURE:
<223> OTHER INFORMATION: probe

<400> SEQUENCE: 362
tcgcttgtca ccttgccatg tgg 23

<210> SEQ ID NO 363
<211> LENGTH: 20
<212> TYPE: DNA
<213> ORGANISM: Artificial Sequence
<220> FEATURE:
<223> OTHER INFORMATION: forward primer

<400> SEQUENCE: 363
gcatcaggct gtcattatgg 20

<210> SEQ ID NO 364
<211> LENGTH: 20
<212> TYPE: DNA
<213> ORGANISM: Artificial Sequence
<220> FEATURE:
<223> OTHER INFORMATION: reverse primer

<400> SEQUENCE: 364
agtagttgtg ctgcccttcc 20

<210> SEQ ID NO 365
<211> LENGTH: 28
<212> TYPE: DNA
<213> ORGANISM: Artificial Sequence
<220> FEATURE:
<223> OTHER INFORMATION: probe

<400> SEQUENCE: 365
tgtccttacc tgtgggagct gtaaggtc 28

<210> SEQ ID NO 366
<211> LENGTH: 23
<212> TYPE: DNA
<213> ORGANISM: Artificial Sequence
<220> FEATURE:
<223> OTHER INFORMATION: forward primer

<400> SEQUENCE: 366
tctccatatc tgccttgcag agt 23

<210> SEQ ID NO 367
<211> LENGTH: 19
<212> TYPE: DNA
<213> ORGANISM: Artificial Sequence
<220> FEATURE:
<223> OTHER INFORMATION: reverse primer

<400> SEQUENCE: 367
gcacgtgggt cagattgct 19

<210> SEQ ID NO 368
<211> LENGTH: 22
<212> TYPE: DNA
<213> ORGANISM: Artificial Sequence
<220> FEATURE:
<223> OTHER INFORMATION: probe

<400> SEQUENCE: 368
tcctgcagca cctcatcggg ct 22

<210> SEQ ID NO 369
<211> LENGTH: 19
<212> TYPE: DNA
<213> ORGANISM: Artificial Sequence
<220> FEATURE:
<223> OTHER INFORMATION: forward primer

<400> SEQUENCE: 369
gccctcccag tgtgcaaat 19

<210> SEQ ID NO 370
<211> LENGTH: 23
<212> TYPE: DNA
<213> ORGANISM: Artificial Sequence
<220> FEATURE:
<223> OTHER INFORMATION: probe

<400> SEQUENCE: 370
tgctgtttcg acgacaccgt tcg 23

<210> SEQ ID NO 371
<211> LENGTH: 25
<212> TYPE: DNA
<213> ORGANISM: Artificial Sequence
<220> FEATURE:
<223> OTHER INFORMATION: reverse primer

<400> SEQUENCE: 371
cgtcgatggt attaggatag aagca 25

<210> SEQ ID NO 372
<211> LENGTH: 24
<212> TYPE: DNA
<213> ORGANISM: Artificial Sequence
<220> FEATURE:
<223> OTHER INFORMATION: forward primer

<400> SEQUENCE: 372
gaacttcttg agcaggagca tacc 24

<210> SEQ ID NO 373
<211> LENGTH: 25
<212> TYPE: DNA
<213> ORGANISM: Artificial Sequence
<220> FEATURE:
<223> OTHER INFORMATION: reverse primer

<400> SEQUENCE: 373
tccaccccca agaatatcat ctagt 25

<210> SEQ ID NO 374
<211> LENGTH: 25
<212> TYPE: DNA
<213> ORGANISM: Artificial Sequence
<220> FEATURE:
<223> OTHER INFORMATION: probe

<400> SEQUENCE: 374
agggcttcat aatcaccttc tgttc 25

<210> SEQ ID NO 375
<211> LENGTH: 20
<212> TYPE: DNA
<213> ORGANISM: Artificial Sequence
<220> FEATURE:
<223> OTHER INFORMATION: forward primer

<400> SEQUENCE: 375
cgaagccctt acaagtttcc 20

<210> SEQ ID NO 376
<211> LENGTH: 20
<212> TYPE: DNA
<213> ORGANISM: Artificial Sequence
<220> FEATURE:
<223> OTHER INFORMATION: reverse primer

<400> SEQUENCE: 376
ggactcttca ggggtgaaat 20

<210> SEQ ID NO 377
<211> LENGTH: 24
<212> TYPE: DNA
<213> ORGANISM: Artificial Sequence
<220> FEATURE:
<223> OTHER INFORMATION: probe

<400> SEQUENCE: 377
cccttacgga ttcctggagg gaac 24

<210> SEQ ID NO 378
<211> LENGTH: 20
<212> TYPE: DNA
<213> ORGANISM: Artificial Sequence
<220> FEATURE:
<223> OTHER INFORMATION: forward primer

<400> SEQUENCE: 378
ccagacgagc gattagaagc 20

<210> SEQ ID NO 379
<211> LENGTH: 20
<212> TYPE: DNA

<213> ORGANISM: Artificial Sequence
<220> FEATURE:
<223> OTHER INFORMATION: reverse primer

<400> SEQUENCE: 379
tcctcctctt cctcctcctc 20

<210> SEQ ID NO 380
<211> LENGTH: 23
<212> TYPE: DNA
<213> ORGANISM: Artificial Sequence
<220> FEATURE:
<223> OTHER INFORMATION: probe

<400> SEQUENCE: 380
tgtgaggtga atgatttggg gga 23

<210> SEQ ID NO 381
<211> LENGTH: 20
<212> TYPE: DNA
<213> ORGANISM: Artificial Sequence
<220> FEATURE:
<223> OTHER INFORMATION: forward primer

<400> SEQUENCE: 381
catcttccag gaggaccact 20

<210> SEQ ID NO 382
<211> LENGTH: 20
<212> TYPE: DNA
<213> ORGANISM: Artificial Sequence
<220> FEATURE:
<223> OTHER INFORMATION: reverse primer

<400> SEQUENCE: 382
tccgaccttc aatcatttca 20

<210> SEQ ID NO 383
<211> LENGTH: 24
<212> TYPE: DNA
<213> ORGANISM: Artificial Sequence
<220> FEATURE:
<223> OTHER INFORMATION: probe

<400> SEQUENCE: 383
ctctgtggca ccctggacta cctg 24

<210> SEQ ID NO 384
<211> LENGTH: 20
<212> TYPE: DNA
<213> ORGANISM: Artificial Sequence
<220> FEATURE:
<223> OTHER INFORMATION: forward primer

<400> SEQUENCE: 384
cctggaggct gcaacatacc 20

<210> SEQ ID NO 385
<211> LENGTH: 23
<212> TYPE: DNA
<213> ORGANISM: Artificial Sequence
<220> FEATURE:
<223> OTHER INFORMATION: reverse primer

<400> SEQUENCE: 385
tacaatggct ttggaggata gca 23

<210> SEQ ID NO 386
<211> LENGTH: 25
<212> TYPE: DNA
<213> ORGANISM: Artificial Sequence
<220> FEATURE:
<223> OTHER INFORMATION: probe

<400> SEQUENCE: 386
atcctcctga agcccttttc gcagc 25

<210> SEQ ID NO 387
<211> LENGTH: 20
<212> TYPE: DNA
<213> ORGANISM: Artificial Sequence
<220> FEATURE:
<223> OTHER INFORMATION: forward primer

<400> SEQUENCE: 387
tgttttgatt cccgggctta 20

<210> SEQ ID NO 388
<211> LENGTH: 28
<212> TYPE: DNA
<213> ORGANISM: Artificial Sequence
<220> FEATURE:
<223> OTHER INFORMATION: probe

<400> SEQUENCE: 388
tgccttcttc ctccctcact tctcacct 28

<210> SEQ ID NO 389
<211> LENGTH: 24
<212> TYPE: DNA
<213> ORGANISM: Artificial Sequence
<220> FEATURE:
<223> OTHER INFORMATION: reverse primer

<400> SEQUENCE: 389
caaagctgtc agctctagca aaag 24

<210> SEQ ID NO 390
<211> LENGTH: 19
<212> TYPE: DNA
<213> ORGANISM: Artificial Sequence
<220> FEATURE:
<223> OTHER INFORMATION: forward primer

<400> SEQUENCE: 390
gcccgaaacg ccgaatata 19

<210> SEQ ID NO 391
<211> LENGTH: 21
<212> TYPE: DNA
<213> ORGANISM: Artificial Sequence
<220> FEATURE:
<223> OTHER INFORMATION: probe

<400> SEQUENCE: 391
taccgcagca aaccgcttgg g 21

<210> SEQ ID NO 392
<211> LENGTH: 23
<212> TYPE: DNA
<213> ORGANISM: Artificial Sequence
<220> FEATURE:
<223> OTHER INFORMATION: reverse primer

<400> SEQUENCE: 392
cgtggctctc ttatcctcat gat 23

<210> SEQ ID NO 393
<211> LENGTH: 20
<212> TYPE: DNA
<213> ORGANISM: Artificial Sequence
<220> FEATURE:
<223> OTHER INFORMATION: forward primer

<400> SEQUENCE: 393
ggtgtgccac agaccttcct 20

<210> SEQ ID NO 394
<211> LENGTH: 24
<212> TYPE: DNA
<213> ORGANISM: Artificial Sequence
<220> FEATURE:
<223> OTHER INFORMATION: reverse primer

<400> SEQUENCE: 394
acggagttct tgacagagtt ttga 24

<210> SEQ ID NO 395
<211> LENGTH: 27
<212> TYPE: DNA
<213> ORGANISM: Artificial Sequence
<220> FEATURE:
<223> OTHER INFORMATION: probe

<400> SEQUENCE: 395
ttggcctgta atcacctgtg cagcctt 27

<210> SEQ ID NO 396
<211> LENGTH: 19
<212> TYPE: DNA
<213> ORGANISM: Artificial Sequence
<220> FEATURE:
<223> OTHER INFORMATION: forward primer

<400> SEQUENCE: 396
tccctgcggt cccagatag 19

<210> SEQ ID NO 397
<211> LENGTH: 20
<212> TYPE: DNA
<213> ORGANISM: Artificial Sequence
<220> FEATURE:
<223> OTHER INFORMATION: reverse primer

<400> SEQUENCE: 397
gtgggaacag ggtggacact 20

<210> SEQ ID NO 398
<211> LENGTH: 25
<212> TYPE: DNA
<213> ORGANISM: Artificial Sequence
<220> FEATURE:
<223> OTHER INFORMATION: probe

<400> SEQUENCE: 398
atcctgcccg gagtggaact gaagc 25

<210> SEQ ID NO 399
<211> LENGTH: 20
<212> TYPE: DNA

-continued

<213> ORGANISM: Artificial Sequence
<220> FEATURE:
<223> OTHER INFORMATION: forward primer

<400> SEQUENCE: 399
aatccaaggg ggagagtgat 20

<210> SEQ ID NO 400
<211> LENGTH: 26
<212> TYPE: DNA
<213> ORGANISM: Artificial Sequence
<220> FEATURE:
<223> OTHER INFORMATION: probe

<400> SEQUENCE: 400
catatggact ttgactcagc tgtggc 26

<210> SEQ ID NO 401
<211> LENGTH: 20
<212> TYPE: DNA
<213> ORGANISM: Artificial Sequence
<220> FEATURE:
<223> OTHER INFORMATION: reverse primer

<400> SEQUENCE: 401
gtacagattt tgcccgagga 20

<210> SEQ ID NO 402
<211> LENGTH: 21
<212> TYPE: DNA
<213> ORGANISM: Artificial Sequence
<220> FEATURE:
<223> OTHER INFORMATION: forward primer

<400> SEQUENCE: 402
tgtggacatc ttcccctcag a 21

<210> SEQ ID NO 403
<211> LENGTH: 24
<212> TYPE: DNA
<213> ORGANISM: Artificial Sequence
<220> FEATURE:
<223> OTHER INFORMATION: probe

<400> SEQUENCE: 403
ttccctactg agccaccttc tctg 24

<210> SEQ ID NO 404
<211> LENGTH: 18
<212> TYPE: DNA
<213> ORGANISM: Artificial Sequence
<220> FEATURE:
<223> OTHER INFORMATION: reverse primer

<400> SEQUENCE: 404
ctagcccgac cggttcgt 18

<210> SEQ ID NO 405
<211> LENGTH: 24
<212> TYPE: DNA
<213> ORGANISM: Artificial Sequence
<220> FEATURE:
<223> OTHER INFORMATION: forward primer

<400> SEQUENCE: 405
ctatatgcag ccagagatgt gaca 24

<210> SEQ ID NO 406
<211> LENGTH: 23
<212> TYPE: DNA
<213> ORGANISM: Artificial Sequence
<220> FEATURE:
<223> OTHER INFORMATION: probe

<400> SEQUENCE: 406
acagcctgcc actcatcaca gcc 23

<210> SEQ ID NO 407
<211> LENGTH: 24
<212> TYPE: DNA
<213> ORGANISM: Artificial Sequence
<220> FEATURE:
<223> OTHER INFORMATION: reverse primer

<400> SEQUENCE: 407
ccacgagttt cttactgaga atgg 24

<210> SEQ ID NO 408
<211> LENGTH: 19
<212> TYPE: DNA
<213> ORGANISM: Artificial Sequence
<220> FEATURE:
<223> OTHER INFORMATION: forward primer

<400> SEQUENCE: 408
gggccaaata ttcagaagc 19

<210> SEQ ID NO 409
<211> LENGTH: 20
<212> TYPE: DNA
<213> ORGANISM: Artificial Sequence
<220> FEATURE:
<223> OTHER INFORMATION: reverse primer

<400> SEQUENCE: 409
ggatgggtat gatgggacag 20

<210> SEQ ID NO 410
<211> LENGTH: 20
<212> TYPE: DNA
<213> ORGANISM: Artificial Sequence
<220> FEATURE:
<223> OTHER INFORMATION: probe

<400> SEQUENCE: 410
ccaccatagc ggccatggag 20

<210> SEQ ID NO 411
<211> LENGTH: 22
<212> TYPE: DNA
<213> ORGANISM: Artificial Sequence
<220> FEATURE:
<223> OTHER INFORMATION: forward primer

<400> SEQUENCE: 411
cttcacagtg ctcctgcagt ct 22

<210> SEQ ID NO 412
<211> LENGTH: 21
<212> TYPE: DNA
<213> ORGANISM: Artificial Sequence
<220> FEATURE:
<223> OTHER INFORMATION: reverse primer

<400> SEQUENCE: 412
catctgcttc agctcgttgg t 21

<210> SEQ ID NO 413
<211> LENGTH: 26
<212> TYPE: DNA
<213> ORGANISM: Artificial Sequence
<220> FEATURE:
<223> OTHER INFORMATION: probe

<400> SEQUENCE: 413
aagtacacgt aagttacagc cacaca 26

<210> SEQ ID NO 414
<211> LENGTH: 18
<212> TYPE: DNA
<213> ORGANISM: Artificial Sequence
<220> FEATURE:
<223> OTHER INFORMATION: forward primer

<400> SEQUENCE: 414
gcctcggtgt gcctttca 18

<210> SEQ ID NO 415
<211> LENGTH: 22
<212> TYPE: DNA
<213> ORGANISM: Artificial Sequence
<220> FEATURE:
<223> OTHER INFORMATION: probe

<400> SEQUENCE: 415
catcgccagc tacgccctgc tc 22

<210> SEQ ID NO 416
<211> LENGTH: 19
<212> TYPE: DNA
<213> ORGANISM: Artificial Sequence
<220> FEATURE:
<223> OTHER INFORMATION: reverse primer

<400> SEQUENCE: 416
cgtgatgtgc gcaatcatg 19

<210> SEQ ID NO 417
<211> LENGTH: 19
<212> TYPE: DNA
<213> ORGANISM: Artificial Sequence
<220> FEATURE:
<223> OTHER INFORMATION: forward primer

<400> SEQUENCE: 417
gtggatgtgc cctgaagga 19

<210> SEQ ID NO 418
<211> LENGTH: 20
<212> TYPE: DNA
<213> ORGANISM: Artificial Sequence
<220> FEATURE:
<223> OTHER INFORMATION: reverse primer

<400> SEQUENCE: 418
ctgcggatcc agggtaagaa 20

<210> SEQ ID NO 419
<211> LENGTH: 28
<212> TYPE: DNA

<213> ORGANISM: Artificial Sequence
<220> FEATURE:
<223> OTHER INFORMATION: probe

<400> SEQUENCE: 419
aagccaggcg tctacacgag agtctcac 28

<210> SEQ ID NO 420
<211> LENGTH: 20
<212> TYPE: DNA
<213> ORGANISM: Artificial Sequence
<220> FEATURE:
<223> OTHER INFORMATION: forward primer

<400> SEQUENCE: 420
gccctggatt tcagaaagag 20

<210> SEQ ID NO 421
<211> LENGTH: 20
<212> TYPE: DNA
<213> ORGANISM: Artificial Sequence
<220> FEATURE:
<223> OTHER INFORMATION: reverse primer

<400> SEQUENCE: 421
agttacaagc cagggaagga 20

<210> SEQ ID NO 422
<211> LENGTH: 25
<212> TYPE: DNA
<213> ORGANISM: Artificial Sequence
<220> FEATURE:
<223> OTHER INFORMATION: probe

<400> SEQUENCE: 422
caagtctgga tctgggaccc tttcc 25

<210> SEQ ID NO 423
<211> LENGTH: 20
<212> TYPE: DNA
<213> ORGANISM: Artificial Sequence
<220> FEATURE:
<223> OTHER INFORMATION: forward primer

<400> SEQUENCE: 423
ctgctgtctt gggtgcattg 20

<210> SEQ ID NO 424
<211> LENGTH: 18
<212> TYPE: DNA
<213> ORGANISM: Artificial Sequence
<220> FEATURE:
<223> OTHER INFORMATION: reverse primer

<400> SEQUENCE: 424
gcagcctggg accacttg 18

<210> SEQ ID NO 425
<211> LENGTH: 25
<212> TYPE: DNA
<213> ORGANISM: Artificial Sequence
<220> FEATURE:
<223> OTHER INFORMATION: probe

<400> SEQUENCE: 425
ttgccttgct gctctacctc cacca 25

-continued

<210> SEQ ID NO 426
<211> LENGTH: 19
<212> TYPE: DNA
<213> ORGANISM: Artificial Sequence
<220> FEATURE:
<223> OTHER INFORMATION: forward primer

<400> SEQUENCE: 426
tgacgatggc ctggagtgt 19

<210> SEQ ID NO 427
<211> LENGTH: 22
<212> TYPE: DNA
<213> ORGANISM: Artificial Sequence
<220> FEATURE:
<223> OTHER INFORMATION: reverse primer

<400> SEQUENCE: 427
ggtaccggat catgaggatc tg 22

<210> SEQ ID NO 428
<211> LENGTH: 21
<212> TYPE: DNA
<213> ORGANISM: Artificial Sequence
<220> FEATURE:
<223> OTHER INFORMATION: probe

<400> SEQUENCE: 428
ctgggcagca ccaagtccgg a 21

<210> SEQ ID NO 429
<211> LENGTH: 22
<212> TYPE: DNA
<213> ORGANISM: Artificial Sequence
<220> FEATURE:
<223> OTHER INFORMATION: forward primer

<400> SEQUENCE: 429
agaggcatcc atgaacttca ca 22

<210> SEQ ID NO 430
<211> LENGTH: 24
<212> TYPE: DNA
<213> ORGANISM: Artificial Sequence
<220> FEATURE:
<223> OTHER INFORMATION: reverse primer

<400> SEQUENCE: 430
caaactccac agtacttggg ttga 24

<210> SEQ ID NO 431
<211> LENGTH: 20
<212> TYPE: DNA
<213> ORGANISM: Artificial Sequence
<220> FEATURE:
<223> OTHER INFORMATION: probe

<400> SEQUENCE: 431
cgggctgcat cagcacacgc 20

<210> SEQ ID NO 432
<211> LENGTH: 23
<212> TYPE: DNA
<213> ORGANISM: Artificial Sequence
<220> FEATURE:
<223> OTHER INFORMATION: forward primer

<400> SEQUENCE: 432
gcagttggaa gacacaggaa agt 23

<210> SEQ ID NO 433
<211> LENGTH: 27
<212> TYPE: DNA
<213> ORGANISM: Artificial Sequence
<220> FEATURE:
<223> OTHER INFORMATION: probe

<400> SEQUENCE: 433
tccccaaatt gcagatttat caacggc 27

<210> SEQ ID NO 434
<211> LENGTH: 21
<212> TYPE: DNA
<213> ORGANISM: Artificial Sequence
<220> FEATURE:
<223> OTHER INFORMATION: reverse primer

<400> SEQUENCE: 434
tgcgtggcac tattttcaag a 21

<210> SEQ ID NO 435
<211> LENGTH: 25
<212> TYPE: DNA
<213> ORGANISM: Artificial Sequence
<220> FEATURE:
<223> OTHER INFORMATION: forward primer

<400> SEQUENCE: 435
agactgtgga gtttgatgtt gttga 25

<210> SEQ ID NO 436
<211> LENGTH: 22
<212> TYPE: DNA
<213> ORGANISM: Artificial Sequence
<220> FEATURE:
<223> OTHER INFORMATION: reverse primer

<400> SEQUENCE: 436
ggaacaccac caggacctgt aa 22

<210> SEQ ID NO 437
<211> LENGTH: 23
<212> TYPE: DNA
<213> ORGANISM: Artificial Sequence
<220> FEATURE:
<223> OTHER INFORMATION: probe

<400> SEQUENCE: 437
ttgctgcctc cgcacccttt tct 23

<210> SEQ ID NO 438
<211> LENGTH: 20
<212> TYPE: DNA
<213> ORGANISM: Artificial Sequence
<220> FEATURE:
<223> OTHER INFORMATION: forward primer

<400> SEQUENCE: 438
acccagtagc aaggagaagc 20

<210> SEQ ID NO 439
<211> LENGTH: 20
<212> TYPE: DNA

-continued

```
<213> ORGANISM: Artificial Sequence
<220> FEATURE:
<223> OTHER INFORMATION: reverse primer

<400> SEQUENCE: 439

cagctggtgg taggttctga                                                   20


<210> SEQ ID NO 440
<211> LENGTH: 21
<212> TYPE: DNA
<213> ORGANISM: Artificial Sequence
<220> FEATURE:
<223> OTHER INFORMATION: probe

<400> SEQUENCE: 440

cactcactgc tccgagtgcg g                                                 21
```

GENE EXPRESSION MARKERS FOR BREAST CANCER PROGNOSIS

This application is a divisional application of U.S. application Ser. No. 13/221,549, filed Aug. 30, 2011, now U.S. Pat. No. 8,206,919, which is a divisional application of U.S. application Ser. No. 12/478,632, filed on Jun. 4, 2009, now U.S. Pat. No. 8,034,565, which is a continuation application of U.S. application Ser. No. 10/758,307, filed on Jan. 14, 2004, now U.S. Pat. No. 7,569,345, which claims priority under 35 U.S.C. §119(e) to U.S. provisional application No. 60/440,861, filed on Jan. 15, 2003, the entire disclosures of which are hereby expressly incorporated by reference.

BACKGROUND OF THE INVENTION

This application contains a Sequence Listing submitted in ASCII text file titled "GHDX008DIV2SEQLISTING.TXT," created May 16, 2012, comprising 82KB, which is hereby expressly incorporated by reference.

1. Field of the Invention

The present invention provides genes and gene sets the expression of which is important in the diagnosis and/or prognosis of breast cancer.

2. Description of the Related Art

Oncologists have a number of treatment options available to them, including different combinations of chemotherapeutic drugs that are characterized as "standard of care," and a number of drugs that do not carry a label claim for particular cancer, but for which there is evidence of efficacy in that cancer. Best likelihood of good treatment outcome requires that patients be assigned to optimal available cancer treatment, and that this assignment be made as quickly as possible following diagnosis.

Currently, diagnostic tests used in clinical practice are single analyte, and therefore do not capture the potential value of knowing relationships between dozens of different markers. Moreover, diagnostic tests are frequently not quantitative, relying on immunohistochemistry. This method often yields different results in different laboratories, in part because the reagents are not standardized, and in part because the interpretations are subjective and cannot be easily quantified. RNA-based tests have not often been used because of the problem of RNA degradation over time and the fact that it is difficult to obtain fresh tissue samples from patients for analysis. Fixed paraffin-embedded tissue is more readily available and methods have been established to detect RNA in fixed tissue. However, these methods typically do not allow for the study of large numbers of genes (DNA or RNA) from small amounts of material. Thus, traditionally fixed tissue has been rarely used other than for immunohistochemistry detection of proteins.

Recently, several groups have published studies concerning the classification of various cancer types by microarray gene expression analysis (see, e.g. Golub et al., *Science* 286:531-537 (1999); Bhattacharjae et al., *Proc. Natl. Acad. Sci. USA* 98:13790-13795 (2001); Chen-Hsiang et al., *Bioinformatics* 17 (Suppl. 1):S316-S322 (2001); Ramaswamy et al., *Proc. Natl. Acad. Sci. USA* 98:15149-15154 (2001)). Certain classifications of human breast cancers based on gene expression patterns have also been reported (Martin et al., *Cancer Res.* 60:2232-2238 (2000); West et al., *Proc. Natl. Acad. Sci. USA* 98:11462-11467 (2001); Sorlie et al., *Proc. Natl. Acad. Sci. USA* 98:10869-10874 (2001); Yan et al., *Cancer Res.* 61:8375-8380 (2001)). However, these studies mostly focus on improving and refining the already established classification of various types of cancer, including breast cancer, and generally do not provide new insights into the relationships of the differentially expressed genes, and do not link the findings to treatment strategies in order to improve the clinical outcome of cancer therapy.

Although modern molecular biology and biochemistry have revealed hundreds of genes whose activities influence the behavior of tumor cells, state of their differentiation, and their sensitivity or resistance to certain therapeutic drugs, with a few exceptions, the status of these genes has not been exploited for the purpose of routinely making clinical decisions about drug treatments. One notable exception is the use of estrogen receptor (ER) protein expression in breast carcinomas to select patients to treatment with anti-estrogen drugs, such as tamoxifen. Another exceptional example is the use of ErbB2 (Her2) protein expression in breast carcinomas to select patients with the Her2 antagonist drug Herceptin® (Genentech, Inc., South San Francisco, Calif.).

Despite recent advances, the challenge of cancer treatment remains to target specific treatment regimens to pathogenically distinct tumor types, and ultimately personalize tumor treatment in order to maximize outcome. Hence, a need exists for tests that simultaneously provide predictive information about patient responses to the variety of treatment options. This is particularly true for breast cancer, the biology of which is poorly understood. It is clear that the classification of breast cancer into a few subgroups, such as $ErbB2^+$ subgroup, and subgroups characterized by low to absent gene expression of the estrogen receptor (ER) and a few additional transcriptional factors (Perou et al., *Nature* 406:747-752 (2000)) does not reflect the cellular and molecular heterogeneity of breast cancer, and does not allow the design of treatment strategies maximizing patient response.

SUMMARY OF THE INVENTION

The present invention provides a set of genes, the expression of which has prognostic value, specifically with respect to disease-free survival.

The present invention accommodates the use of archived paraffin-embedded biopsy material for assay of all markers in the set, and therefore is compatible with the most widely available type of biopsy material. It is also compatible with several different methods of tumor tissue harvest, for example, via core biopsy or fine needle aspiration. Further, for each member of the gene set, the invention specifies oligonucleotide sequences that can be used in the test.

In one aspect, the invention concerns a method of predicting the likelihood of long-term survival of a breast cancer patient without the recurrence of breast cancer, comprising determining the expression level of one or more prognostic RNA transcripts or their expression products in a breast cancer tissue sample obtained from the patient, normalized against the expression level of all RNA transcripts or their products in the breast cancer tissue sample, or of a reference set of RNA transcripts or their expression products, wherein the prognostic RNA transcript is the transcript of one or more genes selected from the group consisting of: TP53BP2, GRB7, PR, CD68, Bc12, KRT14, IRS1, CTSL, EstR1, Chk1, IGFBP2, BAG1, CEGP1, STK15, GSTM1, FHIT, RIZ1, AIB1, SURV, BBC3, IGF1R, p27, GATA3, ZNF217, EGFR, CD9, MYBL2, HIF1α, pS2, ErbB3, TOP2B, MDM2, RAD51C, KRT19, TS, Her2, KLK10, β-Catenin, γ-Catenin, MCM2, PI3KC2A, IGF1, TBP, CCNB1, FBXO5, and DR5, wherein expression of one or more of GRB7, CD68, CTSL, Chk1, CCNB1, MCM2, FBXO5, Her2, STK15, SURV, EGFR, MYBL2, HIF1α, and TS indicates a decreased likelihood of long-term survival without breast cancer recurrence, and the expression of one or more of TP53BP2, PR, Bc12, KRT14, EstR1, IGFBP2, BAG1, CEGP1, KLK10, β-Catenin, γ-Catenin, DR5, PI3KCA2, RAD51C, GSTM1, FHIT, RIZ1, BBC3, TBP, p27, IRS1, IGF1R, GATA3, ZNF217, CD9, pS2, ErbB3, TOP2B, MDM2, IGF1, and KRT19 indicates an increased likelihood of long-term survival without breast cancer recurrence.

In a particular embodiment, the expression levels of at least two, or at least 5, or at least 10, or at least 15 of the prognostic RNA transcripts or their expression products are determined. In another embodiment, the method comprises the determination of the expression levels of all prognostic RNA transcripts or their expression products.

In another particular embodiment, the breast cancer is invasive breast carcinoma.

In a further embodiment, RNA is isolated from a fixed, wax-embedded breast cancer tissue specimen of the patient. Isolation may be performed by any technique known in the art, for example from core biopsy tissue or fine needle aspirate cells.

In another aspect, the invention concerns an array comprising polynucleotides hybridizing to two or more of the following genes: α-Catenin, AIB1, AKT1, AKT2, β-actin, BAG1, BBC3, Bc12, CCNB1, CCND1, CD68, CD9, CDH1, CEGP1, Chk1, CIAP1, cMet.2, Contig 27882, CTSL, DR5, EGFR, EIF4E, EPHX1, ErbB3, EstR1, FBXO5, FHIT1 FRP1, GAPDH, GATA3, G-Catenin, GRB7, GRO1, GSTM1, GUS, HER2, HIF1A, HNF3A, IGF1R, IGFBP2, KLK10, KRT14, KRT17, KRT18, KRT19, KRT5, Maspin, MCM2, MCM3, MDM2, MMP9, MTA1, MYBL2, P14ARF, p27, P53, PI3KC2A, PR, PRAME, pS2, RAD51C, 3RB1, RIZ1, STK15, STMY3, SURV, TGFA, TOP2B, TP53BP2, TRAIL, TS, upa, VDR, VEGF, and ZNF217.

In particular embodiments, the array comprises polynucleotides hybridizing to at least 3, or at least 5, or at least 10, or at least 15, or at least 20, or all of the genes listed above.

In another specific embodiment, the array comprises polynucleotides hybridizing to the following genes: TP53BP2, GRB7, PR, CD68, Bc12, KRT14, IRS1, CTSL, EstR1, Chk1, IGFBP2, BAG1, CEGP1, STK15, GSTM1, FHIT, RIZ1, AIB1, SURV, BBC3, IGF1R, p27, GATA3, ZNF217, EGFR, CD9, MYBL2, HIF1α, pS2, RIZ1, ErbB3, TOP2B, MDM2, RAD51C, KRT19, TS, Her2, KLK10, β-Catenin, γ-Catenin, MCM2, PI3KC2A, IGF1, TBP, CCNB1, FBXO5 and DR5.

The polynucleotides can be cDNAs, or oligonucleotides, and the solid surface on which they are displayed may, for example, be glass.

In another aspect, the invention concerns a method of predicting the likelihood of long-term survival of a patient diagnosed with invasive breast cancer, without the recurrence of breast cancer, comprising the steps of:

(1) determining the expression levels of the RNA transcripts or the expression products of genes or a gene set selected from the group consisting of (a) TP53BP2, Bc12, BAD, EPHX1, PDGFRβ3, DIABLO, XIAP, YB1, CA9, and KRT8;

(b) GRB7, CD68, TOP2A, Bc12, DIABLO, CD3, 1D1, PPM1D, MCM6, and WISP1;

(c) PR, TP53BP2, PRAME, DIABLO, CTSL, IGFBP2, TIMP1, CA9, MMP9, and COX2;

(d) CD68, GRB7, TOP2A, Bc12, DIABLO, CD3, TD1, PPM1D, MCM6, and WISP1;

(e) Bc12, TP53BP2, BAD, EPHX1, PDGFRβ, DIABLO, XIAP, YB1, CA9, and KRT8;

(f) KRT14, KRT5, PRAME, TP53BP2, GUS1, AIB1, MCM3, CCNE1, MCM6, and ID1;

(g) PRAME, TP53BP2, EstR1, DIABLO, CTSL, PPM1D, GRB7, DAPK1, BBC3, and VEGFB;

(h) CTSL2, GRB7, TOP2A, CCNB1, Bc12, DIABLO, PRAME, EMS1, CA9, and EpCAM;

(i) EstR1, TP53BP2, PRAME, DIABLO, CTSL, PPM1D, GRB7, DAPK1, BBC3, and VEGFB;

(k) Chk1, PRAME, TP53BP2, GRB7, CA9, CTSL, CCNB1, TOP2A, tumor size, and IGFBP2;

(l) IGFBP2, GRB7, PRAME, DIABLO, CTSL, β-Catenin, PPM1D, Chk1, WISP1, and LOT1;

(m) HER2, TP53BP2, Bc12, DIABLO, TIMP1, EPHX1, TOP2A, TRAIL, CA9, and AREG;

(n) BAG1, TP53BP2, PRAME, IL6, CCNB1, PAI1, AREG, tumor size, CA9, and Ki67;

(o) CEGP1, TP53BP2, PRAME, DIABLO, Bc12, COX2, CCNE1, STK15, and AKT2, and FGF18;

(p) STK15, TP53BP2, PRAME, IL6, CCNE1, AKT2, DIABLO, cMet, CCNE2, and COX2;

(q) KLK10, EstR1, TP53BP2, PRAME, DIABLO, CTSL, PPM1D, GRB7, DAPK1, and BBC3;

(r) AIB1, TP53BP2, Bc12, DIABLO, TIMP1, CD3, p53, CA9, GRB7, and EPHX1

(s) BBC3, GRB7, CD68, PRAME, TOP2A, CCNB1, EPHX1, CTSL GSTM1, and APC;

(t) CD9, GRB7, CD68, TOP2A, Bc12, CCNB1, CD3, DIABLO, ID1, and PPM1D;

(w) EGFR, KRT14, GRB7, TOP2A, CCNB1, CTSL, Bc12, TP, KLK10, and CA9;

(x) HIF1α, PR, DIABLO, PRAME, Chk1, AKT2, GRB7, CCNE1, TOP2A, and CCNB1;

(y) MDM2, TP53BP2, DIABLO, Bc12, AIB1, TIMP1, CD3, p53, CA9, and HER2;

(z) MYBL2, TP53BP2, PRAME, IL6, Bc12, DIABLO, CCNE1, EPHX1, TIMP1, and CA9;

(aa) p2'7, TP53BP2, PRAME, DIABLO, Bc12, COX2, CCNE1, STK15, AKT2, and 1D1

(ab) RAD51, GRB7, CD68, TOP2A, CIAP2, CCNB1, BAG1, IL6, FGFR1, and TP53BP2;

(ac) SURV, GRB7, TOP2A, PRAME, CTSL, GSTM1, CCNB1, VDR, CA9; and CCNE2;

(ad) TOP2B, TP53BP2, DIABLO, Bc12, TIMP1, AIB1, CA9, p53, KRT8, and BAD;

(ae) ZNF217, GRB7, TP53BP2, PRAME, DIABLO, Bc12, COX2, CCNE1, APC4, and β-Catenin, in a breast cancer tissue sample obtained from the patient, normalized against the expression levels of all RNA transcripts or their expression products in said breast cancer tissue sample, or of a reference set of RNA transcripts or their products;

(2) subjecting the data obtained in step (1) to statistical analysis; and (3) determining whether the likelihood of said long-term survival has increased or decreased.

In a further aspect, the invention concerns a method of predicting the likelihood of long-term survival of a patient diagnosed with estrogen receptor (ER)-positive invasive breast cancer, without the recurrence of breast cancer, comprising the steps of:

(1) determining the expression levels of the RNA transcripts or the expression products of genes of a gene set selected from the group consisting of CD68; CTSL; FBXO5; SURV; CCNB1; MCM2; Chk1; MYBL2; HIF1A; cMET; EGFR; TS; STK15, IGFR1; BCl2; HNF3A; TP53BP2; GATA3; BBC3; RAD51C; BAG1; IGFBP2; PR; CD9; RB1; EPHX1; CEGP1; TRAIL; DR5; p2'7; p53; MTA; RIZ1;

ErbB3; TOP2B; EIF4E, wherein expression of the following genes in ER-positive cancer is indicative of a reduced likelihood of survival without cancer recurrence following surgery: CD68; CTSL; FBXO5; SURV; CCNB1; MCM2; Chk1; MYBL2; HIF1A; cMET; EGFR; TS; STK15, and wherein expression of the following genes is indicative of a better prognosis for survival without cancer recurrence following surgery: IGFR1; BCl2; HNF3A; TP53BP2; GATA3; BBC3; RAD51C; BAG1; IGFBP2; PR; CD9; RB1; EPHX1; CEGP1; TRAIL; DR5; p27; p53; MTA; RIZ1; ErbB3; TOP2B; EIF4E.

(2) subjecting the data obtained in step (1) to statistical analysis; and (3) determining whether the likelihood of said long-term survival has increased or decreased.

In yet another aspect, the invention concerns a method of predicting the likelihood of long-term survival of a patient diagnosed with estrogen receptor (ER)-negative invasive breast cancer, without the recurrence of breast cancer, comprising determining the expression levels of the RNA transcripts or the expression products of genes of the gene set CCND1; UPA; HNF3A; CDH1; Her2; GRB7; AKT1; STMY3; α-Catenin; VDR; GRO1; KT14; KLK10; Maspin, TGFα, and FRP1, wherein expression of the following genes is indicative of a reduced likelihood of survival without cancer recurrence: CCND1; UPA; HNF3A; CDH1; Her2; GRB7; AKT1; STMY3; α-Catenin; VDR; GRO1, and wherein expression of the following genes is indicative of a better prognosis for survival without cancer recurrence: KT14; KLK10; Maspin, TGFα, and FRP1.

In a different aspect, the invention concerns a method of preparing a personalized genomics profile for a patient, comprising the steps of:

(a) subjecting RNA extracted from a breast tissue obtained from the patient to gene expression analysis;

(b) determining the expression level of one or more genes selected from the breast cancer gene set listed in any one of Tables 1-5, wherein the expression level is normalized against a control gene or genes and optionally is compared to the amount found in a breast cancer reference tissue set; and (c) creating a report summarizing the data obtained by the gene expression analysis.

The report may, for example, include prediction of the likelihood of long term survival of the patient and/or recommendation for a treatment modality of said patient.

In a further aspect, the invention concerns a method for amplification of a gene listed in Tables 5A and B by polymerase chain reaction (PCR), comprising performing said PCR by using an amplicon listed in Tables 5A and B and a primer-probe set listed in Tables 6A-F.

In a still further aspect, the invention concerns a PCR amplicon listed in Tables 5A and B.

In yet another aspect, the invention concerns a PCR primer-probe set listed in Tables 6A-F.

The invention further concerns a prognostic method comprising:

(a) subjecting a sample comprising breast cancer cells obtained from a patient to quantitative analysis of the expression level of the RNA transcript of at least one gene selected from the group consisting of GRB7, CD68, CTSL, Chk1, AIB1, CCNB1, MCM2, FBXO5, Her2, STK15, SURV, EGFR, MYBL2, HIF1α, and TS, or their product, and (b) identifying the patient as likely to have a decreased likelihood of long-term survival without breast cancer recurrence if the normalized expression levels of the gene or genes, or their products, are elevated above a defined expression threshold.

In a different aspect, the invention concerns a prognostic method comprising:

(a) subjecting a sample comprising breast cancer cells obtained from a patient to quantitative analysis of the expression level of the RNA transcript of at least one gene selected from the group consisting of TP53BP2, PR, Bc12, KRT14, EstR1, IGFBP2, BAG1, CEGP1, KLK10, β-Catenin, γ-Catenin, DR5, PI3KCA2, RAD51C, GSTM1, FHIT, RIZ1, BBC3, TBP, p27, IRS1, IGF1R, GATA3, ZNF217, CD9, pS2, ErbB3, TOP2B, MDM2, IGF1, and KRT19, and (b) identifying the patient as likely to have an increased likelihood of long-term survival without breast cancer recurrence if the normalized expression levels of the gene or genes, or their products, are elevated above a defined expression threshold.

The invention further concerns a kit comprising one or more of (1) extraction buffer/reagents and protocol; (2) reverse transcription buffer/reagents and protocol; and (3) qPCR buffer/reagents and protocol suitable for performing any of the foregoing methods.

Table 1 is a list of genes, expression of which correlate with breast cancer survival. Results from a retrospective clinical trial. Binary statistical analysis.

Table 2 is a list of genes, expression of which correlates with breast cancer survival in estrogen receptor (ER) positive patients. Results from a retrospective clinical trial. Binary statistical analysis.

Table 3 is a list of genes, expression of which correlates with breast cancer survival in estrogen receptor (ER) negative patients. Results from a retrospective clinical trial. Binary statistical analysis.

Table 4 is a list of genes, expression of which correlates with breast cancer survival. Results from a retrospective clinical trial. Cox proportional hazards statistical analysis.

Tables 5A and B show a list of genes, expression of which correlate with breast cancer survival. Results from a retrospective clinical trial. The table includes accession numbers for the genes, and amplicon sequences used for PCR amplification.

Tables 6A-6F The table includes sequences for the forward and reverse primers (designated by "f" and "r", respectively) and probes (designated by "p") used for PCR amplification of the amplicons listed in Tables 5A-B.

DETAILED DESCRIPTION OF THE PREFERRED EMBODIMENT

A. Definitions

Unless defined otherwise, technical and scientific terms used herein have the same meaning as commonly understood by one of ordinary skill in the art to which this invention belongs. Singleton et al., Dictionary of Microbiology and Molecular Biology 2nd ed., J. Wiley & Sons (New York, N.Y. 1994), and March, Advanced Organic Chemistry Reactions, Mechanisms and Structure 4th ed., John Wiley & Sons (New York, N.Y. 1992), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

The term "microarray" refers to an ordered arrangement of hybridizable array elements, preferably polynucleotide probes, on a substrate.

The term "polynucleotide," when used in singular or plural, generally refers to any polyribonucleotide or polydeoxribonucleotide, which may be unmodified RNA or DNA or modified RNA or DNA. Thus, for instance, polynucleotides as defined herein include, without limitation, single- and double-stranded DNA, DNA including single- and double-stranded regions, single- and double-stranded RNA, and RNA including single- and double-stranded regions, hybrid molecules comprising DNA and RNA that may be single-stranded or, more typically, double-stranded or include single- and double-stranded regions. In addition, the term "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. The term "polynucleotide" specifically includes cDNAs. The term includes DNAs (including cDNAs) and RNAs that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritiated bases, are included within the term "polynucleotides" as defined herein. In general, the term "polynucleotide" embraces all chemically, enzymatically and/or metabolically modified forms of unmodified polynucleotides, as well as the chemical forms of DNA and RNA characteristic of viruses and cells, including simple and complex cells.

The term "oligonucleotide" refers to a relatively short polynucleotide, including, without limitation, single-stranded deoxyribonucleotides, single- or double-stranded ribonucleotides, RNA:DNA hybrids and double-stranded DNAs. Oligonucleotides, such as single-stranded DNA probe oligonucleotides, are often synthesized by chemical methods, for example using automated oligonucleotide synthesizers that are commercially available. However, oligonucleotides can be made by a variety of other methods, including in vitro recombinant DNA-mediated techniques and by expression of DNAs in cells and organisms.

The terms "differentially expressed gene," "differential gene expression" and their synonyms, which are used interchangeably, refer to a gene whose expression is activated to a higher or lower level in a subject suffering from a disease, specifically cancer, such as breast cancer, relative to its expression in a normal or control subject. The terms also include genes whose expression is activated to a higher or lower level at different stages of the same disease. It is also understood that a differentially expressed gene may be either activated or inhibited at the nucleic acid level or protein level, or may be subject to alternative splicing to result in a different polypeptide product. Such differences may be evidenced by a change in mRNA levels, surface expression, secretion or other partitioning of a polypeptide, for example. Differential gene expression may include a comparison of expression between two or more genes or their gene products, or a comparison of the ratios of the expression between two or more genes or their gene products, or even a comparison of two differently processed products of the same gene, which differ between normal subjects and subjects suffering from a disease, specifically cancer, or between various stages of the same disease. Differential expression includes both quantitative, as well as qualitative, differences in the temporal or cellular expression pattern in a gene or its expression products among, for example, normal and diseased cells, or among cells which have undergone different disease events or disease stages. For the purpose of this invention, "differential gene expression" is considered to be present when there is at least an about two-fold, preferably at least about four-fold, more preferably at least about six-fold, most preferably at least about ten-fold difference between the expression of a given gene in normal and diseased subjects, or in various stages of disease development in a diseased subject.

The phrase "gene amplification" refers to a process by which multiple copies of a gene or gene fragment are formed in a particular cell or cell line. The duplicated region (a stretch of amplified DNA) is often referred to as "amplicon." Usually, the amount of the messenger RNA (mRNA) produced, i.e., the level of gene expression, also increases in the proportion of the number of copies made of the particular gene expressed.

The term "diagnosis" is used herein to refer to the identification of a molecular or pathological state, disease or condition, such as the identification of a molecular subtype of head and neck cancer, colon cancer, or other type of cancer.

The term "prognosis" is used herein to refer to the prediction of the likelihood of cancer-attributable death or progression, including recurrence, metastatic spread, and drug resistance, of a neoplastic disease, such as breast cancer.

The term "prediction" is used herein to refer to the likelihood that a patient will respond either favorably or unfavorably to a drug or set of drugs, and also the extent of those responses, or that a patient will survive, following surgical removal or the primary tumor and/or chemotherapy for a certain period of time without cancer recurrence. The predictive methods of the present invention can be used clinically to make treatment decisions by choosing the most appropriate treatment modalities for any particular patient. The predictive methods of the present invention are valuable tools in predicting if a patient is likely to respond favorably to a treatment regimen, such as surgical intervention, chemotherapy with a given drug or drug combination, and/or radiation therapy, or whether long-term survival of the patient, following surgery and/or termination of chemotherapy or other treatment modalities is likely.

The term "long-term" survival is used herein to refer to survival for at least 3 years, more preferably for at least 8 years, most preferably for at least 10 years following surgery or other treatment.

The term "tumor," as used herein, refers to all neoplastic cell growth and proliferation, whether malignant or benign, and all pre-cancerous and cancerous cells and tissues.

The terms "cancer" and "cancerous" refer to or describe the physiological condition in mammals that is typically characterized by unregulated cell growth. Examples of cancer include but are not limited to, breast cancer, colon cancer, lung cancer, prostate cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, and brain cancer.

The "pathology" of cancer includes all phenomena that compromise the well-being of the patient. This includes, without limitation, abnormal or uncontrollable cell growth, metastasis, interference with the normal functioning of neighboring cells, release of cytokines or other secretory products at abnormal levels, suppression or aggravation of inflammatory or immunological response, neoplasia, premalignancy, malignancy, invasion of surrounding or distant tissues or organs, such as lymph nodes, etc.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., *Current Protocols in Molecular Biology*, Wiley Interscience Publishers, (1995).

"Stringent conditions" or "high stringency conditions", as defined herein, typically: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" may be identified as described by Sambrook et al., *Molecular Cloning: A Laboratory Manual*, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

In the context of the present invention, reference to "at least one," "at least two," "at least five," etc. of the genes listed in any particular gene set means any one or any and all combinations of the genes listed.

The terms "expression threshold," and "defined expression threshold" are used interchangeably and refer to the level of a gene or gene product in question above which the gene or gene product serves as a predictive marker for patient survival without cancer recurrence. The threshold is defined experimentally from clinical studies such as those described in the Example below. The expression threshold can be selected either for maximum sensitivity, or for maximum selectivity, or for minimum error. The determination of the expression threshold for any situation is well within the knowledge of those skilled in the art.

B. Detailed Description

The practice of the present invention will employ, unless otherwise indicated, conventional techniques of molecular biology (including recombinant techniques), microbiology, cell biology, and biochemistry, which are within the skill of the art. Such techniques are explained fully in the literature, such as, "Molecular Cloning: A Laboratory Manual", $2^{nd}$ edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology", $4^{th}$ edition (D. M. Weir & C. C. Blackwell, eds., Blackwell Science Inc., 1987); "Gene Transfer Vectors for Mammalian Cells" (J. M. Miller & M. P. Calos, eds., 1987); "Current Protocols in Molecular Biology" (F. M. Ausubel et al., eds., 1987); and "PCR: The Polymerase Chain Reaction", (Mullis et al., eds., 1994).

1. Gene Expression Profiling

In general, methods of gene expression profiling can be divided into two large groups: methods based on hybridization analysis of polynucleotides, and methods based on sequencing of polynucleotides. The most commonly used methods known in the art for the quantification of mRNA expression in a sample include northern blotting and in situ hybridization (Parker & Barnes, *Methods in Molecular Biology* 106:247-283 (1999)); RNAse protection assays (Hod, *Biotechniques* 13:852-854 (1992)); and reverse transcription polymerase chain reaction (RT-PCR) (Weis et al., *Trends in Genetics* 8:263-264 (1992)). Alternatively, antibodies may be employed that can recognize specific duplexes, including DNA duplexes, RNA duplexes, and DNA-RNA hybrid duplexes or DNA-protein duplexes. Representative methods for sequencing-based gene expression analysis include Serial Analysis of Gene Expression (SAGE), and gene expression analysis by massively parallel signature sequencing (MPSS).

2. Reverse Transcriptase PCR (RT-PCR)

Of the techniques listed above, the most sensitive and most flexible quantitative method is RT-PCR, which can be used to compare mRNA levels in different sample populations, in normal and tumor tissues, with or without drug treatment, to characterize patterns of gene expression, to discriminate between closely related mRNAs, and to analyze RNA structure.

The first step is the isolation of mRNA from a target sample. The starting material is typically total RNA isolated from human tumors or tumor cell lines, and corresponding normal tissues or cell lines, respectively. Thus RNA can be isolated from a variety of primary tumors, including breast, lung, colon, prostate, brain, liver, kidney, pancreas, spleen, thymus, testis, ovary, uterus, etc., tumor, or tumor cell lines, with pooled DNA from healthy donors. If the source of mRNA is a primary tumor, mRNA can be extracted, for example, from frozen or archived paraffin-embedded and fixed (e.g. formalin-fixed) tissue samples.

General methods for mRNA extraction are well known in the art and are disclosed in standard textbooks of molecular biology, including Ausubel et al., *Current Protocols of Molecular Biology*, John Wiley and Sons (1997). Methods for RNA extraction from paraffin embedded tissues are disclosed, for example, in Rupp and Locker, *Lab Invest.* 56:A67 (1987), and De Andres et al., *BioTechniques* 18:42044 (1995). In particular, RNA isolation can be performed using purification kit, buffer set and protease from commercial manufacturers, such as Qiagen, according to the manufacturer's instructions. For example, total RNA from cells in culture can be isolated using Qiagen RNeasy mini-columns. Other commercially available RNA isolation kits include Master- Pure™ Complete DNA and RNA Purification Kit (EPICENTRE®, Madison, Wis.), and Paraffin Block RNA Isolation Kit (Ambion, Inc.). Total RNA from tissue samples can be isolated using RNA Stat-60 (Tel-Test). RNA prepared from tumor can be isolated, for example, by cesium chloride density gradient centrifugation.

As RNA cannot serve as a template for PCR, the first step in gene expression profiling by RT-PCR is the reverse transcription of the RNA template into cDNA, followed by its exponential amplification in a PCR reaction. The two most commonly used reverse transcriptases are avilo myeloblastosis virus reverse transcriptase (AMV-RT) and Moloney murine leukemia virus reverse transcriptase (MMLV-RT). The reverse transcription step is typically primed using specific primers, random hexamers, or oligo-dT primers, depending on the circumstances and the goal of expression profiling. For example, extracted RNA can be reverse-transcribed using a GeneAmp RNA PCR kit (Perkin Elmer, Calif., USA), following the manufacturer's instructions. The derived cDNA can then be used as a template in the subsequent PCR reaction.

Although the PCR step can use a variety of thermostable DNA-dependent DNA polymerases, it typically employs the Taq DNA polymerase, which has a 5'-3' nuclease activity but lacks a 3'-5' proofreading endonuclease activity. Thus, TaqMan® PCR typically utilizes the 5'-nuclease activity of Taq or Tth polymerase to hydrolyze a hybridization probe bound to its target amplicon, but any enzyme with equivalent 5' nuclease activity can be used. Two oligonucleotide primers are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

TaqMan® RT-PCR can be performed using commercially available equipment, such as, for example, ABI PRISM 7700™ Sequence Detection System™ (Perkin-Elmer-Applied Biosystems, Foster City, Calif., USA), or Lightcycler (Roche Molecular Biochemicals, Mannheim, Germany). In a preferred embodiment, the 5' nuclease procedure is run on a real-time quantitative PCR device such as the ABI PRISM 7700™ Sequence Detection System™. The system consists of a thermocycler, laser, charge-coupled device (CCD), camera and computer. The system amplifies samples in a 96-well format on a thermocycler. During amplification, laser-induced fluorescent signal is collected in real-time through fiber optics cables for all 96 wells, and detected at the CCD. The system includes software for running the instrument and for analyzing the data.

5'-Nuclease assay data are initially expressed as Ct, or the threshold cycle. As discussed above, fluorescence values are recorded during every cycle and represent the amount of product amplified to that point in the amplification reaction. The point when the fluorescent signal is first recorded as statistically significant is the threshold cycle ($C_t$).

To minimize errors and the effect of sample-to-sample variation, RT-PCR is usually performed using an internal standard. The ideal internal standard is expressed at a constant level among different tissues, and is unaffected by the experimental treatment. RNAs most frequently used to normalize patterns of gene expression are mRNAs for the housekeeping genes glyceraldehyde-3-phosphate-dehydrogenase (GAPDH) and β-actin.

A more recent variation of the RT-PCR technique is the real time quantitative PCR, which measures PCR product accumulation through a dual-labeled fluorigenic probe (i.e., TaqMan® probe). Real time PCR is compatible both with quantitative competitive PCR, where internal competitor for each target sequence is used for normalization, and with quantitative comparative PCR using a normalization gene contained within the sample, or a housekeeping gene for RT-PCR. For further details see, e.g. Held et al., *Genome Research* 6:986-994 (1996).

The steps of a representative protocol for profiling gene expression using fixed, paraffin-embedded tissues as the RNA source, including mRNA isolation, purification, primer extension and amplification are given in various published journal articles {for example: T. E. Godfrey et al., *J. Molec. Diagnostics* 2: 84-91 [2000]; K. Specht et al., Am. J. Pathol. 158: 419-29 [2001]}. Briefly, a representative process starts with cutting about 10 μm thick sections of paraffin-embedded tumor tissue samples. The RNA is then extracted, and protein and DNA are removed. After analysis of the RNA concentration, RNA repair and/or amplification steps may be included, if necessary, and RNA is reverse transcribed using gene specific promoters followed by RT-PCR.

According to one aspect of the present invention, PCR primers and probes are designed based upon intron sequences present in the gene to be amplified. In this embodiment, the first step in the primer/probe design is the delineation of intron sequences within the genes. This can be done by publicly available software, such as the DNA BLAT software developed by Kent, W. J., *Genome Res.* 12(4):656-64 (2002), or by the BLAST software including its variations. Subsequent steps follow well established methods of PCR primer and probe design.

In order to avoid non-specific signals, it is important to mask repetitive sequences within the introns when designing the primers and probes. This can be easily accomplished by using the Repeat Masker program available on-line through the Baylor College of Medicine, which screens DNA sequences against a library of repetitive elements and returns a query sequence in which the repetitive elements are masked. The masked intron sequences can then be used to design primer and probe sequences using any commercially or otherwise publicly available primer/probe design packages, such as Primer Express (Applied Biosystems); MGB assay-by-design (Applied Biosystems); Primer3 (Steve Rozen and Helen J. Skaletsky (2000) Primer3 on the WWW for general users and for biologist programmers. In: Krawetz S, Misener S (eds) *Bioinformatics Methods and Protocols: Methods in Molecular Biology*. Humana Press, Totowa, N.J., pp 365-386)

The most important factors considered in PCR primer design include primer length, melting temperature (Tm), and G/C content, specificity, complementary primer sequences, and 3'-end sequence. In general, optimal PCR primers are generally 17-30 bases in length, and contain about 20-80%, such as, for example, about 50-60% G+C bases. Tm's between 50 and 80° C., e.g. about 50 to 70° C. are typically preferred.

For further guidelines for PCR primer and probe design see, e.g. Dieffenbach, C. W. et al., "General Concepts for PCR Primer Design" in: *PCR Primer, A Laboratory Manual*, Cold Spring Harbor Laboratory Press, New York, 1995, pp. 133-155; Innis and Gelfand, "Optimization of PCRs" in: *PCR Protocols, A Guide to Methods and Applications*, CRC Press, London, 1994, pp. 5-11; and Plasterer, T. N. Primerselect: Primer and probe design. *Methods Mol. Biol.* 70:520-527 (1997), the entire disclosures of which are hereby expressly incorporated by reference.

3. Microarrays

Differential gene expression can also be identified, or confirmed using the microarray technique. Thus, the expression profile of breast cancer-associated genes can be measured in either fresh or paraffin-embedded tumor tissue, using microarray technology. In this method, polynucleotide sequences of interest (including cDNAs and oligonucleotides) are plated, or arrayed, on a microchip substrate. The arrayed sequences are then hybridized with specific DNA probes from cells or tissues of interest. Just as in the RT-PCR method, the source of mRNA typically is total RNA isolated from human tumors or tumor cell lines, and corresponding normal tissues or cell lines. Thus RNA can be isolated from a variety of primary tumors or tumor cell lines. If the source of mRNA is a primary tumor, mRNA can be extracted, for example, from frozen or archived paraffin-embedded and fixed (e.g. formalin-fixed) tissue samples, which are routinely prepared and preserved in everyday clinical practice.

In a specific embodiment of the microarray technique, PCR amplified inserts of cDNA clones are applied to a substrate in a dense array. Preferably at least 10,000 nucleotide sequences are applied to the substrate. The microarrayed genes, immobilized on the microchip at 10,000 elements each, are suitable for hybridization under stringent conditions. Fluorescently labeled cDNA probes may be generated through incorporation of fluorescent nucleotides by reverse transcription of RNA extracted from tissues of interest. Labeled cDNA probes applied to the chip hybridize with specificity to each spot of DNA on the array. After stringent washing to remove non-specifically bound probes, the chip is scanned by confocal laser microscopy or by another detection method, such as a CCD camera. Quantitation of hybridization of each arrayed element allows for assessment of corresponding mRNA abundance. With dual color fluorescence, separately labeled cDNA probes generated from two sources of RNA are hybridized pairwise to the array. The relative abundance of the transcripts from the two sources corresponding to each specified gene is thus determined simultaneously. The miniaturized scale of the hybridization affords a convenient and rapid evaluation of the expression pattern for large numbers of genes. Such methods have been shown to have the sensitivity required to detect rare transcripts, which are expressed at a few copies per cell, and to reproducibly detect at least approximately two-fold differences in the expression levels (Schena et al., *Proc. Natl. Acad. Sci. USA* 93(2):106-149 (1996)). Microarray analysis can be performed by commercially available equipment, following manufacturer's protocols, such as by using the Affymetrix GenChip technology, or Incyte's microarray technology.

The development of microarray methods for large-scale analysis of gene expression makes it possible to search systematically for molecular markers of cancer classification and outcome prediction in a variety of tumor types.

4. Serial Analysis of Gene Expression (SAGE)

Serial analysis of gene expression (SAGE) is a method that allows the simultaneous and quantitative analysis of a large number of gene transcripts, without the need of providing an individual hybridization probe for each transcript. First, a short sequence tag (about 10-14 bp) is generated that contains sufficient information to uniquely identify a transcript, provided that the tag is obtained from a unique position within each transcript. Then, many transcripts are linked together to form long serial molecules, that can be sequenced, revealing the identity of the multiple tags simultaneously. The expression pattern of any population of transcripts can be quantitatively evaluated by determining the abundance of individual tags, and identifying the gene corresponding to each tag. For more details see, e.g. Velculescu et al., *Science* 270:484-487 (1995); and Velculescu et al., *Cell* 88:243-51 (1997).

5. MassARRAY Technology

The MassARRAY (Sequenom, San Diego, Calif.) technology is an automated, high-throughput method of gene expression analysis using mass spectrometry (MS) for detection. According to this method, following the isolation of RNA, reverse transcription and PCR amplification, the cDNAs are subjected to primer extension. The cDNA-derived primer extension products are purified, and dipensed on a chip array that is pre-loaded with the components needed for MALTI-TOF MS sample preparation. The various cDNAs present in the reaction are quantitated by analyzing the peak areas in the mass spectrum obtained.

6. Gene Expression Analysis by Massively Parallel Signature Sequencing (MPSS)

This method, described by Brenner et al., *Nature Biotechnology* 18:630-634 (2000), is a sequencing approach that combines non-gel-based signature sequencing with in vitro cloning of millions of templates on separate 5 μm diameter microbeads. First, a microbead library of DNA templates is constructed by in vitro cloning. This is followed by the assembly of a planar array of the template-containing microbeads in a flow cell at a high density (typically greater than $3\times10^6$ microbeads/$cm^2$). The free ends of the cloned templates on each microbead are analyzed simultaneously, using a fluorescence-based signature sequencing method that does not require DNA fragment separation. This method has been shown to simultaneously and accurately provide, in a single operation, hundreds of thousands of gene signature sequences from a yeast cDNA library.

7. Immunohistochemistry

Immunohistochemistry methods are also suitable for detecting the expression levels of the prognostic markers of the present invention. Thus, antibodies or antisera, preferably polyclonal antisera, and most preferably monoclonal antibodies specific for each marker are used to detect expression. The antibodies can be detected by direct labeling of the antibodies themselves, for example, with radioactive labels, fluorescent labels, hapten labels such as, biotin, or an enzyme such as horse radish peroxidase or alkaline phosphatase. Alternatively, unlabeled primary antibody is used in conjunction with a labeled secondary antibody, comprising antisera, polyclonal antisera or a monoclonal antibody specific for the primary antibody. Immunohistochemistry protocols and kits are well known in the art and are commercially available.

8. Proteomics

The term "proteome" is defined as the totality of the proteins present in a sample (e.g. tissue, organism, or cell culture) at a certain point of time. Proteomics includes, among other things, study of the global changes of protein expression in a sample (also referred to as "expression proteomics"). Proteomics typically includes the following steps: (1) separation of individual proteins in a sample by 2-D gel electrophoresis (2-D PAGE); (2) identification of the individual proteins recovered from the gel, e.g. my mass spectrometry or N-terminal sequencing, and (3) analysis of the data using bioinformatics. Proteomics methods are valuable supplements to other methods of gene expression profiling, and can be used, alone or in combination with other methods, to detect the products of the prognostic markers of the present invention.

9. General Description of the mRNA Isolation, Purification and Amplification

The steps of a representative protocol for profiling gene expression using fixed, paraffin-embedded tissues as the RNA source, including mRNA isolation, purification, primer extension and amplification are given in various published journal articles {for example: T. E. Godfrey et al. J. Molec. Diagnostics 2: 84-91 [2000]; K. specht et al., Am. J. Pathol. 158: 419-29 [2001]}. Briefly, a representative process starts with cutting about 10 μm thick sections of paraffin-embedded tumor tissue samples. The RNA is then extracted, and protein and DNA are removed. After analysis of the RNA concentration, RNA repair and/or amplification steps may be included, if necessary, and RNA is reverse transcribed using gene specific promoters followed by RT-PCR. Finally, the data are analyzed to identify the best treatment option(s) available to the patient on the basis of the characteristic gene expression pattern identified in the tumor sample examined.

10. Breast Cancer Gene Set, Assayed Gene Subsequences, and Clinical Application of Gene Expression Data An important aspect of the present invention is to use the measured expression of certain genes by breast cancer tissue to provide prognostic information. For this purpose it is necessary to correct for (normalize away) both differences in the amount of RNA assayed and variability in the quality of the RNA used. Therefore, the assay typically measures and incorporates the expression of certain normalizing genes, including well known housekeeping genes, such as GAPDH and Cyp1. Alternatively, normalization can be based on the mean or median signal (Ct) of all of the assayed genes or a large subset thereof (global normalization approach). On a gene-by-gene basis, measured normalized amount of a patient tumor mRNA is compared to the amount found in a breast cancer tissue reference set. The number (N) of breast cancer tissues in this reference set should be sufficiently high to ensure that different reference sets (as a whole) behave essentially the same way. If this condition is met, the identity of the individual breast cancer tissues present in a particular set will have no significant impact on the relative amounts of the genes assayed. Usually, the breast cancer tissue reference set consists of at least about 30, preferably at least about 40 different FPE breast cancer tissue specimens. Unless noted otherwise, normalized expression levels for each mRNA/tested tumor/patient will be expressed as a percentage of the expression level measured in the reference set. More specifically, the reference set of a sufficiently high number (e.g. 40) of tumors yields a distribution of normalized levels of each mRNA species. The level measured in a particular tumor sample to be analyzed falls at some percentile within this range, which can be determined by methods well known in the art. Below, unless noted otherwise, reference to expression levels of a gene assume normalized expression relative to the reference set although this is not always explicitly stated.

Further details of the invention will be described in the following non-limiting Example

EXAMPLE

A Phase II Study of Gene Expression in 79 Malignant Breast Tumors

A gene expression study was designed and conducted with the primary goal to molecularly characterize gene expression in paraffin-embedded, fixed tissue samples of invasive breast ductal carcinoma, and to explore the correlation between such molecular profiles and disease-free survival.

Study Design

Molecular assays were performed on paraffin-embedded, formalin-fixed primary breast tumor tissues obtained from 79 individual patients diagnosed with invasive breast cancer. All patients in the study had 10 or more positive nodes. Mean age was 57 years, and mean clinical tumor size was 4.4 cm. Patients were included in the study only if histopathologic assessment, performed as described in the Materials and Methods section, indicated adequate amounts of tumor tissue and homogeneous pathology.

Materials and Methods

Each representative tumor block was characterized by standard histopathology for diagnosis, semi-quantitative assessment of amount of tumor, and tumor grade. A total of 6 sections (10 microns in thickness each) were prepared and placed in two Costar Brand Microcentrifuge Tubes (Polypropylene, 1.7 mL tubes, clear; 3 sections in each tube). If the tumor constituted less than 30% of the total specimen area, the sample may have been crudely dissected by the pathologist, using gross microdissection, putting the tumor tissue directly into the Costar tube.

If more than one tumor block was obtained as part of the surgical procedure, the block most representative of the pathology was used for analysis.

Gene Expression Analysis mRNA was extracted and purified from fixed, paraffin-embedded tissue samples, and prepared for gene expression analysis as described in section 9 above.

Molecular assays of quantitative gene expression were performed by RT-PCR, using the ABI PRISM 7900™ Sequence Detection System™ (Perkin-Elmer-Applied Biosystems, Foster City, Calif., USA). ABI PRISM 7900™ consists of a thermocycler, laser, charge-coupled device (CCD), camera and computer. The system amplifies samples in a 384-well format on a thermocycler. During amplification, laser-induced fluorescent signal is collected in real-time through fiber optics cables for all 384 wells, and detected at the CCD. The system includes software for running the instrument and for analyzing the data.

Analysis and Results

Tumor tissue was analyzed for 185 cancer-related genes and 7 reference genes. The threshold cycle (CT) values for each patient were normalized based on the median of the 7 reference genes for that particular patient. Clinical outcome data were available for all patients from a review of registry data and selected patient charts.

Outcomes were classified as:

0 died due to breast cancer or to unknown cause or alive with breast cancer recurrence;

1 alive without breast cancer recurrence or died due to a cause other than breast cancer Analysis was performed by:

1. Analysis of the relationship between normalized gene expression and the binary outcomes of 0 or 1.
2. Analysis of the relationship between normalized gene expression and the time to outcome (0 or 1 as defined above) where patients who were alive without breast cancer recurrence or who died due to a cause other than breast cancer were censored. This approach was used to evaluate the prognostic impact of individual genes and also sets of multiple genes.

Analysis of Patients with Invasive Breast Carcinoma by Binary Approach

In the first (binary) approach, analysis was performed on all 79 patients with invasive breast carcinoma. At t test was performed on the groups of patients classified as either no recurrence and no breast cancer related death at three years, versus recurrence, or breast cancer-related death at three years, and the p-values for the differences between the groups for each gene were calculated.

Table 1 lists the 47 genes for which the p-value for the differences between the groups was <0.10. The first column of mean expression values pertains to patients who neither had a metastatic recurrence of nor died from breast cancer. The second column of mean expression values pertains to patients who either had a metastatic recurrence of or died from breast cancer.

TABLE 1

| | Mean | Mean | t-value | df | p | Valid N | Valid N |
|---|---|---|---|---|---|---|---|
| Bcl2 | −0.15748 | −1.22816 | 4.00034 | 75 | 0.000147 | 35 | 42 |
| PR | −2.67225 | −5.49747 | 3.61540 | 75 | 0.000541 | 35 | 42 |
| IGF1R | −0.59390 | −1.71506 | 3.49158 | 75 | 0.000808 | 35 | 42 |
| BAG1 | 0.18844 | −0.68509 | 3.42973 | 75 | 0.000985 | 35 | 42 |
| CD68 | −0.52275 | 0.10983 | −3.41186 | 75 | 0.001043 | 35 | 42 |
| EstR1 | −0.35581 | −3.00699 | 3.32190 | 75 | 0.001384 | 35 | 42 |
| CTSL | −0.64894 | −0.09204 | −3.26781 | 75 | 0.001637 | 35 | 42 |
| IGFBP2 | −0.81181 | −1.78398 | 3.24158 | 75 | 0.001774 | 35 | 42 |
| GATA3 | 1.80525 | 0.57428 | 3.15608 | 75 | 0.002303 | 35 | 42 |
| TP53BP2 | −4.71118 | −6.09289 | 3.02888 | 75 | 0.003365 | 35 | 42 |
| EstR1 | 3.67801 | 1.64693 | 3.01073 | 75 | 0.003550 | 35 | 42 |
| CEGP1 | −2.02566 | −4.25537 | 2.85620 | 75 | 0.005544 | 35 | 42 |
| SURV | −3.67493 | −2.96982 | −2.70544 | 75 | 0.008439 | 35 | 42 |
| p27 | 0.80789 | 0.28807 | 2.55401 | 75 | 0.012678 | 35 | 42 |
| Chk1 | −3.37981 | −2.80389 | −2.46979 | 75 | 0.015793 | 35 | 42 |
| BBC3 | −4.71789 | −5.62957 | 2.46019 | 75 | 0.016189 | 35 | 42 |
| ZNF217 | 1.10038 | 0.62730 | 2.42282 | 75 | 0.017814 | 35 | 42 |
| EGFR | −2.88172 | −2.20556 | −2.34774 | 75 | 0.021527 | 35 | 42 |
| CD9 | 1.29955 | 0.91025 | 2.31439 | 75 | 0.023386 | 35 | 42 |
| MYBL2 | −3.77489 | −3.02193 | −2.29042 | 75 | 0.024809 | 35 | 42 |
| HIF1A | −0.44248 | 0.03740 | −2.25950 | 75 | 0.026757 | 35 | 42 |
| GRB7 | −1.96063 | −1.05007 | −2.25801 | 75 | 0.026854 | 35 | 42 |
| pS2 | −1.00691 | −3.13749 | 2.24070 | 75 | 0.028006 | 35 | 42 |
| RIZ1 | −7.62149 | −8.38750 | 2.20226 | 75 | 0.030720 | 35 | 42 |
| ErbB3 | −6.89508 | −7.44326 | 2.16127 | 75 | 0.033866 | 35 | 42 |
| TOP2B | 0.45122 | 0.12665 | 2.14616 | 75 | 0.035095 | 35 | 42 |
| MDM2 | 1.09049 | 0.69001 | 2.10967 | 75 | 0.038223 | 35 | 42 |
| PRAME | −6.40074 | −7.70424 | 2.08126 | 75 | 0.040823 | 35 | 42 |
| GUS | −1.51683 | −1.89280 | 2.05200 | 75 | 0.043661 | 35 | 42 |
| RAD51C | −5.85618 | −6.71334 | 2.04575 | 75 | 0.044288 | 35 | 42 |
| AIB1 | −3.08217 | −2.28784 | −2.00600 | 75 | 0.048462 | 35 | 42 |
| STK15 | −3.11307 | −2.59454 | −2.00321 | 75 | 0.048768 | 35 | 42 |
| GAPDH | −0.35829 | −0.02292 | −1.94326 | 75 | 0.055737 | 35 | 42 |
| FHIT | −3.00431 | −3.67175 | 1.86927 | 75 | 0.065489 | 35 | 42 |
| KRT19 | 2.52397 | 2.01694 | 1.85741 | 75 | 0.067179 | 35 | 42 |
| TS | −2.83607 | −2.29048 | −1.83712 | 75 | 0.070153 | 35 | 42 |
| GSTM1 | −3.69140 | −4.38623 | 1.83397 | 75 | 0.070625 | 35 | 42 |
| G-Catenin | 0.31875 | −0.15524 | 1.80823 | 75 | 0.074580 | 35 | 42 |
| AKT2 | 0.78858 | 0.46703 | 1.79276 | 75 | 0.077043 | 35 | 42 |
| CCNB1 | −4.26197 | −3.51628 | −1.78803 | 75 | 0.077810 | 35 | 42 |
| PI3KC2A | −2.27401 | −2.70265 | 1.76748 | 75 | 0.081215 | 35 | 42 |
| FBXO5 | −4.72107 | −4.24411 | −1.75935 | 75 | 0.082596 | 35 | 42 |
| DR5 | −5.80850 | −6.55501 | 1.74345 | 75 | 0.085353 | 35 | 42 |
| CIAP1 | −2.81825 | −3.09921 | 1.72480 | 75 | 0.088683 | 35 | 42 |
| MCM2 | −2.87541 | −2.50683 | −1.72061 | 75 | 0.089445 | 35 | 42 |
| CCND1 | 1.30995 | 0.80905 | 1.68794 | 75 | 0.095578 | 35 | 42 |
| EIF4E | −5.37657 | −6.47156 | 1.68169 | 75 | 0.096788 | 35 | 42 |

In the foregoing Table 1, negative t-values indicate higher expression, associated with worse outcomes, and, inversely, higher (positive) t-values indicate higher expression associated with better outcomes. Thus, for example, elevated expression of the CD68 gene (t-value=−3.41, CT mean alive<CT mean deceased) indicates a reduced likelihood of disease free survival. Similarly, elevated expression of the BCl2 gene (t-value=4.00; CT mean alive>CT mean deceased) indicates an increased likelihood of disease free survival.

Based on the data set forth in Table 1, the expression of any of the following genes in breast cancer above a defined expression threshold indicates a reduced likelihood of survival without cancer recurrence following surgery: Grb7, CD68, CTSL, Chk1, Her2, STK15, AIB1, SURV, EGFR, MYBL2, HIF1α.

Based on the data set forth in Table 1, the expression of any of the following genes in breast cancer above a defined expression threshold indicates a better prognosis for survival without cancer recurrence following surgery: TP53BP2, PR, Bc12, KRT14, EstR1, IGFBP2, BAG1, CEGP1, KLK10, β Catenin, GSTM1, FHIT, Riz1, IGF1, BBC3, IGFR1, TBP, p2'7, IRS1, IGF1R, GATA3, CEGP1, ZNF217, CD9, pS2, ErbB3, TOP2B, MDM2, RAD51, and KRT19.

Analysis of ER Positive Patients by Binary Approach 57 patients with normalized CT for estrogen receptor (ER) >0 (i.e., ER positive patients) were subjected to separate analysis. At test was performed on the two groups of patients classified as either no recurrence and no breast cancer related death at three years, or recurrence or breast cancer-related death at three years, and the p-values for the differences between the groups for each gene were calculated. Table 2, below, lists the genes where the p-value for the differences between the groups was <0.105. The first column of mean expression values pertains to patients who neither had a metastatic recurrence nor died from breast cancer. The second column of mean expression values pertains to patients who either had a metastatic recurrence of or died from breast cancer.

TABLE 2

| | Mean | Mean | t-value | df | p | Valid N | Valid N |
|---|---|---|---|---|---|---|---|
| IGF1R | −0.13975 | −1.00435 | 3.65063 | 55 | 0.000584 | 30 | 27 |
| Bcl2 | 0.15345 | −0.70480 | 3.55488 | 55 | 0.000786 | 30 | 27 |
| CD68 | −0.54779 | 0.19427 | −3.41818 | 55 | 0.001193 | 30 | 27 |
| HNF3A | 0.39617 | −0.63802 | 3.20750 | 55 | 0.002233 | 30 | 27 |
| CTSL | −0.66726 | 0.00354 | −3.20692 | 55 | 0.002237 | 30 | 27 |
| TP53BP2 | −4.81858 | −6.44425 | 3.13698 | 55 | 0.002741 | 30 | 27 |
| GATA3 | 2.33386 | 1.40803 | 3.02958 | 55 | 0.003727 | 30 | 27 |
| BBC3 | −4.54979 | −5.72333 | 2.91943 | 55 | 0.005074 | 30 | 27 |
| RAD51C | −5.63363 | −6.94841 | 2.85475 | 55 | 0.006063 | 30 | 27 |
| BAG1 | 0.31087 | −0.50669 | 2.61524 | 55 | 0.011485 | 30 | 27 |
| IGFBP2 | −0.49300 | −1.30983 | 2.59121 | 55 | 0.012222 | 30 | 27 |
| FBXO5 | −4.86333 | −4.05564 | −2.56325 | 55 | 0.013135 | 30 | 27 |
| EstR1 | 0.68368 | −0.66555 | 2.56090 | 55 | 0.013214 | 30 | 27 |
| PR | −1.89094 | −3.86602 | 2.52803 | 55 | 0.014372 | 30 | 27 |
| SURV | −3.87857 | −3.10970 | −2.49622 | 55 | 0.015579 | 30 | 27 |
| CD9 | 1.41691 | 0.91725 | 2.43043 | 55 | 0.018370 | 30 | 27 |
| RB1 | −2.51662 | −2.97419 | 2.41221 | 55 | 0.019219 | 30 | 27 |
| EPHX1 | −3.91703 | −5.85097 | 2.29491 | 55 | 0.025578 | 30 | 27 |
| CEGP1 | −1.18600 | −2.95139 | 2.26608 | 55 | 0.027403 | 30 | 27 |
| CCNB1 | −4.44522 | −3.35763 | −2.25148 | 55 | 0.028370 | 30 | 27 |
| TRAIL | 0.34893 | −0.56574 | 2.20372 | 55 | 0.031749 | 30 | 27 |
| EstR1 | 4.60346 | 3.60340 | 2.20223 | 55 | 0.031860 | 30 | 27 |
| DR5 | −5.71827 | −6.79088 | 2.14548 | 55 | 0.036345 | 30 | 27 |
| MCM2 | −2.96800 | −2.48458 | −2.10518 | 55 | 0.039857 | 30 | 27 |
| Chk1 | −3.46968 | −2.85708 | −2.08597 | 55 | 0.041633 | 30 | 27 |
| p27 | 0.94714 | 0.49656 | 2.04313 | 55 | 0.045843 | 30 | 27 |
| MYBL2 | −3.97810 | −3.14837 | −2.02921 | 55 | 0.047288 | 30 | 27 |
| GUS | −1.42486 | −1.82900 | 1.99758 | 55 | 0.050718 | 30 | 27 |
| P53 | −1.08810 | −1.47193 | 1.92087 | 55 | 0.059938 | 30 | 27 |
| HIF1A | −0.40925 | 0.11688 | −1.91278 | 55 | 0.060989 | 30 | 27 |
| cMet | −6.36835 | −5.58479 | −1.88318 | 55 | 0.064969 | 30 | 27 |
| EGFR | −2.95785 | −2.28105 | −1.86840 | 55 | 0.067036 | 30 | 27 |
| MTA1 | −7.55365 | −8.13656 | 1.81479 | 55 | 0.075011 | 30 | 27 |
| RIZ1 | −7.52785 | −8.25903 | 1.79518 | 55 | 0.078119 | 30 | 27 |
| ErbB3 | −6.62488 | −7.10826 | 1.79255 | 55 | 0.078545 | 30 | 27 |
| TOP2B | 0.54974 | 0.27531 | 1.74888 | 55 | 0.085891 | 30 | 27 |
| EIF4E | −5.06603 | −6.31426 | 1.68030 | 55 | 0.098571 | 30 | 27 |
| TS | −2.95042 | −2.36167 | −1.67324 | 55 | 0.099959 | 30 | 27 |
| STK15 | −3.25010 | −2.72118 | −1.64822 | 55 | 0.105010 | 30 | 27 |

For each gene, a classification algorithm was utilized to identify the best threshold value (CT) for using each gene alone in predicting clinical outcome.

Based on the data set forth in Table 2, expression of the following genes in ER-positive cancer above a defined expression level is indicative of a reduced likelihood of survival without cancer recurrence following surgery: CD68; CTSL; FBXO5; SURV; CCNB1; MCM2; Chk1; MYBL2; HIF1A; cMET; EGFR; TS; STK15. Many of these genes (CD68, CTSL, SURV, CCNB1, MCM2, Chk1, MYBL2, EGFR, and STK15) were also identified as indicators of poor prognosis in the previous analysis, not limited to ER-positive breast cancer. Based on the data set forth in Table 2, expression of the following genes in ER-positive cancer above a defined expression level is indicative of a better prognosis for survival without cancer recurrence following surgery: IGFR1; BCl2; HNF3A; TP53BP2; GATA3; BBC3; RAD51C; BAG1; IGFBP2; PR; CD9; RB1; EPHX1; CEGP1; TRAIL; DR5; p2'7; p53; MTA; RIZ1; ErbB3; TOP2B; EIF4E. Of the latter genes, IGFR1; BCl2; TP53BP2; GATA3; BBC3; RAD51C; BAG1; IGFBP2; PR; CD9; CEGP1; DR5; p27; RIZ1; ErbB3; TOP2B; EIF4E have also been identified as indicators of good prognosis in the previous analysis, not limited to ER-positive breast cancer.

Analysis of ER Negative Patients by Binary Approach

Twenty patients with normalized CT for estrogen receptor (ER)<1.6 (i.e., ER negative patients) were subjected to separate analysis. At test was performed on the two groups of patients classified as either no recurrence and no breast cancer related death at three years, or recurrence or breast cancer-related death at three years, and the p-values for the differences between the groups for each gene were calculated. Table 3 lists the genes where the p-value for the differences between the groups was <0.118. The first column of mean expression values pertains to patients who neither had a metastatic recurrence nor died from breast cancer. The second column of mean expression values pertains to patients who either had a metastatic recurrence of or died from breast cancer.

TABLE 3

| | Mean | Mean | t-value | df | p | Valid N | Valid N |
|---|---|---|---|---|---|---|---|
| KRT14 | −1.95323 | −6.69231 | 4.03303 | 18 | 0.000780 | 5 | 15 |
| KLK10 | −2.68043 | −7.11288 | 3.10321 | 18 | 0.006136 | 5 | 15 |
| CCND1 | −1.02285 | 0.03732 | −2.77992 | 18 | 0.012357 | 5 | 15 |
| Upa | −0.91272 | −0.04773 | −2.49460 | 18 | 0.022560 | 5 | 15 |
| HNF3A | −6.04780 | −2.36469 | −2.43148 | 18 | 0.025707 | 5 | 15 |
| Maspin | −3.56145 | −6.18678 | 2.40169 | 18 | 0.027332 | 5 | 15 |
| CDH1 | −3.54450 | −2.34984 | −2.38755 | 18 | 0.028136 | 5 | 15 |
| HER2 | −1.48973 | 1.53108 | −2.35826 | 18 | 0.029873 | 5 | 15 |
| GRB7 | −2.55289 | 0.00036 | −2.32890 | 18 | 0.031714 | 5 | 15 |
| AKT1 | −0.36849 | 0.46222 | −2.29737 | 18 | 0.033807 | 5 | 15 |
| TGFA | −4.03137 | −5.67225 | 2.28546 | 18 | 0.034632 | 5 | 15 |
| FRP1 | 1.45776 | −1.39459 | 2.27884 | 18 | 0.035097 | 5 | 15 |
| STMY3 | −1.59610 | −0.26305 | −2.23191 | 18 | 0.038570 | 5 | 15 |
| Contig 27882 | −4.27585 | −7.34338 | 2.18700 | 18 | 0.042187 | 5 | 15 |
| A-Catenin | −1.19790 | −0.39085 | −2.15624 | 18 | 0.044840 | 5 | 15 |
| VDR | −4.37823 | −2.37167 | −2.15620 | 18 | 0.044844 | 5 | 15 |
| GRO1 | −3.65034 | −5.97002 | 2.12286 | 18 | 0.047893 | 5 | 15 |
| MCM3 | −3.86041 | −5.55078 | 2.10030 | 18 | 0.050061 | 5 | 15 |
| B-actin | 4.69672 | 5.19190 | −2.04951 | 18 | 0.055273 | 5 | 15 |
| HIF1A | −0.64183 | −0.10566 | −2.02301 | 18 | 0.058183 | 5 | 15 |
| MMP9 | −8.90613 | −7.35163 | −1.88747 | 18 | 0.075329 | 5 | 15 |
| VEGF | 0.37904 | 1.10778 | −1.87451 | 18 | 0.077183 | 5 | 15 |
| PRAME | −4.95855 | −7.41973 | 1.86668 | 18 | 0.078322 | 5 | 15 |
| AIB1 | −3.12245 | −1.92934 | −1.86324 | 18 | 0.078829 | 5 | 15 |
| KRT5 | −1.32418 | −3.62027 | 1.85919 | 18 | 0.079428 | 5 | 15 |
| KRT18 | 1.08383 | 2.25369 | −1.83831 | 18 | 0.082577 | 5 | 15 |
| KRT17 | −0.69073 | −3.56536 | 1.78449 | 18 | 0.091209 | 5 | 15 |
| P14ARF | −1.87104 | −3.36534 | 1.63923 | 18 | 0.118525 | 5 | 15 |

Based on the data set forth in Table 3, expression of the following genes in ER-negative cancer above a defined expression level is indicative of a reduced likelihood of survival without cancer recurrence ($p<0.05$): CCND1; UPA; HNF3A; CDH1; Her2; GRB7; AKT1; STMY3; α-Catenin; VDR; GRO1. Only 2 of these genes (Her2 and Grb7) were also identified as indicators of poor prognosis in the previous analysis, not limited to ER-negative breast cancer. Based on the data set forth in Table 3, expression of the following genes in ER-negative cancer above a defined expression level is indicative of a better prognosis for survival without cancer recurrence (KT14; KLK10; Maspin, TGFα, and FRP1. Of the latter genes, only KLK10 has been identified as an indicator of good prognosis in the previous analysis, not limited to ER-negative breast cancer.

Analysis of Multiple Genes and Indicators of Outcome

Two approaches were taken in order to determine whether using multiple genes would provide better discrimination between outcomes.

First, a discrimination analysis was performed using a forward stepwise approach. Models were generated that classified outcome with greater discrimination than was obtained with any single gene alone.

According to a second approach (time-to-event approach), for each gene a Cox Proportional Hazards model (see, e.g. Cox, D. R., and Oakes, D. (1984), *Analysis of Survival Data*, Chapman and Hall, London, New York) was defined with time to recurrence or death as the dependent variable, and the expression level of the gene as the independent variable. The genes that have a p-value<0.10 in the Cox model were identified. For each gene, the Cox model provides the relative risk (RR) of recurrence or death for a unit change in the expression of the gene. One can choose to partition the patients into subgroups at any threshold value of the measured expression (on the CT scale), where all patients with expression values above the threshold have higher risk, and all patients with expression values below the threshold have lower risk, or vice versa, depending on whether the gene is an indicator of bad (RR>1.01) or good (RR<1.01) prognosis. Thus, any threshold value will define subgroups of patients with respectively increased or decreased risk. The results are summarized in Table 4. The third column, with the heading: exp(coef), shows RR values.

TABLE 4

| Gene | coef | exp(coef) | se(coef) | z | p |
|---|---|---|---|---|---|
| TP53BP2 | −0.21892 | 0.803386 | 0.068279 | −3.20625 | 0.00134 |
| GRB7 | 0.235697 | 1.265791 | 0.073541 | 3.204992 | 0.00135 |
| PR | −0.10258 | 0.90251 | 0.035864 | −2.86018 | 0.00423 |
| CD68 | 0.465623 | 1.593006 | 0.167785 | 2.775115 | 0.00552 |
| Bcl2 | −0.26769 | 0.765146 | 0.100785 | −2.65603 | 0.00791 |
| KRT14 | −0.11892 | 0.887877 | 0.046938 | −2.53359 | 0.0113 |
| PRAME | −0.13707 | 0.871912 | 0.054904 | −2.49649 | 0.0125 |
| CTSL | 0.431499 | 1.539564 | 0.185237 | 2.329444 | 0.0198 |
| EstR1 | −0.07686 | 0.926018 | 0.034848 | −2.20561 | 0.0274 |
| Chk1 | 0.284466 | 1.329053 | 0.130823 | 2.174441 | 0.0297 |
| IGFBP2 | −0.2152 | 0.806376 | 0.099324 | −2.16669 | 0.0303 |
| HER2 | 0.155303 | 1.168011 | 0.072633 | 2.13818 | 0.0325 |
| BAG1 | −0.22695 | 0.796959 | 0.106377 | −2.13346 | 0.0329 |
| CEGP1 | −0.07879 | 0.924236 | 0.036959 | −2.13177 | 0.033 |
| STK15 | 0.27947 | 1.322428 | 0.132762 | 2.105039 | 0.0353 |
| KLK10 | −0.11028 | 0.895588 | 0.05245 | −2.10248 | 0.0355 |
| B. Catenin | −0.16536 | 0.847586 | 0.084796 | −1.95013 | 0.0512 |
| EstR1 | −0.0803 | 0.922842 | 0.042212 | −1.90226 | 0.0571 |
| GSTM1 | −0.13209 | 0.876266 | 0.072211 | −1.82915 | 0.0674 |
| TOP2A | −0.11148 | 0.894512 | 0.061855 | −1.80222 | 0.0715 |
| AIB1 | 0.152968 | 1.165288 | 0.086332 | 1.771861 | 0.0764 |
| FHIT | −0.15572 | 0.855802 | 0.088205 | −1.7654 | 0.0775 |
| RIZ1 | −0.17467 | 0.839736 | 0.099464 | −1.75609 | 0.0791 |
| SURV | 0.185784 | 1.204162 | 0.106625 | 1.742399 | 0.0814 |
| IGF1 | −0.10499 | 0.900338 | 0.060482 | −1.73581 | 0.0826 |
| BBC3 | −0.1344 | 0.874243 | 0.077613 | −1.73163 | 0.0833 |
| IGF1R | −0.13484 | 0.873858 | 0.077889 | −1.73115 | 0.0834 |
| DIABLO | 0.284336 | 1.32888 | 0.166556 | 1.707148 | 0.0878 |
| TBP | −0.34404 | 0.7089 | 0.20564 | −1.67303 | 0.0943 |
| p27 | −0.26002 | 0.771033 | 0.1564 | −1.66256 | 0.0964 |
| IRS1 | −0.07585 | 0.926957 | 0.046096 | −1.64542 | 0.0999 |

The binary and time-to-event analyses, with few exceptions, identified the same genes as prognostic markers. For example, comparison of Tables 1 and 4 shows that 10 genes were represented in the top 15 genes in both lists. Furthermore, when both analyses identified the same gene at [p<0.10], which happened for 21 genes, they were always concordant with respect to the direction (positive or negative sign) of the correlation with survival/recurrence. Overall, these results strengthen the conclusion that the identified markers have significant prognostic value.

For Cox models comprising more than two genes (multivariate models), stepwise entry of each individual gene into the model is performed, where the first gene entered is pre-selected from among those genes having significant univariate p-values, and the gene selected for entry into the model at each subsequent step is the gene that best improves the fit of the model to the data. This analysis can be performed with any total number of genes. In the analysis the results of which are shown below, stepwise entry was performed for up to 10 genes.

Multivariate analysis is performed using the following equation:

$$RR=\exp[\text{coef}(\text{gene}A)\times Ct(\text{gene}A)+\text{coef}(\text{gene}B)\times Ct(\text{gene}B)+\text{coef}(\text{gene}C)\times Ct(\text{gene}C)+].$$

In this equation, coefficients for genes that are predictors of beneficial outcome are positive numbers and coefficients for genes that are predictors of unfavorable outcome are negative numbers. The "Ct" values in the equation are ΔCts, i.e. reflect the difference between the average normalized Ct value for a population and the normalized Ct measured for the patient in question. The convention used in the present analysis has been that ΔCts below and above the population average have positive signs and negative signs, respectively (reflecting greater or lesser mRNA abundance). The relative risk (RR) calculated by solving this equation will indicate if the patient has an enhanced or reduced chance of long-term survival without cancer recurrence.

Multivariate Gene Analysis of 79 Patients with Invasive Breast Carcinoma

A multivariate stepwise analysis, using the Cox Proportional Hazards Model, was performed on the gene expression data obtained for all 79 patients with invasive breast carcinoma. The following ten-gene sets have been identified by this analysis as having particularly strong predictive value of patient survival:

(a) TP53BP2, Bc12, BAD, EPHX1, PDGFRβ, DIABLO, XIAP, YB1, CA9, and KRT8.
(b) GRB7, CD68, TOP2A, Bcl2, DIABLO, CD3, 1D1, PPM1D, MCM6, and WISP1.
(c) PR, TP53BP2, PRAME, DIABLO, CTSL, IGFBP2, TIMP1, CA9, MMP9, and COX2.
(d) CD68, GRB7, TOP2A, Bc12, DIABLO, CD3, 1D1, PPM1D, MCM6, and WISP1.
(e) Bc12, TP53BP2, BAD, EPHX1, PDGFRβ, DIABLO, XIAP, YB1, CA9, and KRT8.
(f) KRT14, KRT5, PRAME, TP53BP2, GUS1, AIB1, MCM3, CCNE1, MCM6, and ID1.
(g) PRAME, TP53BP2, EstR1, DIABLO, CTSL, PPM1D, GRB7, DAPK1, BBC3, and VEGFB.
(h) CTSL2, GRB7, TOP2A, CCNB1, Bc12, DIABLO, PRAME, EMS1, CA9, and EpCAM.
(i) EstR1, TP53BP2, PRAME, DIABLO, CTSL, PPM1D, GRB7, DAPK1, BBC3, and VEGFB.
(k) Chk1, PRAME, p53BP2, GRB7, CA9, CTSL, CCNB1, TOP2A, tumor size, and IGFBP2.
(l) IGFBP2, GRB7, PRAME, DIABLO, CTSL, β-Catenin, PPM1D, Chk1, WISP1, and LOT1.
(m) HER2, TP53BP2, Bc12, DIABLO, TIMP1, EPHX1, TOP2A, TRAIL, CA9, and AREG.
(n) BAG1, TP53BP2, PRAME, IL6, CCNB1, PAI1, AREG, tumor size, CA9, and Ki67.
(o) CEGP1, TP53BP2, PRAME, DIABLO, Bc12, COX2, CCNE1, STK15, and AKT2, and FGF18.
(p) STK15, TP53BP2, PRAME, 1L6, CCNE1, AKT2, DIABLO, cMet, CCNE2, and COX2.
(q) KLK10, EstR1, TP53BP2, PRAME, DIABLO, CTSL, PPM1D, GRB7, DAPK1, and BBC3.
(r) AIB1, TP53BP2, Bc12, DIABLO, TIMP1, CD3, p53, CA9, GRB7, and EPHX1
(s) BBC3, GRB7, CD68, PRAME, TOP2A, CCNB1, EPHX1, CTSL GSTM1, and APC.
(t) CD9, GRB7, CD68, TOP2A, Bc12, CCNB1, CD3, DIABLO, ID1, and PPM1D.
(w) EGFR, KRT14, GRB7, TOP2A, CCNB1, CTSL, Bc12, TP, KLK10, and CA9.
(x) HIF1α, PR, DIABLO, PRAME, Chk1, AKT2, GRB7, CCNE1, TOP2A, and CCNB1.
(y) MDM2, TP53BP2, DIABLO, Bc12, AIB1, TEMP1, CD3, p53, CA9, and HER2.
(z) MYBL2, TP53BP2, PRAME, IL6, Bcl2, DIABLO, CCNE1, EPHX1, TIMP1, and CA9.
(aa) p27, TP53BP2, PRAME, DIABLO, Bc12, COX2, CCNE1, STK15, AKT2, and ID1.
(ab) RAD51, GRB7, CD68, TOP2A, CIAP2, CCNB1, BAG1, IL6, FGFR1, and TP53BP2.
(ac) SURV, GRB7, TOP2A, PRAME, CTSL, GSTM1, CCNB1, VDR, CA9, and CCNE2.
(ad) TOP2B, TP53BP2, DIABLO, Bc12, TIMP1, AIB1, CA9, p53, KRT8, and BAD.
(ae) ZNF217, GRB7, p53BP2, PRAME, DIABLO, Bc12, COX2, CCNE1, APC4, and β-Catenin.

While the present invention has been described with reference to what are considered to be the specific embodiments, it is to be understood that the invention is not limited to such embodiments. To the contrary, the invention is intended to cover various modifications and equivalents included within the spirit and scope of the appended claims. For example, while the disclosure focuses on the identification of various breast cancer associated genes and gene sets, and on the personalized prognosis of breast cancer, similar genes, gene sets and methods concerning other types of cancer are specifically within the scope herein.

All references cited throughout the disclosure are hereby expressly incorporated by reference.

TABLE 5A

| Gene | Accession | Seq | SEQ ID NO: |
|---|---|---|---|
| AIB1 | NM_006534 | GCGGCGAGTTTCCGATTTAAAGCTGAGCTGCGAGGAAAATGGCGGCGGGAGGATCAAAATACTTGCTGGAT GGTGGACTCA | 1 |
| AKT1 | NM_005163 | CGCTTCTATGGCGCTGAGATTGTGTCAGCCCTGGACTACCTGCACTCGGAGAAGAACGTGGTGTACCGGGA | 2 |

TABLE 5A-continued

| Gene | Accession | Seq | SEQ ID NO: |
|---|---|---|---|
| AKT2 | NM_001626 | TCCTGCCACCCTTCAAACCTCAGGTCACGTCCGAGGTCGACACAAGGTACTTCGATGATGAATTTACCGCC | 3 |
| APC | NM_000038 | GGACAGCAGGAATGTGTTTCTCCATACAGGTCACGGGGAGCCAATGGTTCAGAAACAAATCGAGTGGGT | 4 |
| AREG | NM_001657 | TGTGAGTGAAATGCCTTCTAGTAGTGAACCGTCCTCGGGAGCCGACTATGACTACTCAGAAGAGTATGATA ACGAACCACAA | 5 |
| B-actin | NM_001101 | CAGCAGATGTGGATCAGCAAGCAGGAGTATGACGAGTCCGGCCCCTCCATCGTCCACCGCAAATGC | 6 |
| B-Catenin | NM_001904 | GGCTCTTGTGCGTACTGTCCTTCGGGCTGGTGACAGGGAAGACATCACTGAGCCTGCCATCTGTGCTCTTC GTCATCTGA | 7 |
| BAD | NM_032989 | GGGTCAGGTGCCTCGAGATCGGGCTTGGGCCCAGAGCATGTTCCAGATCCCAGAGTTTGAGCCGAGTGAGCAG | 8 |
| BAG1 | NM_004323 | CGTTGTCAGCACTTGGAATACAAGATGGTTGCCGGGTCATGTTAATTGGGAAAAAGAACAGTCCACAGGAA GAGGTTGAAC | 9 |
| BBC3 | NM_014417 | CCTGGAGGGTCCTGTACAATCTCATCATGGGACTCCTGCCCTTACCCAGGGGCCACAGAGCCCCCGAGATG GAGCCCAATTAG | 10 |
| Bcl2 | NM_000633 | CAGATGGACCTAGTACCCACTGAGATTTCCACGCCGAAGGACAGCGATGGGAAAAATGCCCTTAAATCATAGG | 11 |
| CA9 | NM_001216 | ATCCTAGCCCTGGTTTTTGGCCTCCTTTTTGCTGTCACCAGCGTCGCGTTCCTTGTGCAGATGAGAAGGCAG | 12 |
| CCNB1 | NM_031966 | TTCAGGTTGTTGCAGGAGACCATGTACATGACTGTCTCCATTATTGATCGGTTCATGCAGAATAATTGTGT GCCCAAGAAGATG | 13 |
| CCND1 | NM_001758 | GCATGTTCGTGGCCTCTAAGATGAAGGAGACCATCCCCCTGACGGCCGAGAAGCTGTGCATCTACACCG | 14 |
| CCNE1 | NM_001238 | AAAGAAGATGATGACCGGGTTTACCCAAACTCAACGTGCAAGCCTCGGATTATTGCACCATCCAGAGGCTC | 15 |
| CCNE2 | NM_057749 | ATGCTGTGGCTCCTTCCTAACTGGGGCTTTCTTGACATGTAGGTTGCTTGGTAATAACCTTTTTGTATATC ACAATTTGGGT | 16 |
| CD3z | NM_000734 | AGATGAAGTGGAAGGCGCTTTTCACCGCGGCCATCCTGCAGGCACAGTTGCCGATTACAGAGGCA | 17 |
| CD68 | NM_001251 | TGGTTCCCAGCCCTGTGTCCACCTCCAAGCCCAGATTCAGATTCGAGTCATGTACACAACCCAGGGTGGAGGAG | 18 |
| CD9 | NM_001769 | GGGCGTGGAACAGTTTATCTCAGACATCTGCCCCAAGAAGGACGTACTCGAAACCTTCACCGTG | 19 |
| CDH1 | NM_004360 | TGAGTGTCCCCCGGTATCTTCCCCGCCCTGCCAATCCCGATGAAATTGGAAATTTTATTGATGAAAATCTG AAAGCGGCTG | 20 |
| CEGP1 | NM_020974 | TGACAATCAGCACACCTGCATTCACCGCTCGGAAGAGGGCCTGAGCTGCATGAATAAGGATCACGGCTGTA GTCACA | 21 |
| Chk1 | NM_001274 | GATAAATTGGTACAAGGGATCAGCTTTTCCCAGCCCACATGTCCTGATCATATGCTTTTGAATAGTCAGTT ACTTGGCACCC | 22 |
| CIAP1 | NM_001166 | TGCCTGTGGTGGGAAGCTCAGTAACTGGGAACCAAAGGATGATGCTATGTCAGAACACCGGAGGCATTTTCC | 23 |
| cIAP2 | NM_001165 | GGATATTTCCGTGGCTCTTATTCAAACTCTCCATCAAATCCTGTAAACTCCAGAGCAAATCAAGATTTTTC TGCCTTGATGAGAAG | 24 |
| cMet | NM_000245 | GACATTTCCAGTCCTGCAGTCAATGCCTCTCTGCCCCACCCTTTGTTCAGTGTGGCTGGTGCCACGACAAA TGTGTGCGATCGGAG | 25 |
| Contig 27882 | AK000618 | GGCATCCTGGCCCAAAGTTTCCCAAATCCAGGCGGCTAGAGGCCCACTGCTTCCCAACTACCAGCTGAGGG GGTC | 26 |
| COX2 | NM_000963 | TCTGCAGAGTTGGAAGCACTCTATGGTGACATCGATGCTGTGGAGCTGTATCCTGCCCTTCTGGTAGAAAA GCCTCGGC | 27 |
| CTSL | NM_001912 | GGGAGGCTTATCTCACTGAGTGAGCAGAATCTGGTAGACTGCTCTGGGCCTCAAGGCAATGAAGGCTGCAATGG | 28 |
| CTSL2 | NM_001333 | TGTCTCACTGAGCGAGCAGAATCTGGTGGACTGTTCGCGTCCTCAAGGCAATCAGGGCTGCAATGGT | 29 |
| DAPK1 | NM_004938 | CGCTGACATCATGAATGTTCCTCGACCGGCTGGAGGCGAGTTTGGATATGACAAAGACACATCGTTGCTGA AAGAGA | 30 |
| DIABLO | NM_019887 | CACAATGGCGGCTCTGAAGAGTTGGCTGTCGCGCAGCGTAACTTCATTCTTCAGGTACAGACAGTGTTTGTGT | 31 |

TABLE 5B

| Gene | Accession | Seq | SEQ ID NO: |
|---|---|---|---|
| DR5 | NM_003842 | CTCTGAGACAGTGCTTCGATGACTTTGCAGACTTGGTGCCCTTTGACTCCTGGGAGCCGCTCATGAGGAAGTTGGGCCTCATGG | 32 |
| EGFR | NM_005228 | TGTCGATGGACTTCCAGAACCACCTGGGCAGCTGCCAAAAGTGTGATCCAAGCTGTCCCAAT | 33 |
| EIF4E | NM_001968 | GATCTAAGATGGCGACTGTCGAACCGGAAACCACCCCTACTCCTAATCCCCCGACTACAGAAGAGGAGAAAACGGAATCTAA | 34 |
| EMS1 | NM_005231 | GGCAGTGTCACTGAGTCCTTGAAATCCTCCCCTGCCCCGCGGGTCTCTGGATTGGGACGCACAGTGCA | 35 |
| EpCAM | NM_002354 | GGGCCCTCCAGAACAATGATGGGCTTTATGATCCTGACTGCGATGAGAGCGGGCTCTTTAAGGCCAAGCAGTGCA | 36 |
| EPHX1 | NM_000120 | ACCGTAGGCTCTGCTCTGAATGACTCTCCTGTGGGTCTGGCTGCCTATATTCTAGAGAAGTTTTCCACCTGGACCA | 37 |
| ErbB3 | NM_001982 | CGGTTATGTCATGCCAGATACACACCTCAAAGGTACTCCCTCCTCCCGGGAAGGCACCCTTTCTTCAGTGGGTCTCAGTTC | 38 |
| EstR1 | NM_000125 | CGTGGTGCCCCTCTATGACCTGCTGCTGGAGATGCTGGACGCCCACCGCCTACATGCGCCCACTAGCC | 39 |
| FBXO5 | NM_012177 | GGCTATTCCTCATTTTCTCTACAAAGTGGCCTCAGTGAACATGAAGAAGGTAGCCTCCTGGAGGAGAATTTCGGTGACAGTCTACAATCC | 40 |
| FGF18 | NM_003862 | CGGTAGTCAAGTCCGGATCAAGGGCAAGGAGACGGAATTCTACCTGTGCATGAACCGCAAAGGCAAGC | 41 |
| FGFR1 | NM_023109 | CACGGGACATTCACCACATCGACTACTATAAAAAGACAACCAACGGCCGACTGCCTGTGAAGTGGATGGCACCC | 42 |
| FHIT | NM_002012 | CCAGTGGAGCGCTTCCATGACCTGCGTCCTGATGAAGTGGCCGATTTGTTTCAGACGACCCAGAGAG | 43 |
| FRP1 | NM_003012 | TTGGTACCTGTGGGTTAGCATCAAGTTCTCCCCAGGGTAGAATTCAATCAGAGCTCCAGTTTGCATTTGGATGTG | 44 |
| G-Catenin | NM_002230 | TCAGCAGCAAGGGCATCATGGAGGAGGATGAGGCCTGCGGGCGCCAGTACACGCTCAAGAAAACCACC | 45 |
| GAPDH | NM_002046 | ATTCCACCCATGGCAAATTCCATGGCACCGTCAAGGCTGAGAACGGGAAGCTTGTCATCAATGGAAATCCCATC | 46 |
| GATA3 | NM_002051 | CAAAGGAGCTCACTGTGGTGTCTGTGTTCCAACCACTGAATCTGGACCCCATCTGTGAATAAGCCATTCTGACTC | 47 |
| GRB7 | NM_005310 | CCATCTGCATCCATCTTGTTTGGGCTCCCCACCCTTGAGAAGTGCCTCAGATAATACCCTGGTGGCC | 48 |
| GRO1 | NM_001511 | CGAAAAGATGCTGAACAGTGACAAATCCAACTGACCAGAAGGGAGGAGGAAGCTCACTGGTGGCTGTTCCTGA | 49 |
| GSTM1 | NM_000561 | AAGCTATGAGGAAAAGAAGTACACGATGGGGGACGCTCCTGATTATGACAGAAGCCAGTGGCTGAATGAAAAATTCAAGCTGGGCC | 50 |
| GUS | NM_000181 | CCCACTCAGTAGCCAAGTCACAATGTTTGGAAAACAGCCCGTTTACTTGAGCAAGACTGATACCACCTGCGTG | 51 |
| HER2 | NM_004448 | CGGTGTGAGAAGTGCAGCAAGCCCTGTGCCCGAGTGTGCTATGGTCTGGGCATGGAGCACTTGCGAGAGG | 52 |
| HIF1A | NM_001530 | TGAACATAAAGTCTGCAACATGGAAGGTATTGCACTGCACAGGCCACATTCACGTATATGATACCAACAGTAACCAACCTCA | 53 |
| HNF3A | NM_004496 | TCCAGGATGTTAGGAACTGTGAAGATGGAAGGGCATGAAACCAGCGACTGGAACAGCTACTACGCAGACACGC | 54 |
| ID1 | NM_002165 | AGAACCGCAAGGTGAGCAAGGTGGAGATTCTCCAGCACGTCATCGACTACATCAGGGACCTTCAGTTGGA | 55 |
| IGF1 | NM_000618 | TCCGGAGCTGTGATCTAAGGAGGCTGGAGATGTATTGCGCACCCCTCAAGCCTGCCAAGTCAGCTCGCTCTGTCCG | 56 |
| IGF1R | NM_000875 | GCATGGTAGCCGAAGATTTCACAGTCAAAATCGGAGATTTTGGTATGACGCGAGATATCTATGAGACAGACTATTACCGGAAA | 57 |
| IGFBP2 | NM_000597 | GTGGACAGCACCATGAACATGTTGGGCGGGGGAGGCAGTGCTGGCCGGAAGCCCCTCAAGTCGGGTATGAAGG | 58 |
| IL6 | NM_000600 | CCTGAACCTTCCAAAGATGGCTGAAAAAGATGGATGCTTCCAATCTGGATTCAATGAGGAGACTTGCCTGGT | 59 |
| IRS1 | NM_005544 | CCACAGCTCACCTTCTGTCAGGTGTCCATCCCAGCTCCAGCCAGCTCCCAGAGAGGAAGAGACTGGCACTGAGG | 60 |
| Ki-67 | NM_002417 | CGGACTTTGGGTGCGACTTGACGAGCGGTGGTTCGACAAGTGGCCTTGCGGGCCGGATCGTCCCAGTGGAAGAGTTGTAA | 61 |
| KLK10 | NM_002776 | GCCCAGAGGCTCCATCGTCCATCCTCTTCCTCCCCAGTCGGCTGAACTCTCCCCTTGTCTGCACTGTTCAAACCTCTG | 62 |

TABLE 5C

| Gene | Accession | Seq | SEQ ID NO: |
|---|---|---|---|
| KRT14 | NM_000526 | GGCCTGCTGAGATCAAAGACTACAGTCCCTACTTCAAGACCATTGAGGACCTGAGGAACAAGATTCTCACA GCCACAGTGGAC | 63 |
| KRT17 | NM_000422 | CGAGGATTGGTTCTTCAGCAAGACAGAGGAACTGAACCGCGAGGTGGCCACCAACAGTGAGCTGGTGCAGAGT | 64 |
| KRT18 | NM_000224 | AGAGATCGAGGCTCTCAAGGAGGAGCTGCTCTTCATGAAGAAGAACCACGAAGAGGAAGTAAAAGGCC | 65 |
| KRT19 | NM_002276 | TGAGCGGCAGAATCAGGAGTACCAGCGGCTCATGGACATCAAGTCGCGGCTGGAGCAGGAGATTGCCACCT ACCGCA | 66 |
| KRT5 | NM_000424 | TCAGTGGAGAAGGAGTTGGACCAGTCAACATCTCTGTTGTCACAAGCAGTGTTTCCTCTGGATATGGCA | 67 |
| KRT8 | NM_002273 | GGATGAAGCTTACATGAACAAGGTAGAGCTGGAGTCTCGCCTGGAAGGGCTGACCGACGAGATCAACTTCC TCAGGCAGCTATATG | 68 |
| LOT1 variant 1 | NM_002656 | GGAAAGACCACCTGAAAAACCACCTCCAGACCCACGACCCCAACAAAATGGCCTTTGGGTGTGAGGAGTGT GGGAAGAAGTAC | 69 |
| Maspin | NM_002639 | CAGATGGCCACTTTGAGAACATTTTAGCTGACAACAGTGTGAACGACCAGACCAAAATCCTTGTGGTTAAT GCTGCC | 70 |
| MCM2 | NM_004526 | GACTTTTGCCCGCTACCTTTCATTCCGGCGTGACAACAATGAGCTGTTGCTCTTCATACTGAAGCAGTTAGTGGC | 71 |
| MCM3 | NM_002388 | GGAGAACAATCCCCTTGAGACAGAATATGGCCTTTCTGTCTACAAGGATCACCAGACCATCACCATCCAGGAGAT | 72 |
| MCM6 | NM_005915 | TGATGGTCCTATGTGTCACATTCATCACAGGTTTCATACCAACACAGGCTTCAGCACTTCCTTTGGTGTGT TTCCTGTCCCA | 73 |
| MDM2 | NM_002392 | CTACAGGGACGCCATCGAATCCGGATCTTGATGCTGGTGTAAGTGAACATTCAGGTGATTGGTTGGAT | 74 |
| MMP9 | NM_004994 | GAGAACCAATCTCACCGACAGGCAGCTGGCAGAGGAATACCTGTACCGCTATGGTTACACTCGGGTG | 75 |
| MTA1 | NM_004689 | CCGCCCTCACCTGAAGAGAAACGCGCTCCTTGGCGGACACTGGGGGAGGAGAGGAAGAAGCGCGGCTAACT TATTCC | 76 |
| MYBL2 | NM_002466 | GCCGAGATCGCCAAGATGTTGCCAGGGAGGACAGACAATGCTGTGAAGAATCACTGGAACTCTACCATCAAAAG | 77 |
| P14ARF | S78535 | CCCTCGTGCTGATGCTACTGAGGAGCCAGCGTCTAGGGCAGCAGCCGCTTCCTAGAAGACCAGGTCATGATG | 78 |
| p27 | NM_004064 | CGGTGGACCACGAAGAGTTAACCCGGGACTTGGAGAAGCACTGCAGAGACATGGAAGAGGCGAGCC | 79 |
| P53 | NM_000546 | CTTTGAACCCTTGCTTGCAATAGGTGTGCGTCAGAAGCACCCAGGACTTCCATTTGCTTTGTCCCGGG | 80 |
| PAI1 | NM_000602 | CCGCAACGTGGTTTTCTCACCCTATGGGGTGGCCTCGGTGTTGGCCATGCTCCAGCTGACAACAGGAGGAG AAACCCAGCA | 81 |
| PDGFRb | NM_002609 | CCAGCTCTCCTTCCAGCTACAGATCAATGTCCCTGTCCGAGTGCTGGAGCTAAGTGAGAGCCACCC | 82 |
| PI3KC2A | NM_002645 | ATACCAATCACCGCACAAACCCAGGCTATTTGTTAAGTCCAGTCACAGCGCAAAGAAACATATGCGGAGAA AATGCTAGTGTG | 83 |
| PPM1D | NM_003620 | GCCATCCGCAAAGGCTTTCTCGCTTGTCACCTTGCCATGTGGAAGAAACTGGCGGAATGGCC | 84 |
| PR | NM_000926 | GCATCAGGCTGTCATTATGGTGTCCTTACCTGTGGGAGCTGTAAGGTCTTCTTTAAGAGGGCAATGGAAGG GCAGCACAACTACT | 85 |
| PRAME | NM_006115 | TCTCCATATCTGCCTTGCAGAGTCTCCTGCAGCACCTCATCGGGCTGAGCAATCTGACCCACGTGC | 86 |
| pS2 | NM_003225 | GCCCTCCCAGTGTGCAAATAAGGGCTGCTGTTTCGACGACACCGTTCGTGGGGTCCCCTGGTGCTTCTATC CTAATACCATCGACG | 87 |
| RAD51C | NM_058216 | GAACTTCTTGAGCAGGAGCATACCCAGGGCTTCATAATCACCTTCTGTTCAGCACTAGATGATATTCTTGG GGGTGGA | 88 |
| RB1 | NM_000321 | CGAAGCCCTTACAAGTTTCCTAGTTCACCCTTACGGATTCCTGGAGGGAACATCTATATTTCACCCCTGAA GAGTCC | 89 |
| RIZ1 | NM_012231 | CCAGACGAGCGATTAGAAGCGGCAGCTTGTGAGGTGAATGATTTGGGGGAAGAGGAGGAGGAGGAAGAGGAGGA | 90 |
| STK15 | NM_003600 | CATCTTCCAGGAGGACCACTCTCTGTGGCACCCTGGACTACCTGCCCCCTGAAATGATTGAAGGTCGGA | 91 |

TABLE 5C-continued

| Gene | Accession | Seq | SEQ ID NO: |
|---|---|---|---|
| STMY3 | NM_005940 | CCTGGAGGCTGCAACATACCTCAATCCTGTCCCAGGCCGGATCCTCCTGAAGCCCTTTTCGCAGCACTGCT ATCCTCCAAAGCCATTGTA | 92 |
| SURV | NM_001168 | TGTTTTGATTCCCGGGCTTACCAGGTGAGAAGTGAGGGAGGAAGAAGGCAGTGTCCCTTTTGCTAGAGCTG ACAGCTTTG | 93 |

TABLE 5D

| Gene | Accession | Seq | SEQ ID NO: |
|---|---|---|---|
| TBP | NM_003194 | GCCCGAAACGCCGAATATAATCCCAAGCGGTTTGCTGCGGTAATCATGAGGATAAGAGAGCCACG | 94 |
| TGFA | NM_003236 | GGTGTGCCACAGACCTTCCTACTTGGCCTGTAATCACCTGTGCAGCCTTTTGTGGGCCTTCAAAACTCTGT CAAGAACTCCGT | 95 |
| TIMP1 | NM_003254 | TCCCTGCGGTCCCAGATAGCCTGAATCCTGCCCGGAGTGGAACTGAAGCCTGCACAGTGTCCACCCTGTTCCCAC | 96 |
| TOP2A | NM_001067 | AATCCAAGGGGGAGAGTGATGACTTCCATATGGACTTTGACTCAGCTGTGGCTCCTCGGGCAAAATCTGTAC | 97 |
| TOP2B | NM_001068 | TGTGGACATCTTCCCCTCAGACTTCCCTACTGAGCCACCTTCTCTGCCACGAACCGGTCGGGCTAG | 98 |
| TP | NM_001953 | CTATATGCAGCCAGAGATGTGACAGCCACCGTGGACAGCCTGCCACTCATCACAGCCTCCATTCTCAGTAA GAAACTCGTGG | 99 |
| TP538P2 | NM_005426 | GGGCCAAATATTCAGAAGCTTTTATATCAGAGGACCACCATAGCGGCCATGGAGACCATCTCTGTCCCATC ATACCCATCC | 100 |
| TRAIL | NM_003810 | CTTCACAGTGCTCCTGCAGTCTCTCTGTGTGGCTGTAACTTACGTGTACTTTACCAACGAGCTGAAGCAGATG | 101 |
| TS | NM_001071 | GCCTCGGTGTGCCTTTCAACATCGCCAGCTACGCCCTGCTCACGTACATGATTGCGCACATCACG | 102 |
| upa | NM_002658 | GTGGATGTGCCCTGAAGGACAAGCCAGGCGTCTACACGAGAGTCTCACACTTCTTACCCTGGATCCGCAG | 103 |
| VDR | NM_000376 | GCCCTGGATTTCAGAAAGAGCCAAGTCTGGATCTGGGACCCTTTCCTTCCTTCCCTGGCTTGTAACT | 104 |
| VEGF | NM_003376 | CTGCTGTCTTGGGTGCATTGGAGCCTTGCCTTGCTGCTCTACCTCCACCATGCCAAGTGGTCCCAGGCTGC | 105 |
| VEGFB | NM_003377 | TGACGATGGCCTGGAGTGTGTGCCCACTGGGCAGCACCAAGTCCGGATGCAGATCCTCATGATCCGGTACC | 106 |
| WISP1 | NM_003882 | AGAGGCATCCATGAACTTCACACTTGCGGGCTGCATCAGCACACGCTCCTATCAACCCAAGTACTGTGGAGTTTG | 107 |
| XIAP | NM_001167 | GCAGTTGGAAGACACAGGAAAGTATCCCCAAATTGCAGATTTATCAACGGCTTTTATCTTGAAAATAGTGC CACGCA | 108 |
| YB-1 | NM_004559 | AGACTGTGGAGTTTGATGTTGTTGAAGGAGAAAAGGGTGCGGAGGCAGCAAATGTTACAGGTCCTGGTGGT GTTCC | 109 |
| ZNF217 | NM_006526 | ACCCAGTAGCAAGGAGAAGCCCACTCACTGCTCCGAGTGCGGCAAAGCTTTCAGAACCTACCACCAGCTG | 110 |

TABLE 6A

| Gene | Accession | Probe Name | Seq | Length | SEQ ID NO: |
|---|---|---|---|---|---|
| AIB1 | NM_006534 | S1994/AIB1.f3 | GCGGCGAGTTTCCGATTTA | 19 | 111 |
| AIB1 | NM_006534 | S1995/AIB1.r3 | TGAGTCCACCATCCAGCAAGT | 21 | 112 |
| AIB1 | NM_006534 | S5055/AIB1.p3 | ATGGCGGCGGGAGGATCAAAA | 21 | 113 |
| AKT1 | NM_005163 | S0010/AKT1.f3 | CGCTTCTATGGCGCTGAGAT | 20 | 114 |
| AKT1 | NM_005163 | S00121AKT1.r3 | TCCCGGTACACCACGTTCTT | 20 | 115 |
| AKT1 | NM_005163 | S4776/AKT1.p3 | CAGCCCTGGACTACCTGCACTCGG | 24 | 116 |
| AKT2 | NM_001626 | S0828/AKT2.f3 | TCCTGCCACCCTTCAAACC | 19 | 117 |

TABLE 6A-continued

| Gene | Accession | Probe Name | Seq | Length | SEQ ID NO: |
|---|---|---|---|---|---|
| AKT2 | NM_001626 | S0829/AKT2.r3 | GGCGGTAAATTCATCATCGAA | 21 | 118 |
| AKT2 | NM_001626 | S4727/AKT2.p3 | CAGGTCACGTCCGAGGTCGACACA | 24 | 119 |
| APC | NM_000038 | S0022/APC.f4 | GGACAGCAGGAATGTGTTTC | 20 | 120 |
| APC | NM_000038 | S0024/APC.r4 | ACCCACTCGATTTGTTTCTG | 20 | 121 |
| APC | NM_000038 | S4888/APC.p4 | CATTGGCTCCCCGTGACCTGTA | 22 | 122 |
| AREG | NM_001657 | S0025/REG.f2 | TGTGAGTGAAATGCCTTCTAGTAGTGA | 27 | 123 |
| AREG | NM_001657 | S0027/AREG.r2 | TTGTGGTTCGTTATCATACTCTTCTGA | 27 | 125 |
| AREG | NM_001657 | S4889/AREG.p2 | CCGTCCTCGGGAGCCGACTATGA | 23 | 124 |
| B-actin | NM_001101 | S0034/B-acti.f2 | CAGCAGATGTGGATCAGCAAG | 21 | 126 |
| B-actin | NM_001101 | S0036/B-acti.r2 | GCATTTGCGGTGGACGAT | 18 | 127 |
| B-actin | NM_001101 | S4730/B-acti.p2 | AGGAGTATGACGAGTCCGGCCCC | 23 | 128 |
| B-Catenin | NM_001904 | S2150/B-Cate.f3 | GGCTCTTGTGCGTACTGTCCTT | 22 | 129 |
| B-Catenin | NM_001904 | S2151/B-Cate.r3 | TCAGATGACGAAGAGCACAGATG | 23 | 130 |
| B-Catenin | NM_001904 | S5046/B-Cate.p3 | AGGCTCAGTGATGTCTTCCCTGTCACCAG | 29 | 131 |
| BAD | NM_032989 | S2011/BAD.f1 | GGGTCAGGTGCCTCGAGAT | 19 | 132 |
| BAD | NM_032989 | S2012/BAD.r1 | CTGCTCACTCGGCTCAAACTC | 21 | 133 |
| BAD | NM_032989 | S5058/BAD.p1 | TGGGCCCAGAGCATGTTCCAGATC | 24 | 134 |
| BAG1 | NM_004323 | S1386/BAG1.f2 | CGTTGTCAGCACTTGGAATACAA | 23 | 135 |
| BAG1 | NM_004323 | S1387/BAG1.r2 | GTTCAACCTCTTCCTGTGGACTGT | 24 | 135 |
| BAG1 | NM_004323 | S4731/BAG1.p2 | CCCAATTAACATGACCCGGCAACCAT | 26 | 137 |
| BBC3 | NM_014417 | S1584/BBC3.f2 | CCTGGAGGGTCCTGTACAAT | 20 | 138 |
| BBC3 | NM_014417 | S1585/BBC3.r2 | CTAATTGGGCTCCATCTCG | 19 | 139 |
| BBC3 | NM_014417 | S4890/BBC3.p2 | CATCATGGGACTCCTGCCCTTACC | 24 | 140 |
| Bcl2 | NM_000633 | S0043/Bcl2.f2 | CAGATGGACCTAGTACCCACTGAGA | 25 | 141 |
| Bcl2 | NM_000633 | S0045/Bcl2.r2 | CCTATGATTTAAGGGCATTTTTCC | 24 | 143 |
| Bcl2 | NM_000633 | S4732/Bcl2.p2 | TTCCACGCCGAAGGACAGCGAT | 22 | 142 |
| CA9 | NM_001216 | S1398/CA9.f3 | ATCCTAGCCCTGGTTTTTGG | 20 | 144 |
| CA9 | NM_001216 | S1399/CA9.r3 | CTGCCTTCTCATCTGCACAA | 20 | 145 |
| CA9 | NM_001216 | S4938/CA9.p3 | TTTGCTGTCACCAGCGTCGC | 20 | 146 |
| CCNB1 | NM_031966 | S1720/CCNB1.f2 | TTCAGGTTGTTGCAGGAGAC | 20 | 147 |
| CCNB1 | NM_031966 | S1721/CCNB1.r2 | CATCTTCTTGGGCACACAAT | 20 | 148 |
| CCNB1 | NM_031966 | S4733/CCNB1.p2 | TGTCTCCATTATTGATCGGTTCATGCA | 27 | 149 |
| CCND1 | NM_001758 | S0058/CCND1.f3 | GCATGTTCGTGGCCTCTAAGA | 21 | 150 |
| CCND1 | NM_001758 | S0060/CCND1.r3 | CGGTGTAGATGCACAGCTTCTC | 22 | 151 |
| CCND1 | NM_001758 | S4986/CCND1.p3 | AAGGAGACCATCCCCCTGACGGC | 23 | 152 |
| CCNE1 | NM_001238 | S1446/CCNE1.f1 | AAAGAAGATGATGACCGGGTTTAC | 24 | 153 |
| CCNE1 | NM_001238 | S1447/CCNE1.r1 | GAGCCTCTGGATGGTGCAAT | 20 | 154 |
| CCNE1 | NM_001238 | S4944/CCNE1.p1 | CAAACTCAACGTGCAAGCCTCGGA | 24 | 155 |

TABLE 6B

| Gene | Accession | Probe Name | Seq | Length | SEQ ID NO: |
|---|---|---|---|---|---|
| CCNE2 | NM_057749 | S1458/CCNE2.f2 | ATGCTGTGGCTCCTTCCTAACT | 22 | 156 |
| CCNE2 | NM_057749 | S1459/CCNE2.r2 | ACCCAAATTGTGATATACAAAAAGGTT | 27 | 157 |
| CCNE2 | NM_057749 | S4945/CCNE2.p2 | TACCAAGCAACCTACATGTCAAGAAAGCCC | 30 | 158 |
| CD3z | NM_000734 | S0064/CD3z.f1 | AGATGAAGTGGAAGGCGCTT | 20 | 159 |
| CD3z | NM_000734 | S0066/CD3z.r1 | TGCCTCTGTAATCGGCAACTG | 21 | 161 |
| CD3z | NM_000734 | S4988/CD3z.p1 | CACCGCGGCCATCCTGCA | 18 | 160 |
| CD68 | NM_001251 | S0067/CD68.f2 | TGGTTCCCAGCCCTGTGT | 18 | 162 |
| CD68 | NM_001251 | S0069/CD68.r2 | CTCCTCCACCCTGGGTTGT | 19 | 164 |
| CD68 | NM_001251 | S4734/CD68.p2 | CTCCAAGCCCAGATTCAGATTCGAGTCA | 28 | 163 |
| CD9 | NM_001769 | S0686/CD9.f1 | GGGCGTGGAACAGTTTATCT | 20 | 165 |
| CD9 | NM_001769 | S0687/CD9.r1 | CACGGTGAAGGTTTCGAGT | 19 | 166 |
| CD9 | NM_001769 | S4792/CD9.p1 | AGACATCTGCCCCAAGAAGGACGT | 24 | 167 |
| CDH1 | NM_004360 | S0073/CDH1.f3 | TGAGTGTCCCCCGGTATCTTC | 21 | 168 |
| CDH1 | NM_004360 | S0075/CDH1.r3 | CAGCCGCTTTCAGATTTTCAT | 21 | 169 |
| CDH1 | NM_004360 | S4990/CDH1.p3 | TGCCAATCCCGATGAAATTGGAAATTT | 27 | 170 |
| CEGP1 | NM_020974 | S1494/CEGP1.f2 | TGACAATCAGCACACCTGCAT | 21 | 171 |
| CEGP1 | NM_020974 | S1495/CEGP1.r2 | TGTGACTACAGCCGTGATCCTTA | 23 | 172 |
| CEGP1 | NM_020974 | S4735/CEGP1.p2 | CAGGCCCTCTTCCGAGCGGT | 20 | 173 |
| Chk1 | NM_001274 | S1422/Chk1.f2 | GATAAATTGGTACAAGGGATCAGCTT | 26 | 174 |
| Chk1 | NM_001274 | S1423/Chk1.r2 | GGGTGCCAAGTAACTGACTATTCA | 24 | 175 |
| Chk1 | NM_001274 | S4941/Chk1.p2 | CCACCCCACATCTCCTCATCATATGC | 26 | 176 |
| CIAP1 | NM_001166 | S0764/CIAP1/f2 | TGCCTGTGGTGGGAAGCT | 18 | 177 |
| CIAP1 | NM_001166 | S0765/CIAP1.r2 | GGAAAATGCCTCCGGTGTT | 19 | 178 |
| CIAP1 | NM_001166 | S4802/CIAP1.p2 | TGACATAGCATCATCCTTTGGTTCCCAGTT | 30 | 179 |
| cIAP2 | NM_001165 | S0076/cIAP2.f2 | GGATATTTCCGTGGCTCTTATTCA | 24 | 180 |
| cIAP2 | NM_001165 | S0078/cIAP2.r2 | CTTCTCATCAAGGCAGAAAAATCTT | 25 | 182 |
| cIAP2 | NM_001165 | S4991/cIAP2.p2 | TCTCCATCAAATCCTGTAAACTCCAGAGCA | 30 | 181 |
| cMet | NM_000245 | S0082/cMet.f2 | GACATTTCCAGTCCTGCAGTCA | 22 | 183 |
| cMet | NM_000245 | S0084/cMet.r2 | CTCCGATCGCACACATTTGT | 20 | 185 |
| cMet | NM_000245 | S4993/cMet.p2 | TGCCTCTCTGCCCCACCCTTTGT | 23 | 184 |
| Contig 27882 | AK000618 | S2633/Contig.f3 | GGCATCCTGGCCCAAAGT | 18 | 186 |
| Contig 27882 | AK000618 | S2634/Contig.r3 | GACCCCCTCAGCTGGTAGTTG | 21 | 187 |
| Contig 27882 | AK000618 | S4977/Contig.p3 | CCCAAATCCAGGCGGCTAGAGGC | 23 | 188 |
| COX2 | NM_000963 | S0088/COX2.f1 | TCTGCAGAGTTGGAAGCACTCTA | 23 | 189 |
| COX2 | NM_000963 | S0090/COX2.r1 | GCCGAGGCTTTTCTACCAGAA | 21 | 191 |
| COX2 | NM_000963 | S4995/COX2.p1 | CAGGATACAGCTCCACAGCATCGATGTC | 28 | 190 |
| CTSL | NM_001912 | S1303/CTSL.f2 | GGGAGGCTTATCTCACTGAGTGA | 23 | 192 |

TABLE 6B-continued

| Gene | Accession | Probe Name | Seq | Length | SEQ ID NO: |
|---|---|---|---|---|---|
| CTSL | NM_001912 | S1304/CTSL.r2 | CCATTGCAGCCTTCATTGC | 19 | 193 |
| CTSL | NM_001912 | S4899/CTSL.p2 | TTGAGGCCCAGAGCAGTCTACCAGATTCT | 29 | 194 |
| CTSL2 | NM_001333 | S4354/CTSL2.f1 | TGTCTCACTGAGCGAGCAGAA | 21 | 195 |
| CTSL2 | NM_001333 | S4355/CTSL2.r1 | ACCATTGCAGCCCTGATTG | 19 | 196 |
| CTSL2 | NM_001333 | S4356/CTSL2.p1 | CTTGAGGACGCGAACAGTCCACCA | 24 | 197 |

TABLE 6C

| Gene | Accession | Probe Name | Seq | Length | SEQ ID NO: |
|---|---|---|---|---|---|
| DAPK1 | NM_004938 | S1768/DAPK1.f3 | CGCTGACATCATGAATGTTCCT | 22 | 198 |
| DAPK1 | NM_004938 | S1769/DAPK1.r3 | TCTCTTTCAGCAACGATGTGTCTT | 24 | 199 |
| DAPK1 | NM_004938 | S4927/DAPK1.p3 | TCATATCCAAACTCGCCTCCAGCCG | 25 | 200 |
| DIABLO | NM_019887 | S0808/DIABLO.f1 | CACAATGGCGGCTCTGAAG | 19 | 201 |
| DIABLO | NM_019887 | S0809/DIABLO.r1 | ACACAAACACTGTCTGTACCTGAAGA | 26 | 202 |
| DIABLO | NM_019887 | S4813/DIABLO.p1 | AAGTTACGCTGCGCGACAGCCAA | 23 | 203 |
| DR5 | NM_003842 | S2551/DR5.f2 | CTCTGAGACAGTGCTTCGATGACT | 24 | 204 |
| DR5 | NM_003842 | S2552/DR5.r2 | CCATGAGGCCCAACTTCCT | 19 | 205 |
| DR5 | NM_003842 | S4979/DR5.p2 | CAGACTTGGTGCCCTTTGACTCC | 23 | 206 |
| EGFR | NM_005228 | S0103/EGFR.f2 | TGTCGATGGACTTCCAGAAC | 20 | 207 |
| EGFR | NM_005228 | S0105/EGFR.r2 | ATTGGGACAGCTTGGATCA | 19 | 209 |
| EGFR | NM_005228 | S4999/EGFR.p2 | CACCTGGGCAGCTGCCAA | 18 | 208 |
| EIF4E | NM_001968 | S0106/EIF4E.f1 | GATCTAAGATGGCGACTGTCGAA | 23 | 210 |
| EIF4E | NM_001968 | S0108/EIF4E.r1 | TTAGATTCCGTTTTCTCCTCTTCTG | 25 | 211 |
| EIF4E | NM_001968 | S5000/EIF4E.p1 | ACCACCCCTACTCCTAATCCCCCGACT | 27 | 212 |
| EMS1 | NM_005231 | S2663/EMS1.f1 | GGCAGTGTCACTGAGTCCTTGA | 22 | 213 |
| EMS1 | NM_005231 | S2664/EMS1.r1 | TGCACTGTGCGTCCCAAT | 18 | 214 |
| EMS1 | NM_005231 | S4956/EMS1.p1 | ATCCTCCCCTGCCCCGCG | 18 | 215 |
| EpCAM | NM_002354 | S1807/EpCAM.f1 | GGGCCCTCCAGAACAATGAT | 20 | 216 |
| EpCAM | NM_002354 | S1808/EpCAM.r1 | TGCACTGCTTGGCCTTAAAGA | 21 | 217 |
| EpCAM | NM_002354 | S4984/EpCAM.p1 | CCGCTCTCATCGCAGTCAGGATCAT | 25 | 218 |
| EPHX1 | NM_000120 | S1865/EPHX1.f2 | ACCGTAGGCTCTGCTCTGAA | 20 | 219 |
| EPHX1 | NM_000120 | S1866/EPHX1.r2 | TGGTCCAGGTGGAAAACTTC | 20 | 220 |
| EPHX1 | NM_000120 | S4754/EPHX1.p2 | AGGCAGCCAGACCCACAGGA | 20 | 221 |
| ErbB3 | NM_001982 | S0112/ErbB3.f1 | CGGTTATGTCATGCCAGATACAC | 23 | 222 |
| ErbB3 | NM_001982 | S0114/ErbB3.r1 | GAACTGAGACCCACTGAAGAAAGG | 24 | 224 |
| ErbB3 | NM_001982 | S5002/ErbB3.p1 | CCTCAAAGGTACTCCCTCCTCCCGG | 25 | 223 |
| EstR1 | NM_000125 | S0115/EstR1.f1 | CGTGGTGCCCCTCTATGAC | 19 | 225 |

TABLE 6C-continued

| Gene | Accession | Probe Name | Seq | Length | SEQ ID NO: |
|---|---|---|---|---|---|
| EstR1 | NM_000125 | S0117/EstR1.r1 | GGCTAGTGGGCGCATGTAG | 19 | 227 |
| EstR1 | NM_000125 | S4737/EstR1.p1 | CTGGAGATGCTGGACGCCC | 19 | 226 |
| FBXO5 | NM_012177 | S2017/FBXO5.r1 | GGATTGTAGACTGTCACCGAAATTC | 25 | 228 |
| FBXO5 | NM_012177 | S2018/FBXO5.f1 | GGCTATTCCTCATTTTCTCTACAAAGTG | 28 | 229 |
| FBXO5 | NM_012177 | S5061/FBXO5.p1 | CCTCCAGGAGGCTACCTTCTTCATGTTCAC | 30 | 230 |
| FGF18 | NM_003862 | S1665/FGF18.f2 | CGGTAGTCAAGTCCGGATCAA | 21 | 231 |
| FGF18 | NM_003862 | S1666/FGF18.r2 | GCTTGCCTTTGCGGTTCA | 18 | 232 |
| FGF18 | NM_003862 | S4914/FGF18.p2 | CAAGGAGACGGAATTCTACCTGTGC | 25 | 233 |
| FGFR1 | NM_023109 | S0818/FGFR1.f3 | CACGGGACATTCACCACATC | 20 | 234 |
| FGFR1 | NM_023109 | S0819/FGFR1.r3 | GGGTGCCATCCACTTCACA | 19 | 235 |
| FGFR1 | NM_023109 | S4816/FGFR1.p3 | ATAAAAAGACAACCAACGGCCGACTGC | 27 | 236 |
| FHIT | NM_002012 | S2443/FHIT.f1 | CCAGTGGAGCGCTTCCAT | 18 | 237 |
| FHIT | NM_002012 | S2444/FHIT.r1 | CTCTCTGGGTCGTCTGAAACAA | 22 | 238 |
| FHIT | NM_002012 | S2445/FHIT.p1 | TCGGCCACTTCATCAGGACGCAG | 23 | 239 |
| FHIT | NM_002012 | S4921/FHIT.p1 | TCGGCCACTTCATCAGGACGCAG | 23 | 239 |
| FRP1 | NM_003012 | S1804/FRP1.f3 | TTGGTACCTGTGGGTTAGCA | 20 | 240 |
| FRP1 | NM_003012 | S1805/FRP1.r3 | CACATCCAAATGCAAACTGG | 20 | 241 |

TABLE 6D

| Gene | Accession | Probe Name | Seq | Length | SEQ ID NO: |
|---|---|---|---|---|---|
| FRP1 | NM_003012 | S4983/FRP1.p3 | TCCCCAGGGTAGAATTCAATCAGAGC | 26 | 242 |
| G-Catenin | NM_002230 | S2153/G-Cate.f1 | TCAGCAGCAAGGGCATCAT | 19 | 243 |
| G-Catenin | NM_002230 | S2154/G-Cate.r1 | GGTGGTTTTCTTGAGCGTGTACT | 23 | 244 |
| G-Catenin | NM_002230 | S5044/G-Cate.p1 | CGCCCGCAGGCCTCATCCT | 19 | 245 |
| GAPDH | NM_002046 | S0374/GAPDH.f1 | ATTCCACCCATGGCAAATTC | 20 | 246 |
| GAPDH | NM_002046 | S0375/GAPDH.r1 | GATGGGATTTCCATTGATGACA | 22 | 247 |
| GAPDH | NM_002046 | S4738/GAPDH.p1 | CCGTTCTCAGCCTTGACGGTGC | 22 | 248 |
| GATA3 | NM_002051 | S0127/GATA3.f3 | CAAAGGAGCTCACTGTGGTGTCT | 23 | 249 |
| GATA3 | NM_002051 | S0129/GATA3.r3 | GAGTCAGAATGGCTTATTCACAGATG | 26 | 251 |
| GATA3 | NM_002051 | S5005/GATA3.p3 | TGTTCCAACCACTGAATCTGGACC | 24 | 250 |
| GRB7 | NM_005310 | S0130/GRB7.f2 | CCATCTGCATCCATCTTGTT | 20 | 252 |
| GRB7 | NM_005310 | S0132/GRB7.r2 | GGCCACCAGGGTATTATCTG | 20 | 254 |
| GRB7 | NM_005310 | S4726/GRB7.p2 | CTCCCCACCCTTGAGAAGTGCCT | 23 | 253 |
| GRO1 | NM_001511 | S0133/GRO1.f2 | CGAAAAGATGCTGAACAGTGACA | 23 | 255 |
| GRO1 | NM_001511 | S0135/GRO1.r2 | TCAGGAACAGCCACCAGTGA | 20 | 256 |
| GRO1 | NM_001511 | S5006/GRO1.p2 | CTTCCTCCTCCCTTCTGGTCAGTTGGAT | 28 | 257 |
| GSTM1 | NM_000561 | S2026/GSTM1.r1 | GGCCCAGCTTGAATTTTTCA | 20 | 258 |

TABLE 6D-continued

| Gene | Accession | Probe Name | Seq | Length | SEQ ID NO: |
|---|---|---|---|---|---|
| GSTM1 | NM_000561 | S2027/GSTM1.f1 | AAGCTATGAGGAAAAGAAGTACACGAT | 27 | 259 |
| GSTM1 | NM_000561 | S4739/GSTM1.p1 | TCAGCCACTGGCTTCTGTCATAATCAGGAG | 30 | 260 |
| GUS | NM_000181 | S0139/GUS.f1 | CCCACTCAGTAGCCAAGTCA | 20 | 261 |
| GUS | NM_000181 | S0141/GUS.r1 | CACGCAGGTGGTATCAGTCT | 20 | 263 |
| GUS | NM_000181 | S4740/GUS.p1 | TCAAGTAAACGGGCTGTTTTCCAAACA | 27 | 262 |
| HER2 | NM_004448 | S0142/HER2.f3 | CGGTGTGAGAAGTGCAGCAA | 20 | 264 |
| HER2 | NM_004448 | S0144/HER2.r3 | CCTCTCGCAAGTGCTCCAT | 19 | 266 |
| HER2 | NM_004448 | S4729/HER2.p3 | CCAGACCATAGCACACTCGGGCAC | 24 | 265 |
| HIF1A | NM_001530 | S1207/HIF1A.f3 | TGAACATAAAGTCTGCAACATGGA | 24 | 267 |
| HIF1A | NM_001530 | S1208/HIF1A.r3 | TGAGGTTGGTTACTGTTGGTATCATATA | 28 | 268 |
| HIF1A | NM_001530 | S4753/HIF1A.p3 | TTGCACTGCACAGGCCACATTCAC | 24 | 269 |
| HNF3A | NM_004496 | S0148/HNF3A.f1 | TCCAGGATGTTAGGAACTGTGAAG | 24 | 270 |
| HNF3A | NM_004496 | S0150/HNF3A.r1 | GCGTGTCTGCGTAGTAGCTGTT | 22 | 271 |
| HNF3A | NM_004496 | S5008/HNF3A.p1 | AGTCGCTGGTTTCATGCCCTTCCA | 24 | 272 |
| ID1 | NM_002165 | S0820/ID1.f1 | AGAACCGCAAGGTGAGCAA | 19 | 273 |
| ID1 | NM_002165 | S0821/ID1.r1 | TCCAACTGAAGGTCCCTGATG | 21 | 274 |
| ID1 | NM_002165 | S4832/ID1.p1 | TGGAGATTCTCCAGCACGTCATCGAC | 26 | 275 |
| IGF1 | NM_000618 | S0154/IGF1.f2 | TCCGGAGCTGTGATCTAAGGA | 21 | 276 |
| IGF1 | NM_000618 | S0156/IGF1.r2 | CGGACAGAGCGAGCTGACTT | 20 | 278 |
| IGF1 | NM_000618 | S5010/IGF1.p2 | TGTATTGCGCACCCCTCAAGCCTG | 24 | 277 |
| IGF1R | NM_000875 | S1249/IGF1R.f3 | GCATGGTAGCCGAAGATTTCA | 21 | 279 |
| IGF1R | NM_000875 | S1250/IGF1R.r3 | TTTCCGGTAATAGTCTGTCTCATAGATATC | 30 | 280 |
| IGF1R | NM_000875 | S4895/IGF1R.p3 | CGCGTCATACCAAAATCTCCGATTTTGA | 28 | 281 |
| IGFBP2 | NM_000597 | S1128/IGFBP2.f1 | GTGGACAGCACCATGAACA | 19 | 282 |
| IGFBP2 | NM_000597 | S1129/IGFBP2.r1 | CCTTCATACCCGACTTGAGG | 20 | 283 |
| IGFBP2 | NM_000597 | S4837/IGFBP2.p1 | CTTCCGGCCAGCACTGCCTC | 20 | 284 |
| IL6 | NM_000600 | S0760/IL6.f3 | CCTGAACCTTCCAAAGATGG | 20 | 285 |

TABLE 6E

| Gene | Accession | Probe Name | Seq | Length | SEQ ID NO: |
|---|---|---|---|---|---|
| IL6 | NM_000600 | S0761/IL6.r3 | ACCAGGCAAGTCTCCTCATT | 20 | 286 |
| IL6 | NM_000600 | S4800/IL6.p3 | CCAGATTGGAAGCATCCATCTTTTTCA | 27 | 287 |
| IRS1 | NM_005544 | S1943/IRS1.f3 | CCACAGCTCACCTTCTGTCA | 20 | 288 |
| IRS1 | NM_005544 | S1944/IRS1.r3 | CCTCAGTGCCAGTCTCTTCC | 20 | 289 |
| IRS1 | NM_005544 | S5050/IRS1.p3 | TCCATCCCAGCTCCAGCCAG | 20 | 290 |
| Ki-67 | NM_002417 | S0436/Ki-67.f2 | CGGACTTTGGGTGCGACTT | 19 | 292 |

TABLE 6E-continued

| Gene | Accession | Probe Name | Seq | Length | SEQ ID NO: |
|---|---|---|---|---|---|
| Ki-67 | NM_002417 | S0437/Ki-67.r2 | TTACAACTCTTCCACTGGGACGAT | 24 | 293 |
| Ki-67 | NM_002417 | S4741/Ki-67.p2 | CCACTTGTCGAACCACCGCTCGT | 23 | 291 |
| KLK10 | NM_002776 | S2624/KLK10.f3 | GCCCAGAGGCTCCATCGT | 18 | 294 |
| KLK10 | NM_002776 | S2625/KLK10.r3 | CAGAGGTTTGAACAGTGCAGACA | 23 | 295 |
| KLK10 | NM_002776 | S4978/KLK10.p3 | CCTCTTCCTCCCCAGTCGGCTGA | 23 | 296 |
| KRT14 | NM_000526 | S1853/KRT14.f1 | GGCCTGCTGAGATCAAAGAC | 20 | 297 |
| KRT14 | NM_000526 | S1854/KRT14.r1 | GTCCACTGTGGCTGTGAGAA | 20 | 298 |
| KRT14 | NM_000526 | S5037/KRT14.p1 | TGTTCCTCAGGTCCTCAATGGTCTTG | 26 | 299 |
| KRT17 | NM_000422 | S0172/KRT17.f2 | CGAGGATTGGTTCTTCAGCAA | 21 | 300 |
| KRT17 | NM_000422 | S0174/KRT17.r2 | ACTCTGCACCAGCTCACTGTTG | 22 | 301 |
| KRT17 | NM_000422 | S5013/KRT17.p2 | CACCTCGCGGTTCAGTTCCTCTGT | 24 | 302 |
| KRT18 | NM_000224 | S1710/KRT18.f2 | AGAGATCGAGGCTCTCAAGG | 20 | 303 |
| KRT18 | NM_000224 | S1711/KRT18.r2 | GGCCTTTTACTTCCTCTTCG | 20 | 304 |
| KRT18 | NM_000224 | S4762/KRT18.p2 | TGGTTCTTCTTCATGAAGAGCAGCTCC | 27 | 305 |
| KRT19 | NM_002276 | S1515/KRT19.f3 | TGAGCGGCAGAATCAGGAGTA | 21 | 306 |
| KRT19 | NM_002276 | S1516/KRT19.r3 | TGCGGTAGGTGGCAATCTC | 19 | 307 |
| KRT19 | NM_002276 | S4866/KRT19.p3 | CTCATGGACATCAAGTCGCGGCTG | 24 | 308 |
| KRT5 | NM_000424 | S0175/KRT5.f3 | TCAGTGGAGAAGGAGTTGGA | 20 | 309 |
| KRT5 | NM_000424 | S0177/KRT5.r3 | TGCCATATCCAGAGGAAACA | 20 | 311 |
| KRT5 | NM_000424 | S5015/KRT5.p3 | CCAGTCAACATCTCTGTTGTCACAAGCA | 28 | 310 |
| KRT8 | NM_002273 | S2588/KRT8.f3 | GGATGAAGCTTACATGAACAAGGTAGA | 27 | 312 |
| KRT8 | NM_002273 | S2589/KRT8.r3 | CATATAGCTGCCTGAGGAAGTTGAT | 25 | 313 |
| KRT8 | NM_002273 | S4952/KRT8.p3 | CGTCGGTCAGCCCTTCCAGGC | 21 | 314 |
| LOT1 variant 1 | NM_002656 | S0692/LOT1 v.f2 | GGAAAGACCACCTGAAAAACCA | 22 | 315 |
| LOT1 variant 1 | NM_002656 | S0693/LOT1 v.r2 | GTACTTCTTCCCACACTCCTCACA | 24 | 316 |
| LOT1 variant 1 | NM_002656 | S4793/LOT1 v.p2 | ACCCACGACCCCAACAAAATGGC | 23 | 317 |
| Maspin | NM_002639 | S0836/Maspin.f2 | CAGATGGCCACTTTGAGAACATT | 23 | 318 |
| Maspin | NM_002639 | S0837/Maspin.r2 | GGCAGCATTAACCACAAGGATT | 22 | 319 |
| Maspin | NM_002639 | S4835/Maspin.p2 | AGCTGACAACAGTGTGAACGACCAGACC | 28 | 320 |
| MCM2 | NM_004526 | S1602/MCM2.f2 | GACTTTTGCCCGCTACCTTTC | 21 | 321 |
| MCM2 | NM_004526 | S1603/MCM2.r2 | GCCACTAACTGCTTCAGTATGAAGAG | 26 | 322 |
| MCM2 | NM_004526 | S4900/MCM2.p2 | ACAGCTCATTGTTGTCACGCCGGA | 24 | 323 |
| MCM3 | NM_002388 | S1524/MCM3.f3 | GGAGAACAATCCCCTTGAGA | 20 | 324 |
| MCM3 | NM_002388 | S1525/MCM3.r3 | ATCTCCTGGATGGTGATGGT | 20 | 325 |
| MCM3 | NM_002388 | S4870/MCM3.p3 | TGGCCTTTCTGTCTACAAGGATCACCA | 27 | 326 |

TABLE 6E-continued

| Gene | Accession | Probe Name | Seq | Length | SEQ ID NO: |
|---|---|---|---|---|---|
| MCM6 | NM_005915 | S1704/MCM6.f3 | TGATGGTCCTATGTGTCACATTCA | 24 | 327 |
| MCM6 | NM_005915 | S1705/MCM6.r3 | TGGGACAGGAAACACACCAA | 20 | 328 |

TABLE 6F

| Gene | Accession | Probe Name | Seq | Length | SEQ ID NO: |
|---|---|---|---|---|---|
| MCM6 | NM_005915 | S4919/MCM6.p3 | CAGGTTTCATACCAACACAGGCTTCAGCAC | 30 | 329 |
| MDM2 | NM_002392 | S0830/MDM2.f1 | CTACAGGGACGCCATCGAA | 19 | 330 |
| MDM2 | NM_002392 | S0831/MDM2.r1 | ATCCAACCAATCACCTGAATGTT | 23 | 331 |
| MDM2 | NM_002392 | S4834/MDM2.p1 | CTTACACCAGCATCAAGATCCGG | 23 | 332 |
| MMP9 | NM_004994 | S0656/MMP9.f1 | GAGAACCAATCTCACCGACA | 20 | 333 |
| MMP9 | NM_004994 | S0657/MMP9.r1 | CACCCGAGTGTAACCATAGC | 20 | 334 |
| MMP9 | NM_004994 | S4760/MMP9.p1 | ACAGGTATTCCTCTGCCAGCTGCC | 24 | 335 |
| MTA1 | NM_004689 | S2369/MTA1.f1 | CCGCCCTCACCTGAAGAGA | 19 | 336 |
| MTA1 | NM_004689 | S2370/MTA1.r1 | GGAATAAGTTAGCCGCGCTTCT | 22 | 337 |
| MTA1 | NM_004689 | S4855/MTA1.p1 | CCCAGTGTCCGCCAAGGAGCG | 21 | 338 |
| MYBL2 | NM_002466 | S3270/MYBL2.f1 | GCCGAGATCGCCAAGATG | 18 | 339 |
| MYBL2 | NM_002466 | S3271/MYBL2.r1 | CTTTTGATGGTAGAGTTCCAGTGATTC | 27 | 340 |
| MYBL2 | NM_002466 | S4742/MYBL2.p1 | CAGCATTGTCTGTCCTCCCTGGCA | 24 | 341 |
| P14ARF | S78535 | S2842/P14ARF.f1 | CCCTCGTGCTGATGCTACT | 19 | 342 |
| P14ARF | S78535 | S2843/P14ARF.r1 | CATCATGACCTGGTCTTCTAGG | 22 | 343 |
| P14ARF | S78535 | S4971/P14ARF.p1 | CTGCCCTAGACGCTGGCTCCTC | 22 | 344 |
| p27 | NM_004064 | S0205/p27.f3 | CGGTGGACCACGAAGAGTTAA | 21 | 345 |
| p27 | NM_004064 | S0207/p27.r3 | GGCTCGCCTCTTCCATGTC | 19 | 347 |
| p27 | NM_004064 | S4750/p27.p3 | CCGGGACTTGGAGAAGCACTGCA | 23 | 346 |
| P53 | NM_000546 | S0208/P53.f2 | CTTTGAACCCTTGCTTGCAA | 20 | 348 |
| P53 | NM_000546 | S0210/P53/r2 | CCCGGGACAAAGCAAATG | 18 | 350 |
| P53 | NM_000546 | S5065/P53.p2 | AAGTCCTGGGTGCTTCTGACGCACA | 25 | 349 |
| PAI1 | NM_000602 | S0211/PAI1.f3 | CCGCAACGTGGTTTTCTCA | 19 | 351 |
| PAI1 | NM_000602 | S0213/PAI1.r3 | TGCTGGGTTTCTCCTCCTGTT | 21 | 353 |
| PAI1 | NM_000602 | S5066/PAI1.p3 | CTCGGTGTTGGCCATGCTCCAG | 22 | 352 |
| PDGFRb | NM_002609 | S1346/PDGFRb.f3 | CCAGCTCTCCTTCCAGCTAC | 20 | 354 |
| PDGFRb | NM_002609 | S1347/PDGFRb.r3 | GGGTGGCTCTCACTTAGCTC | 20 | 355 |
| PDGFRb | NM_002609 | S4931/PDGFRb.p3 | ATCAATGTCCCTGTCCGAGTGCTG | 24 | 356 |
| PI3KC2A | NM_002645 | S2020/PI3KC2.r1 | CACACTAGCATTTTCTCCGCATA | 23 | 357 |
| PI3KC2A | NM_002645 | S2021/PI3KC2.f1 | ATACCAATCACCGCACAAACC | 21 | 358 |
| PI3KC2A | NM_002645 | S5062/PI3KC2.p1 | TGCGCTGTGACTGGACTTAACAAATAGCCT | 30 | 359 |
| PPM1D | NM_003620 | S3159/PPM1D.f1 | GCCATCCGCAAAGGCTTT | 18 | 360 |

TABLE 6F-continued

| Gene | Accession | Probe Name | Seq | Length | SEQ ID NO: |
|---|---|---|---|---|---|
| PPM1D | NM_003620 | S3160/PPM1D.r1 | GGCCATTCCGCCAGTTTC | 18 | 361 |
| PPM1D | NM_003620 | S4856/PPM1D.p1 | TCGCTTGTCACCTTGCCATGTGG | 23 | 362 |
| PR | NM_000926 | S1336/PR.f6 | GCATCAGGCTGTCATTATGG | 20 | 363 |
| PR | NM_000926 | S1337/PR.r6 | AGTAGTTGTGCTGCCCTTCC | 20 | 364 |
| PR | NM_000926 | S4743/PR.p6 | TGTCCTTACCTGTGGGAGCTGTAAGGTC | 28 | 365 |
| PRAME | NM_006115 | S1985/PRAME.f3 | TCTCCATATCTGCCTTGCAGAGT | 23 | 366 |
| PRAME | NM_006115 | S1986/PRAME.r3 | GCACGTGGGTCAGATTGCT | 19 | 367 |
| PRAME | NM_006115 | S4756/PRAME.p3 | TCCTGCAGCACCTCATCGGGCT | 22 | 368 |
| pS2 | NM_003225 | S0241/pS2.f2 | GCCCTCCCAGTGTGCAAAT | 19 | 369 |
| pS2 | NM_003225 | S0243/pS2.r2 | CGTCGATGGTATTAGGATAGAAGCA | 25 | 371 |
| pS2 | NM_003225 | S5026/pS2.p2 | TGCTGTTTCGACGACACCGTTCG | 23 | 370 |
| RAD51C | NM_058216 | S2606/RAD51C.f3 | GAACTTCTTGAGCAGGAGCATACC | 24 | 372 |

TABLE 6G

| Gene | Accession | Probe Name | Seq | Length | SEQ ID NO: |
|---|---|---|---|---|---|
| RAD51C | NM_058216 | S2607/RAD51C.r3 | TCCACCCCCAAGAATATCATCTAGT | 25 | 373 |
| RAD51C | NM_058216 | S4764/RAD51C.p3 | AGGGCTTCATAATCACCTTCTGTTC | 25 | 374 |
| RB1 | NM_000321 | S2700/RB1.f1 | CGAAGCCCTTACAAGTTTCC | 20 | 375 |
| RB1 | NM_000321 | S2701/RB1.r1 | GGACTCTTCAGGGGTGAAAT | 20 | 376 |
| RB1 | NM_000321 | S4765/RB1.p1 | CCCTTACGGATTCCTGGAGGGAAC | 24 | 377 |
| RIZ1 | NM_012231 | S1320/RIZ1.f2 | CCAGACGAGCGATTAGAAGC | 20 | 378 |
| RIZ1 | NM_012231 | S1321/RIZ1.r2 | TCCTCCTCTTCCTCCTCCTC | 20 | 379 |
| RIZ1 | NM_012231 | S4761/RIZ1.p2 | TGTGAGGTGAATGATTTGGGGGA | 23 | 380 |
| STK15 | NM_003600 | S0794/STK15.f2 | CATCTTCCAGGAGGACCACT | 20 | 381 |
| STK15 | NM_003600 | S0795/STK15.r2 | TCCGACCTTCAATCATTTCA | 20 | 382 |
| STK15 | NM_003600 | S4745/STK15.p2 | CTCTGTGGCACCCTGGACTACCTG | 24 | 383 |
| STMY3 | NM_005940 | S2067/STMY3.f3 | CCTGGAGGCTGCAACATACC | 20 | 384 |
| STMY3 | NM_005940 | S2068/STMY3.r3 | TACAATGGCTTTGGAGGATAGCA | 23 | 385 |
| STMY3 | NM_005940 | S4746/STMY3.p3 | ATCCTCCTGAAGCCCTTTTCGCAGC | 25 | 386 |
| SURV | NM_001168 | S0259/SURV.f2 | TGTTTTGATTCCCGGGCTTA | 20 | 387 |
| SURV | NM_001168 | S0261/SURV.r2 | CAAAGCTGTCAGCTCTAGCAAAAG | 24 | 389 |
| SURV | NM_001168 | S4747/SURV.p2 | TGCCTTCTTCCTCCCTCACTTCTCACCT | 28 | 388 |
| TBP | NM_003194 | S0262/TBP.f1 | GCCCGAAACGCCGAATATA | 19 | 390 |
| TBP | NM_003194 | S0264/TBP.r1 | CGTGGCTCTCTTATCCTCATGAT | 23 | 392 |
| TBP | NM_003194 | S4751/TBP.p1 | TACCGCAGCAAACCGCTTGGG | 21 | 391 |
| TGFA | NM_003236 | S0489/TGFA.f2 | GGTGTGCCACAGACCTTCCT | 20 | 393 |

TABLE 6G-continued

| Gene | Accession | Probe Name | Seq | Length | SEQ ID NO: |
|---|---|---|---|---|---|
| TGFA | NM_003236 | S0490/TGFA.r2 | ACGGAGTTCTTGACAGAGTTTTGA | 24 | 394 |
| TGFA | NM_003236 | S4768/TGFA.p2 | TTGGCCTGTAATCACCTGTGCAGCCTT | 27 | 395 |
| TIMP1 | NM_003254 | S1695/TIMP1.f3 | TCCCTGCGGTCCCAGATAG | 19 | 396 |
| TIMP1 | NM_003254 | S1696/TIMP1.r3 | GTGGGAACAGGGTGGACACT | 20 | 397 |
| TIMPI | NM_003254 | S4918/TIMP1.p3 | ATCCTGCCCGGAGTGGAACTGAAGC | 25 | 398 |
| TOP2A | NM_001067 | S0271/TOP2A.f4 | AATCCAAGGGGGAGAGTGAT | 20 | 399 |
| TOP2A | NM_001067 | S0273/TOP2A.r4 | GTACAGATTTTGCCCGAGGA | 20 | 401 |
| TOP2A | NM_001067 | S4777/TOP2A.p4 | CATATGGACTTTGACTCAGCTGTGGC | 26 | 400 |
| TOP2B | NM_001068 | S0274/TOP2B.f2 | TGTGGACATCTTCCCCTCAGA | 21 | 402 |
| TOP2B | NM_001068 | S0276/TOP2B.r2 | CTAGCCCGACCGGTTCGT | 18 | 404 |
| TOP2B | NM_001068 | S4778/TOP2B.p2 | TTCCCTACTGAGCCACCTTCTCTG | 24 | 403 |
| TP | NM_001953 | S0277/TP.f3 | CTATATGCAGCCAGAGATGTGACA | 24 | 405 |
| TP | NM_001953 | S0279/TP.r3 | CCACGAGTTTCTTACTGAGAATGG | 24 | 407 |
| TP | NM_001953 | S4779/TP.p3 | ACAGCCTGCCACTCATCACAGCC | 23 | 406 |
| TP53BP2 | NM_005426 | S1931/TP53BP.f2 | GGGCCAAATATTCAGAAGC | 19 | 408 |
| TP53BP2 | NM_005426 | S1932/TP53BP.r2 | GGATGGGTATGATGGGACAG | 20 | 409 |
| TP53BP2 | NM_005426 | S5049/TP53BP.p2 | CCACCATAGCGGCCATGGAG | 20 | 410 |
| TRAIL | NM_003810 | S2539/TRAIL.f1 | CTTCACAGTGCTCCTGCAGTCT | 22 | 411 |
| TRAIL | NM_003810 | S2540/TRAIL.r1 | CATCTGCTTCAGCTCGTTGGT | 21 | 412 |
| TRAIL | NM_003810 | S4980/TRAIL.p1 | AAGTACACGTAAGTTACAGCCACACA | 26 | 413 |
| TS | NM_001071 | S0280/TS.f1 | GCCTCGGTGTGCCTTTCA | 18 | 414 |
| TS | NM_001071 | S0282/TS.r1 | CGTGATGTGCGCAATCATG | 19 | 416 |
| TS | NM_001071 | S4780/TS.p1 | CATCGCCAGCTACGCCCTGCTC | 22 | 415 |
| upa | NM_002658 | S0283/upa.f3 | GTGGATGTGCCCTGAAGGA | 19 | 417 |

TABLE 6H

| Gene | Accession | Probe Name | Seq | Length | SEQ ID NO: |
|---|---|---|---|---|---|
| upa | NM_002658 | S0285/upa.r3 | CTGCGGATCCAGGGTAAGAA | 20 | 418 |
| upa | NM_002658 | S4769/upa.p3 | AAGCCAGGCGTCTACACGAGAGTCTCAC | 28 | 419 |
| VDR | NM_000376 | S2745/VDR.f2 | GCCCTGGATTTCAGAAAGAG | 20 | 420 |
| VDR | NM_000376 | S2746/VDR.r2 | AGTTACAAGCCAGGGAAGGA | 20 | 421 |
| VDR | NM_000376 | S4962/VDR.p2 | CAAGTCTGGATCTGGGACCCTTTCC | 25 | 422 |
| VEGF | NM_003376 | S0286/VEGF.f1 | CTGCTGTCTTGGGTGCATTG | 20 | 423 |
| VEGF | NM_003376 | S0288/VEGF.r1 | GCAGCCTGGGACCACTTG | 18 | 424 |
| VEGF | NM_003376 | S4782/VEGF.p1 | TTGCCTTGCTGCTCTACCTCCACCA | 25 | 425 |
| VEGFB | NM_003377 | S2724/VEGFB.f1 | TGACGATGGCCTGGAGTGT | 19 | 426 |
| VEGFB | NM_003377 | S2725/VEGFB.r1 | GGTACCGGATCATGAGGATCTG | 22 | 427 |

TABLE 6H-continued

| Gene | Accession | Probe Name | Seq | Length | SEQ ID NO: |
|---|---|---|---|---|---|
| VEGFB | NM_003377 | S4960/VEGFB.p1 | CTGGGCAGCACCAAGTCCGGA | 21 | 428 |
| WISP1 | NM_003882 | S1671/WISP1.f1 | AGAGGCATCCATGAACTTCACA | 22 | 429 |
| WISP1 | NM_003882 | S1672/WISP1.r1 | CAAACTCCACAGTACTTGGGTTGA | 24 | 430 |
| WISP1 | NM_003882 | S4915/WISP1.p1 | CGGGCTGCATCAGCACACGC | 20 | 431 |
| XIAP | NM_001167 | S0289/XIAP.f1 | GCAGTTGGAAGACACAGGAAAGT | 23 | 432 |
| XIAP | NM_001167 | S0291/XIAP.r1 | TGCGTGGCACTATTTTCAAGA | 21 | 434 |
| XIAP | NM_001167 | S4752/XIAP.p1 | TCCCCAAATTGCAGATTTATCAACGGC | 27 | 433 |
| YB-1 | NM_004559 | S1194/YB-1.f2 | AGACTGTGGAGTTTGATGTTGTTGA | 25 | 435 |
| YB-1 | NM_004559 | S1195/YB-1.r2 | GGAACACCACCAGGACCTGTAA | 22 | 436 |
| YB-1 | NM_004559 | S4843/YB-1.p2 | TTGCTGCCTCCGCACCCTTTTCT | 23 | 437 |
| ZNF217 | NM_006526 | S2739/ZNF217.f3 | ACCCAGTAGCAAGGAGAAGC | 20 | 438 |
| ZNF217 | NM_006526 | S2740/ZNF217.r3 | CAGCTGGTGGTAGGTTCTGA | 20 | 439 |
| ZNF217 | NM_006526 | S4961/ZNF217.p3 | CACTCACTGCTCCGAGTGCGG | 21 | 440 |

What is claimed is:

1. A method of predicting the likelihood of long-term survival of a breast cancer patient without the recurrence of breast cancer, comprising:

quantitatively determining a level of an RNA transcript of CD68 in a breast cancer tissue sample obtained from said patient using a primer comprising the nucleotide sequence of SEQ ID NO:162, normalizing said level against the expression level of a reference set of RNA transcripts to obtain a normalized CD68 expression level;

comparing the normalized CD68 expression level to a normalized CD68 expression level in reference breast tumor samples; and predicting a likelihood of long-term survival without recurrence of breast cancer of the patient, wherein increased normalized CD68 expression level indicates a decreased likelihood of long-term survival without breast cancer recurrence.

2. The method of claim 1 wherein the breast cancer is invasive breast carcinoma.

3. The method of claim 1 wherein said RNA is isolated from core biopsy tissue or fine needle aspirate cells.

4. A method of predicting the likelihood of long-term survival of a patient diagnosed with estrogen receptor (ER)-positive breast cancer, without the recurrence of breast cancer, comprising the steps of:

(1) quantitatively determining the level of an RNA transcript of CD68 in a breast cancer tissue sample obtained from said patient using a primer comprising the nucleotide sequence of SEQ ID NO:162, (2) normalizing the level of the RNA transcript of CD68 against a reference set of RNA transcripts to obtain a normalized CD68 expression level;

(3) comparing the normalized CD68 expression level to a normalized CD68 expression level in reference breast tumor samples;

(4) subjecting the normalized CD68 expression level obtained in step (2) to statistical analysis; and (5) determining whether the patient has an increased or decreased likelihood of said long-term survival without recurrence of breast cancer, wherein increased normalized CD68 expression level is indicative of a reduced likelihood of long-term survival without recurrence of breast cancer.

5. The method of claim 4, wherein said sample is a tissue sample from fine needle, core, or other types of biopsy.

6. The method of claim 4, wherein the level of the RNA transcript of CD68 is determined by quantitative reverse transcription polymerase chain reaction (qRT-PCR).

7. The method of claim 4, further comprising the step of preparing a report indicating that the patient has an increased or decreased likelihood of long-term survival without breast cancer recurrence.

8. The method of claim 1, wherein the level of the RNA transcript of CD68 is determined by quantitative reverse transcription polymerase chain reaction (qRT-PCR).

9. The method of claim 1, further comprising the step of preparing a report indicating that the patient has an increased or decreased likelihood of long-term survival without breast cancer recurrence.

10. A method of predicting the likelihood of long-term survival of a breast cancer patient without the recurrence of breast cancer, comprising:

isolating RNA from a tissue sample obtained from a breast tumor of the patient;

reverse transcribing an RNA transcript of CD68 to produce a cDNA of CD68 using a primer comprising the nucleotide sequence of SEQ ID NO:162;

amplifying the cDNA of CD68;

producing an amplicon of the RNA transcript of CD68;

qauntitatively assaying a level of the amplicon of the RNA transcript of CD68;

normalizing said level against a level of an amplicon of at least one reference RNA transcript in said tissue sample to provide a normalized CD68 amplicon level;

comparing the normalized CD68 amplicon level to a normalized CD68 amplicon level in reference breast tumor samples; and predicting the likelihood of long-term survival without the recurrence of breast cancer, wherein increased normalized CD68 amplicon level is indicative of a reduced likelihood of long-term survival without recurrence of breast cancer.

11. The method of claim 10, wherein the breast cancer is invasive breast cancer.

12. The method of claim 10, wherein the breast cancer is estrogen receptor (ER) positive breast cancer.

13. The method of claim 10, wherein the cDNA of CD68 is amplified by polymerase chain reaction.

14. The method of claim 10, further comprising the step of preparing a report indicating that the patient has an increased or decreased likelihood of long-term survival without breast cancer recurrence.

15. The method of claim 10, wherein the level of the amplicon of the RNA transcript of CD68 is a threshold cycle (Ct) value and the normalized CD68 amplicon level is a normalized Ct value.

16. The method of claim 10, wherein the reference breast cancer samples comprise at least 40 breast cancer samples.

17. The method of claim 1, wherein the breast cancer tissue sample is a fixed, wax-embedded breast cancer tissue sample.

18. The method of claim 4, wherein the breast cancer tissue sample is a fixed, wax-embedded breast cancer tissue sample.

19. The method of claim 10, wherein the tissue sample is a fixed, wax-embedded tissue sample.

* * * * *